United States Patent
Van Niel et al.

(10) Patent No.: US 8,835,431 B2
(45) Date of Patent: *Sep. 16, 2014

(54) KINASE INHIBITORS

(71) Applicant: Chiesi Farmaceutici S.p.A., Parma (IT)

(72) Inventors: Monique Bodil Van Niel, Harlow (GB); Nicholas Charles Ray, Harlow (GB); Andrew Peter Cridland, Harlow (GB); Christopher Hurley, Harlow (GB); Lilian Alcaraz, Harlow (GB); Terry Aaron Panchal, Harlow (GB); Andrew Stephen Robert Jennings, Harlow (GB); Elisabetta Armani, Harlow (GB)

(73) Assignee: Chiesi Farmaceutici S.p.A., Parma (IT)

( * ) Notice: Subject to any disclaimer, the term of this patent is extended or adjusted under 35 U.S.C. 154(b) by 156 days.

This patent is subject to a terminal disclaimer.

(21) Appl. No.: 13/708,191

(22) Filed: Dec. 7, 2012

(65) Prior Publication Data

US 2013/0150361 A1 Jun. 13, 2013

(30) Foreign Application Priority Data

Dec. 9, 2011 (EP) .................................. 11192894
Oct. 10, 2012 (EP) .................................. 12187932

(51) Int. Cl.
*A61K 31/5377* (2006.01)
*C07D 471/04* (2006.01)

(52) U.S. Cl.
CPC .................................. *C07D 471/04* (2013.01)
USPC .................. 514/233.2; 514/303; 514/253.04; 544/362; 544/127; 546/119

(58) Field of Classification Search
USPC .................. 514/233.2, 303, 253.04; 546/119; 544/362, 127
See application file for complete search history.

(56) References Cited

U.S. PATENT DOCUMENTS

| 2012/0088763 A1 | 4/2012 | Finch et al. |
| 2013/0143914 A1* | 6/2013 | Woo et al. ..................... 514/303 |
| 2013/0150343 A1* | 6/2013 | Van Niel et al. ......... 514/211.15 |

FOREIGN PATENT DOCUMENTS

WO 2007/091152 8/2007

OTHER PUBLICATIONS

European Search Report in Application No. 11192894.1, issued Mar. 14, 2012.

* cited by examiner

*Primary Examiner* — Kristin Vajda
(74) *Attorney, Agent, or Firm* — Oblon, Spivak, McClelland, Maier & Neustadt, L.L.P.

(57) ABSTRACT

Compounds of formula (I):

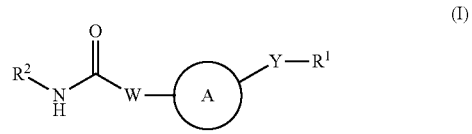

wherein $R^2$, W, A, Y, and $R^1$ are as defined in the specification, and pharmaceutically acceptable salts thereof, are p38 MAPK inhibitors, and are useful as anti-inflammatory agents in the treatment of, inter alia, diseases of the respiratory tract.

12 Claims, No Drawings

KINASE INHIBITORS

CROSS REFERENCES TO RELATED APPLICATIONS

This application claims priority to European Patent Application No. 11192894.1, filed on Dec. 9, 2011 and European Patent Application No. 12187932.4, filed on Oct. 10, 2012, both of which are incorporated herein by reference in their entireties.

BACKGROUND OF THE INVENTION

1. Field of the Invention

The present invention relates to compounds and compositions that are p38 MAPK inhibitors, and which are useful as anti-inflammatory agents in the treatment of, inter alia, diseases of the respiratory tract. The present invention also relates to the treatment and/or prevention of diseases of the respiratory tract.

2. Discussion of the Background

Mitogen activated protein kinases (MAPK) constitute a family of proline-directed serine/threonine kinases that activate their substrates by dual phosphorylation. There are four known human isoforms of p38 MAP kinase, p38α, p38β, p38γ, and p38δ. The p38 kinases, which are also known as cytokine suppressive anti-inflammatory drug binding proteins (CSBP), stress activated protein kinases (SAPK) and RK, are responsible for phosphorylating (see Stein et al., Ann. Rep. Med. Chem., 1996, 31, 289-298, which is incorporated herein by reference in its entirety) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (see Herlaar E. & Brown Z., Molecular Medicine Today, 1999, 5, 439-447, which is incorporated herein by reference in its entirety). The products of p38 phosphorylation have been shown to mediate the production of inflammatory cytokines, including tumor necrosis factor alpha (TNF α) and interleukin-(IL-)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (see, e.g. Dinarello et al., Rev. Infect. Disease, 1984, 6, 51, which is incorporated herein by reference in its entirety). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (see Badger et al., J. Pharm. Exp. Thera., 1996, 279, 1453-1461; Griswold et al, Pharmacol. Comm., 1996, 7, 323-229, which are incorporated herein by reference in their entireties). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α IL-1β, IL-6, IL-4, IL-5 and IL-13 (see Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288, which are incorporated herein by reference in their entireties). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (see Lee et al., Immunopharmacology, 2000, 47, 185-200, which is incorporated herein by reference in its entirety). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425, which is incorporated herein by reference in its entirety).

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467), which are incorporated herein by reference in their entireties. P38 kinase inhibitors containing a triazolopyridine motif are known in the art, see for example WO 2007/091152, WO 2004/072072, and WO 2006/018727, which are incorporated herein by reference in their entireties.

International Patent Application WO 2010/094956 discloses triazolopyridine derivatives of formula (I) as being p38 MAP kinase inhibitors:

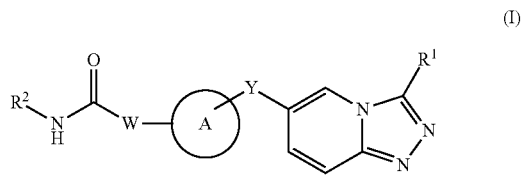

(I)

In such compounds, A represents an optionally substituted divalent arylene radical, an heteroarylene radical, a ($C_3$-$C_6$) divalent cycloalkylene radical having 5 or 6 ring atoms or a pyperidinylene radical. The compounds are said to be useful in as anti-inflammatory agents in the treatment of diseases of the respiratory tract.

However, there remains a need for improved p38 MAP kinase inhibitors.

SUMMARY OF THE INVENTION

Accordingly, it is one object of the present invention to provide novel and potent p38 mitogen activated protein kinase inhibitors.

It is another object of the present invention to provide novel and potent p38 mitogen activated protein kinase inhibitors which are useful in the treatment of inflammatory and obstructive diseases of the respiratory tract.

It is another object of the present invention, to provide novel and potent p38 mitogen activated protein kinase inhibitors which show an appropriate developability profile on inhalatory administration to effectively treat respiratory obstructive or inflammatory diseases. It is to be understood that such profile may be achieved in a number of different ways by modulation of specific properties; by way of example, it could be achieved by administration of a low effective dose of the drug thus limiting side effects or via a long duration of action in the lungs which may reduce the frequency of administration.

It is another object of the present invention to provide novel methods of treating certain diseases and conditions by administering such a p38 mitogen activated protein kinase inhibitor.

These and other objects, which will become apparent during the following detailed description, have been achieved by the inventors' discovery that the compounds of formula (I) are useful as p38 mitogen activated protein kinase inhibitors.

Thus, the present invention provides a compound of formula (I), or a pharmaceutically acceptable salt thereof:

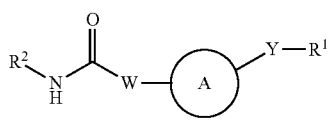

(I)

wherein;

W is a heteroatom selected from N or O, wherein N is substituted with hydrogen, $C_1$-$C_6$ alkyl, or $C_3$-$C_5$-cycloalkyl;

Y is selected from the group consisting of: a group —S(O)$_p$— wherein p is 0, 1, or 2; a group —O(CR$^3$R$^4$)$_n$—; a group —(CR$^5$R$^6$)$_n$—; a group —NR$^7$—; a group —OC(O)—; a group —OC(O)NH—; and a group —OC(O)O—;

$R^3$, $R^4$, $R^5$, and $R^6$ are each independently hydrogen, fluorine, or $C_1$-$C_6$ alkyl; or, respectively, $R^3$ and $R^4$, or $R^5$ and $R^6$ may form, together with the carbon atom to which they are attached, a 3-6 membered saturated carbocyclic monocyclic ring optionally substituted by a group $C_1$-$C_6$ alkyl, hydroxyl, or halo;

n is 0, 1, 2, or 3;

$R^7$ is hydrogen, $C_1$-$C_6$ alkyl, or $C_3$-$C_7$ cycloalkyl, wherein such $C_1$-$C_6$ alkyl, or $C_3$-$C_7$ cycloalkyl are optionally substituted by a group $C_1$-$C_3$ alkyl, $C_3$-$C_6$ cycloalkyl, hydroxyl, cyano, or halo;

$R^1$ is a group selected from (IIa) to (IIc):
wherein

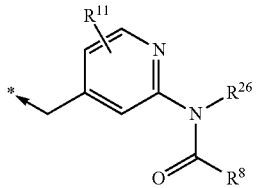

(IIa)

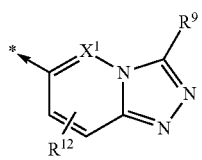

(IIb)

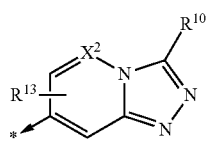

(IIc)

$R^8$ is —($C_1$-$C_6$alkylene)-NR$^A$R$^B$, —($C_3$-$C_7$cycloalkylene)-NR$^A$R$^B$, —NR$^A$R$^B$, —N(R$^C$)—($C_2$-$C_6$alkylene)-NR$^A$R$^B$, —N(R$^C$)—($C_3$-$C_7$cycloalkylene)-NR$^A$R$^B$, or —R$^C$;

$R^A$ and $R^B$ are at each occurrence independently hydrogen, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$ cycloalkyl, —OR$^D$, —SR$^D$, —NR$^E$R$^F$, —CN, or halo; alternatively, $R^A$ and $R^B$ may form, together with the nitrogen atom to which they are attached, a 5-11 membered saturated monocyclic or bicyclic heterocyclic ring system in which the 5-11-membered saturated monocyclic or bicyclic heterocyclic ring is optionally substituted by one or more groups —OR$^D$, —CN, halo, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —OR$^D$, —CN, or halo; and wherein, optionally, the 5-11-membered saturated monocyclic or bicyclic heterocyclic ring contains a further heteroatom which is oxygen or nitrogen, said nitrogen atom optionally substituted by $C_1$-$C_6$ alkyl or $C_3$-$C_6$ cycloalkyl wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —OR$^D$, —CN, or halo;

$R^C$ is at each occurrence independently hydrogen, $C_1$-$C_6$ alkyl, or $C_3$-$C_6$ cycloalkyl, such $C_1$-$C_6$ alkyl and $C_3$-$C_6$ cycloalkyl being optionally substituted by a group $C_1$-$C_3$ alkyl, OR$^D$, —CN, or halo;

$R^D$ is at each occurrence independently hydrogen, —CH$_3$, or —C$_2$H$_5$;

$R^E$ and $R^F$ are at each occurrence independently hydrogen, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —OR$^D$, —SR$^D$, —CN, or halo; and/or $R^E$ and $R^F$ may form, together with the nitrogen atom to which they are attached, a 5-7 membered saturated heterocyclic ring system in which the 5-7 membered saturated heterocyclic ring is optionally substituted by one or more group —OR$^D$, —CN, halo, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —OR$^D$, —CN, or halo; and wherein, optionally, the said 5-7-membered saturated heterocyclic ring contains a further heteroatom which is oxygen or nitrogen, said nitrogen atom optionally substituted by $C_1$-$C_6$ alkyl or $C_3$-$C_6$ cycloalkyl wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^D$, —CN, or halo;

$R^{26}$ is hydrogen, —$CH_3$, or —$C_2H_5$;

$X_1$ and $X_2$ are each independently a group —(CH)— or a nitrogen atom;

$R^9$ and $R^{10}$ are independently, $C_1$-$C_6$ alkyl, $C_3$-$C_6$ cycloalkyl, phenyl which is optionally substituted, 5- or 6-membered monocyclic heteroaryl which is optionally substituted, or a radical of formula (IIIa) or (IIIb):

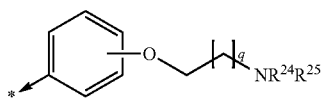

(IIIa)

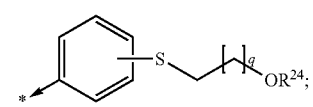

(IIIb)

wherein q is 1 or 2; and $R^{24}$ and $R^{25}$ are independently hydrogen or $C_1$-$C_6$ alkyl, or $R^{24}$ and $R^{25}$ taken together with the nitrogen to which they are attached form a 6-membered heterocyclic ring optionally containing a further heteroatom selected from N and O;

$R^{11}$, $R^{12}$, and $R^{13}$ are independently hydrogen, $C_1$-$C_6$ alkyl, or halogen;

A is a divalent cycloalkylene radical having 5, 6 or 7 ring atoms; said cycloalkylene ring being attached to W and Y, and fused to a phenyl ring or to a monocyclic heteroaryl ring having 5 or 6 ring atoms, such phenyl or heteroaryl ring being optionally substituted by one or two groups $R^{27}$;

$R^{27}$ is at each occurrence independently selected from the group consisting of: $C_1$-$C_6$ alkyl, halogen, and cyano;

$R^2$ is a radical of formula (IVa), (IVb) or (IVc):

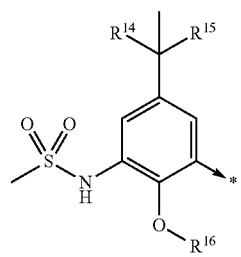

(IVa)

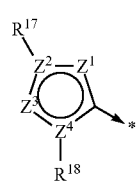

(IVb)

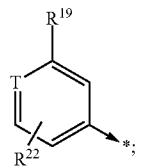

(IVc)

wherein
$R^{14}$ is selected from the group consisting of —F, —$CH_2OMe$, and —$CF_2CF_3$;
$R^{15}$ and $R^{16}$ are independently —$CH_3$ or —$C_2H_5$;
$R^{17}$ is selected from the group consisting of: lone electron pair, hydrogen, —$CF_3$, —$NR^{E1}R^{F1}$, —($C_3$-$C_7$cycloalkyl), —($C_3$-$C_7$heterocycloalkyl), aryl, or heteroaryl wherein any of such —($C_3$-$C_7$cycloalkyl), —($C_3$-$C_7$heterocycloalkyl), aryl, or heteroaryl may be optionally substituted by a group $C_1$-$C_6$ alkyl, $C_3$-$C_7$ cycloalkyl, or halo; or
$R^{17}$ is a group of formula (V):

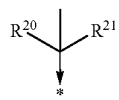

(V)

wherein
$R^{20}$ is selected from the group consisting of —F, —$CH_3$, —$C_2H_5$, —$CH_2OH$, —$CH_2OMe$, —$CF_2CF_3$, —$CH_2SCH_3$, —$SCH_3$, and —$SC_2H_5$;
$R^{21}$ is —$CH_3$ or —$C_2H_5$;
or
$R^{20}$ and $R^{21}$ as defined above may form, together with the carbon atom to which they are attached, a 3-7-membered monocyclic ring;

$R^{E1}$ and $R^{F1}$ are each independently $C_1$-$C_6$ alkyl optionally substituted by a group $C_1$-$C_3$ alkyl, —$OR^G$, —CN, or halo; alternatively, $R^{E1}$ and $R^{F1}$ may also form, together with the nitrogen atom to which they are attached, a 5-11-membered saturated monocyclic or bicyclic heterocyclic ring system in which the said 5-11-membered saturated monocyclic or bicyclic heterocyclic ring is optionally substituted by one or more group —$OR^G$, —CN, halo, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^G$, —CN, or halo; and wherein, optionally, the 5-11-membered saturated monocyclic or bicyclic heterocyclic ring contains a further heteroatom which is oxygen or nitrogen, said nitrogen atom optionally substituted by $C_1$-$C_6$ alkyl or $C_3$-$C_6$ cycloalkyl;

$R^G$ is independently at each occurrence hydrogen, —$CH_3$, or —$C_2H_5$;

$R^{18}$ is selected from the group consisting of lone electron pair, hydrogen, aryl, heteroaryl, —($C_1$-$C_6$alkyl), —($C_3$-$C_7$cycloalkyl), —($C_3$-$C_7$heterocycloalkyl), —($C_5$-$C_7$heterocycloalkyl)-($C_1$-$C_6$alkyl), and ($C_5$-$C_7$heterocycloalkyl)-($C_3$-$C_6$ cycloalkyl); wherein any of such aryl, heteroaryl, —($C_1$-$C_6$alkyl), —($C_3$-$C_7$cycloalkyl), —($C_3$-$C_7$heterocycloalkyl), ($C_5$-$C_7$heterocycloalkyl)-($C_1$-$C_6$alkyl), or ($C_5$-$C_7$heterocycloalkyl)-($C_3$-$C_6$ cycloalkyl) may be optionally substituted by a group —CN, —OH, halo, —$COOR^M$, $C_1$-$C_6$alkyl, $C_3$-$C_6$cycloalkyl, —O—($C_1$-$C_6$alkyl), —O—($C_3$-$C_6$cycloalkyl), —S—($C_1$-$C_6$alkyl), —S—($C_3$-$C_6$cycloalkyl), —$NR^HR^J$, —$N(R^L)(C_2$-$C_6$alkylene)-$NR^HR^J$, —$N(R^L)(C_3$-$C_7$cycloalkylene)-

$NR^HR^J$, —($C_1$-$C_6$alkylene)-$NR^HR^J$, —($C_3$-$C_7$cycloalkylene)-$NR^HR^J$, —O—($C_2$-$C_6$alkylene)-$NR^HR^J$, —O—($C_3$-$C_7$cycloalkylene)-$NR^HR^J$, —S—($C_2$-$C_6$alkylene)-$NR^HR^J$, —S—($C_3$-$C_7$cycloalkylene)-$NR^HR^J$, —N($R^L$)C(O)—($C_1$-$C_6$alkylene)-$NR^HR^J$, —N($R^L$)C(O)—($C_3$-$C_7$cycloalkylene)-$NR^HR^J$, —C(O)N($R^L$)—($C_2$-$C_6$alkylene)-$NR^HR^J$, —C(O)N($R^L$)—($C_3$-$C_7$cycloalkylene)-$NR^HR^J$, —C(O)N($R^L$)—($C_2$-$C_6$alkylene)-$OR^M$, —C(O)N($R^L$)—($C_3$-$C_7$cycloalkylene)-$OR^M$, —N($R^L$)C(O)N($R^HR^J$), —C(O)N($R^HR^J$), —N($R^L$)C(O)N($R^L$)—($C_2$-$C_6$alkylene)-$NR^HR^J$, —N($R^L$)C(O)N($R^L$)—($C_3$-$C_7$cycloalkylene)-$NR^HR^J$, —O—($C_2$-$C_6$alkylene)-$OR^M$, —O—($C_3$-$C_7$cycloalkylene)-$OR^M$, —S—($C_2$-$C_6$alkylene)-$OR^M$, —S—($C_3$-$C_7$cycloalkylene)-$OR^M$, —N($R^L$)S(O)$_2$—($C_1$-$C_6$alkylene)-$NR^HR^J$, —N($R^L$)S(O)$_2$—($C_3$-$C_7$cycloalkylene)-$NR^HR^J$, —S(O)$_2$N($R^L$)—($C_2$-$C_6$alkylene)-$NR^HR^J$, —S(O)$_2$N($R^L$)—($C_3$-$C_7$cycloalkylene)-$NR^HR^J$, —S(O)$_2$N($R^L$)—($C_2$-$C_6$alkylene)-$OR^M$, —S(O)$_2$N($R^L$)—($C_3$-$C_7$cycloalkylene)-$OR^M$, —N($R^L$)S(O)$_2$—($C_2$-$C_6$alkylene)-$OR^M$, —N($R^L$)S(O)$_2$—($C_3$-$C_7$cycloalkylene)-$OR^M$, —S(O)$_2$N($R^HR^J$), —N($R^L$)S(O)$_2R^L$, —N($R^L$)C(O)$R^L$, $OR^L$, $SR^L$, —($C_3$-$C_7$heterocycloalkyl), —($C_5$-$C_7$heterocycloalkyl)-($C_1$-$C_6$ alkyl), and —($C_5$-$C_7$ heterocycloalkyl)-($C_3$-$C_6$ cycloalkyl); wherein any of such $C_1$-$C_6$alkyl, $C_3$-$C_6$cycloalkyl, —($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl), and ($C_5$-$C_7$heterocycloalkyl)carbonyl portion in the above listed groups may be optionally substituted by a group $C_1$-$C_6$ alkyl, $C_3$-$C_7$ cycloalkyl, —$OR^M$, or halo;

$R^H$ and $R^J$ are at each occurrence independently hydrogen, $C_1$-$C_6$ alkyl, or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN, or halo; alternatively, $R^H$ and $R^J$ may also form, together with the nitrogen atom to which they are attached, a 5-11 membered saturated monocyclic or bicyclic heterocyclic ring system in which the 5-11-membered saturated monocyclic or bicyclic heterocyclic ring is optionally substituted by one or more group —$OR^M$, —CN, halo, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^M$, —CN, or halo; and wherein, optionally, the 5-11-membered saturated monocyclic or bicyclic heterocyclic ring contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^M$, —CN, or halo; and/or $R^H$ and $R^J$ may be linked to one carbon atom of the —($C_2$-$C_6$alkylene)- or —($C_3$-$C_7$cycloalkylene)- portion of the group linked to the nitrogen to which they are connected to form a saturated cycle of up to 6 ring atoms;

$R^L$ is at each occurrence independently hydrogen, $C_1$-$C_6$ alkyl, or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN, or halo.

$R^M$ is at each occurrence independently hydrogen, $C_1$-$C_4$ alkyl, or $C_3$-$C_6$ cycloalkyl, such $C_1$-$C_4$ alkyl or $C_3$-$C_6$ cycloalkyl being optionally substituted by a group hydroxyl, —CN, or halo;

$R^{19}$ is selected from the group consisting of hydrogen, —$CF_3$, —$NR^ER^F$, —($C_3$-$C_7$cycloalkyl), —($C_3$-$C_7$heterocycloalkyl), aryl, and heteroaryl wherein any of such —($C_3$-$C_7$cycloalkyl), —($C_3$-$C_7$heterocycloalkyl), aryl, or heteroaryl may be optionally substituted by a group $C_1$-$C_6$ alkyl, $C_3$-$C_7$ cycloalkyl, or halo; or $R^{19}$ is a group of formula (V):

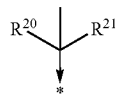

wherein $R^{20}$, $R^{21}$, $R^E$ and $R^F$ are as above defined;

$z^1$, $z^2$, $z^3$, and $z^4$ are independently selected in the group consisting of: C, N, S, O, a group —CH—, and a group —NH—, in such a combination that the resulting ring formed is an aromatic system;

T is —N═ or —$CR^{28}$═;

$R^{28}$ is H, halo, —$CH_3$, or —CN;

$R^{22}$ is H, halo, —$CH_3$, or —CN;

with the provisos that:
when $z^1$═—CH—, $z^2$═—C—, $z^3$═—O—, $z^4$═—N—, $R^{18}$ is an electron lone pair, $R^{17}$ is a group of formula (V), and $R^{21}$ is —$CH_3$ or —$C_2H_5$;
then $R^{20}$ is —F, —$CH_2OMe$ or —$CF_2CF_3$;
when $z^1$═—CH—, $z^2$═—C—, $z^3$═—N—, $z^4$═—N—, $R^{17}$ is a group of formula (V), $R^{21}$ is —$CH_3$ or —$C_2H_5$ and $R^{20}$ is —$CH_3$, —$C_2H_5$; —$CH_2OH$, —$CH_2SCH_3$, —$SCH_3$, or —$SC_2H_5$, and $R_{18}$ is a phenyl ring;
then such phenyl ring is substituted by a group which is selected from the group consisting of —CN, —$COOR^M$, $C_3$-$C_6$cycloalkyl, —O—($C_1$-$C_6$alkyl), —O—($C_3$-$C_6$cycloalkyl), —S—($C_1$-$C_6$alkyl), —S—($C_3$-$C_6$cycloalkyl), —$NR^HR^J$, —N($R^L$)($C_2$-$C_6$alkylene)-$NR^HR^J$, —N($R^L$)($C_3$-$C_7$cycloalkylene)-$NR^HR^J$, —($C_3$-$C_7$cycloalkylene)-$NR^HR^J$, —O—($C_3$-$C_7$cycloalkylene)-$NR^HR^J$, —S—($C_2$-$C_6$alkylene)-$NR^HR^J$, —S—($C_3$-$C_7$cycloalkylene)-$NR^HR^J$, —N($R^L$)C(O)—($C_1$-$C_6$alkylene)-$NR^HR^J$, —N($R^L$)C(O)—($C_3$-$C_7$cycloalkylene)-$NR^HR^J$, —C(O)N($R^L$)—($C_2$-$C_6$alkylene)-$NR^HR^J$, —C(O)N($R^L$)—($C_3$-$C_7$cycloalkylene)-$NR^HR^J$, —C(O)N($R^L$)—($C_2$-$C_6$alkylene)-$OR^M$, —C(O)N($R^L$)—($C_3$-$C_7$cycloalkylene)-$OR^M$, —N($R^L$)C(O)$NR^HR^J$, —C(O)$NR^HR^J$, —N($R^L$)C(O)N($R^L$)—($C_2$-$C_6$alkylene)-$NR^HR^J$, —N($R^L$)C(O)N($R^L$)—($C_3$-$C_7$cycloalkylene)-$NR^HR^J$, —O—($C_2$-$C_6$alkylene)-$OR^M$, —O—($C_3$-$C_7$cycloalkylene)-$OR^M$, —S—($C_2$-$C_6$alkylene)-$OR^M$, —S—($C_3$-$C_7$cycloalkylene)-$OR^M$, —N($R^L$)S(O)$_2$—($C_1$-$C_6$alkylene)-$NR^HR^J$, —N($R^L$)S(O)$_2$—($C_3$-$C_7$cycloalkylene)-$NR^HR^J$, —S(O)$_2$N($R^L$)—($C_2$-$C_6$alkylene)-$NR^HR^J$, —S(O)$_2$N($R^L$)—($C_3$-$C_7$cycloalkylene)-$NR^HR^J$, —S(O)$_2$N($R^L$)—($C_2$-$C_6$alkylene)-$OR^M$, —S(O)$_2$N($R^L$)—($C_3$-$C_7$cycloalkylene)-$OR^M$, —N($R^L$)S(O)$_2$—($C_2$-$C_6$alkylene)-$OR^M$, —N($R^L$)S(O)$_2$—($C_3$-$C_7$cycloalkylene)-$OR^M$, —S(O)$_2$N($R^HR^J$), —N($R^L$)S(O)$_2R^L$, —N($R^L$)C(O)$R^L$, $SR^L$, —($C_3$-$C_7$heterocycloalkyl), —($C_5$-$C_7$heterocycloalkyl)-($C_1$-$C_6$ alkyl), and ($C_5$-$C_7$ heterocycloalkyl)-($C_3$-$C_6$cycloalkyl); wherein any of such $C_1$-$C_6$alkyl, $C_3$-$C_6$cycloalkyl, —($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl), and ($C_5$-$C_7$heterocycloalkyl)carbonyl portion in the above listed groups may be optionally substituted by a group $C_1$-$C_6$ alkyl, $C_3$-$C_7$ cycloalkyl, —$OR^M$, or halo;

or such phenyl ring is substituted by a group which is —($C_1$-$C_6$alkylene)-$NR^HR^J$ or —O—($C_2$-$C_6$alkylene)-$NR^HR^J$ wherein $R^H$ and $R^J$, which are not both hydrogen, are at each occurrence independently hydrogen, $C_1$-$C_6$ alkyl, or $C_3$-$C_6$ cycloalkyl, such $C_1$-$C_6$ alkyl or $C_3$-$C_6$ cycloalkyl being substituted by a group —$OR^M$, —CN, or halo; alternatively, $R^H$ and $R^J$ may form, together with the nitrogen atom to which they are attached, a 5-11 membered saturated heterocyclic monocyclic or bicyclic ring system in which the 5-11-membered saturated heterocyclic monocyclic or bicyclic ring is substituted by one or more groups —$OR^M$, —CN, halo, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^M$, —CN, or halo; and wherein, optionally, the 5-11-membered saturated monocyclic or bicyclic heterocyclic ring contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —$OR^M$, —CN, or halo;

or such phenyl ring is substituted by a group ($C_5$-$C_7$heterocycloalkyl)-($C_1$-$C_6$ alkyl), which is substituted by a group $C_1$-$C_6$ alkyl, $C_3$-$C_7$ cycloalkyl, —$OR^M$, or halo;

or such phenyl ring is substituted by a group —$OR^L$ wherein $R^L$ is $C_1$-$C_6$ alkyl or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN, or halo;

or such phenyl ring is substituted by a group $C_1$-$C_6$ alkyl which is substituted by a group $C_3$-$C_7$ cycloalkyl, $OR^M$, or halo; and when $R^{19}$ is a morpholine ring and T is —$CR^{28}$= or —N=;

then $R^{22}$, if present at position ortho to group T of the aromatic ring, is —$CH_3$ or —CN.

In another aspect, the present invention provides pharmaceutical compositions comprising a compound of the invention, or a pharmaceutically acceptable salt thereof, together with one or more pharmaceutically acceptable carriers and/or excipients. Particularly preferred are compositions adapted for inhalation for pulmonary administration.

The compounds of the present invention are inhibitors of p38 mitogen activated protein kinase ("p38 MAPK," "p38 kinase," or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

It is believed that the compounds of the present invention can be used to treat p38 mediated diseases such as: chronic obstructive pulmonary disease (COPD), asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Thus, in another aspect, the present invention provides methods for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, broncietasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

DETAILED DESCRIPTION OF THE PREFERRED EMBODIMENTS

As used herein, the terms "halogen" or "halo" include fluorine, chlorine, bromine, and iodine atoms.

As used herein, the term "$C_x$-$C_y$alkyl" wherein x and y are integers, refers to a straight or branched chain alkyl radical having from x to y carbon atoms. Thus, when x is 1 and y is 6, for example, the term includes methyl, ethyl, n-propyl, isopropyl, n-butyl, isobutyl, sec-butyl, t-butyl, n-pentyl, and n-hexyl.

As used herein, the term "$C_x$-$C_y$alkylene" wherein x and y are integers, refers to a $C_x$-$C_y$alkyl radical having in total two unsatisfied valencies, such as a divalent methylene or ethylene radical.

As used herein, the term "carbocyclic" ring refers to a mono-, bi-, or tricyclic radical having up to 16 ring atoms, all of which are carbon, and includes aryl and cycloalkyl.

As used herein, the term "$C_z$-$C_k$cycloalkyl" wherein z and k are integers refers to a monocyclic saturated carbocyclic radical having from z to k carbon atoms and includes, for example, cyclopropyl, cyclobutyl, cyclopentyl, cyclohexyl, cycloheptyl, and cyclooctyl. Comprised within the scope of the term "$C_z$-$C_k$cycloalkyl" are those radicals having two unsatisfied valencies on the same carbon atom which will link to any $C_x$-$C_y$alkyl, $C_x$-$C_y$alkylene, $C_z$-$C_k$cycloalkyl, $C_z$-$C_k$cycloalkylene, $C_z$-$C_k$heterocycloalkyl, $C_z$-$C_k$heterocycloalkyl$C_x$-$C_y$alkyl, $C_z$-$C_k$heterocycloalkyl$C_z$-$C_k$cycloalkyl or ($C_z$-

$C_k$)heterocycloalkylcarbonyl group by replacement of two hydrogen atoms placed on the same carbon. In such circumstances, this radical forms a gem-disubstituted or spyro system together with the $C_x$-$C_y$alkyl, $C_x$-$C_y$alkylene $C_z$-$C_k$cycloalkyl $C_z$-$C_k$cycloalkylene, $C_z$-$C_k$heterocycloalkyl, $C_z$-$C_k$heterocycloalkyl$C_x$-$C_y$alkyl, $C_z$-$C_k$heterocycloalkyl$C_z$-$C_k$cycloalkyl, or ($C_z$-$C_k$)heterocycloalkylcarbonyl group it is linked to.

The term "$C_z$-$C_k$cycloalkylene radical" refers to a $C_z$-$C_k$-cycloalkyl radical having two unsatisfied valencies on different carbon atoms in the cycle, as such as 1,3-cyclopentylene, 1,4-cyclohexylene and 1,4-cycloheptylene as follows:

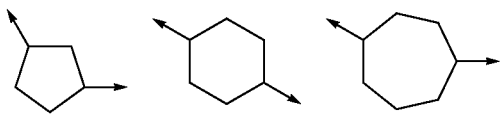

As used herein, the unqualified term "aryl" refers to a mono- or bi-cyclic carbocyclic aromatic radical, and includes radicals having two monocyclic carbocyclic aromatic rings which are directly linked by a covalent bond. Illustrative of such radicals are phenyl, biphenyl, and napthyl.

As used herein, the unqualified term "heteroaryl" refers to a mono- or bi-cyclic aromatic radical containing one or more heteroatoms selected from S, N, and O, and includes radicals having two such monocyclic rings, or one such monocyclic ring and one monocyclic aryl ring, which are fused through a common bond. Illustrative examples of 5,6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, and triazinyl. Illustrative examples of 8,10-membered heteroaryl are: benzothienyl, benzofuryl, benzimidazolyl, benzothiazolyl, benzisothiazolyl, benzoxazolyl, benzisoxazolyl, benzotriazolyl, indolyl, and indazolyl.

As used herein, the unqualified term "heterocyclyl" or "heterocyclic" and relates to a saturated mono-, bi-, or tricyclic non-aromatic radical containing one or more heteroatoms selected from S, N, and O. In particular, the term "$C_z$-$C_k$heterocycloalkyl" refers to monocyclic ($C_z$-$C_k$)cycloalkyl groups, in which at least one ring carbon atom is replaced by a heteroatom (e.g. N, NH, S, or O). Examples of ($C_z$-$C_k$) heterocycloalkyl include pyrrolidinyl, thiazolidinyl, piperazinyl, piperidinyl, morpholinyl, thiomorpholinyl.

By analogy, the term "$C_z$-$C_k$heterocycloalkylene", refers to a divalent $C_z$-$C_k$heterocycloalkyl radical, wherein $C_z$-$C_k$heterocycloalkyl is as above defined.

The term "$C_z$-$C_k$heterocycloalkyl$C_x$-$C_y$alkyl" refers to the above "$C_x$-$C_y$alkyl" group wherein one or more hydrogen atoms are replaced by one or more "$C_z$-$C_k$heterocycloalkyl" groups. Comprised within the scope of the term "$C_z$-$C_k$heterocycloalkyl$C_x$-$C_y$alkyl" are systems where two hydrogen atoms linked to the same carbon atom in "$C_x$-$C_y$alkyl" group are replaced by one "$C_z$-$C_k$heterocycloalkyl" group. Such radical thus form a gem-disubstituted "$C_z$-$C_k$heterocycloalkyl$C_x$-$C_y$alkyl" system, such as a 1,2-dimethyl-pyrrolidin-2-yl radical.

The term "$C_z$-$C_k$heterocycloalkyl$C_z$-$C_k$cycloalkyl" refers to the above "$C_z$-$C_k$ cycloalkyl" group wherein one or more hydrogen atoms are replaced by one or more "$C_z$-$C_k$heterocycloalkyl" groups.

The expression "($C_z$-$C_k$)cycloalkylcarbonyl" refers to ($C_z$-$C_k$)cycloalkyl-CO-groups wherein the group "($C_z$-$C_k$)cycloalkyl" has the meaning above defined.

The expression "($C_z$-$C_k$)heterocycloalkylcarbonyl" refers to ($C_z$-$C_k$)heterocycloalkyl-CO— groups wherein the group "($C_z$-$C_k$)heterocycloalkyl" has the meaning above defined.

Unless otherwise specified in the context in which it occurs, the term "substituted" as applied to any aryl or heteroaryl moiety herein means substituted with at least one substituent, for example selected from ($C_1$-$C_6$)alkyl, ($C_1$-$C_6$) fluoroalkyl, ($C_1$-$C_6$)alkoxy (including methylenedioxy and ethylenedioxy substitution on adjacent carbon atoms of an aromatic ring), ($C_1$-$C_6$)fluoroalkoxy, ($C_1$-$C_6$)alkoxy-($C_1$-$C_6$) alkyl, benzyloxy-($C_1$-$C_6$)alkyl, ($C_1$-$C_6$)alkoxy-($C_1$-$C_6$) alkoxy, benzyloxy-($C_1$-$C_6$)alkoxy, hydroxy, hydroxy($C_1$-$C_6$) alkyl, hydroxy($C_1$-$C_6$)alkoxy, hydroxy($C_1$-$C_6$)alkylthio, mercapto, mercapto($C_1$-$C_6$)alkyl, ($C_1$-$C_6$)alkylthio, cyclopropyl, halo (including fluoro and chloro), O-benzyl, nitro, nitrile (cyano), —COOH, tetrazolyl, —COOR$^a$, —COR$^b$, —SO$_2$R$^a$, —CONH$_2$, —SO$_2$NH$_2$, —CONHR$^a$, —SO$_2$NHR$^a$, —CONR$^a$R$^b$, —SO$_2$NR$^a$R$^b$, —NH$_2$, —NHR$^a$, —NR$^a$R$^b$, —OCONH$_2$, —OCONHR$^a$, —OCONR$^a$R$^b$, —NHCOR$^a$, —NHCOOR$^a$, —NR$^b$COOR$^a$ —NHSO$_2$OR$^a$, —NR$^b$SO$_2$OR$^a$, —NHCONH$_2$, —NR$^a$-CONH$_2$, —NHCONHR$^b$, —NR$^a$CONHR$^b$, —NHCONR$^a$R$^b$, or —NR$^a$CONR$^a$R$^b$ wherein R$^a$ and R$^b$ are independently a ($C_1$-$C_4$)alkyl group, or R$^a$ and R$^b$ when attached to the same nitrogen may form, together with that nitrogen, a cyclic amino group such as a morpholinyl, piperidinyl, or piperazinyl group. An "optional substituent" may be one of the substituent groups encompassed in the above description.

Compounds of the invention may exist in one or more geometrical, optical, enantiomeric, diastereomeric, and tautomeric forms, including but not limited to cis- and transforms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

Throughout the specification the use of an asterisk "*" in the definition of a structural formula, indicates the point of attachment for the radical group to the rest of the molecule.

As used herein the term "salt" includes base addition, acid addition, and ammonium salts. As briefly mentioned above, compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine, and the like. Those compounds of the invention which are basic can form salts, including pharmaceutically acceptable salts with inorganic acids, e.g. with hydrohalic acids such as hydrochloric or hydrobromic acids, sulphuric acid, nitric acid, or phosphoric acid and the like, and with organic acids e.g. with formic, acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids, and the like. Those compounds (1) which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002), which is incorporated herein by reference in its entirety.

It is expected that compounds of the invention may be prepared in the form of hydrates, and solvates. Any reference herein, including the claims herein, to "compounds with which the invention is concerned," or "compounds of the invention," or "the present compounds," and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the present invention may exist in several polymorphic forms and may be obtained in different crystal or co-crystal habits, and they are intended to be included within the meaning of the term "compounds of the invention."

The compounds of the present invention may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis), which are incorporated herein by reference in their entireties.

Prodrugs in accordance with the present invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985), which is incorporated herein by reference in its entirety. Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$), or an amidine (—C(=N—O—CH$_3$)—NH$_2$).

It is to be understood that all preferred groups or embodiments described herebelow for compounds of formula (I) may be combined among each other and apply as well to compounds of formula (IA), (IB), (Ia), (Ib) or (Ic) as below defined mutatis mutandis.

In one embodiment, compounds of formula (Ia) are provided, which are compounds of formula (I) as above defined wherein carbon stereogenic center on the cycloalkylene portion of ring A which is linked to group W and identified with number (1) herebelow, possess the absolute configuration herebelow represented:

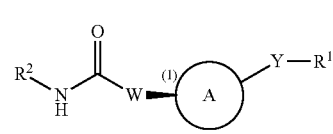

In another embodiment, compounds of formula (Ib) are provided, which are compounds of formula (I) as above defined wherein carbon stereogenic center on the cycloalkylene portion of ring A which are linked to group W and Y and identified, respectively, with numbers (1) and (2) herebelow, possess the absolute configuration herebelow represented:

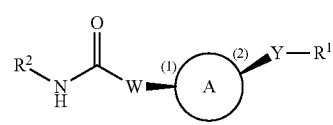

In a further embodiment, compound of formula (Ic) are provided, which are compounds of formula (I) as above defined wherein carbon stereogenic center on the cycloalkylene portion of ring A which are linked to group W and Y and identified, respectively, with numbers (1) and (2) herebelow, possess the absolute configuration herebelow represented:

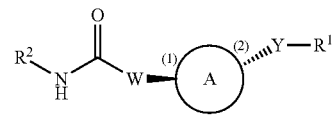

In one embodiment, W is NH or O. In a further embodiment, W is NH.

In one embodiment, Y is a group —S(O)$_p$—, a group —O(CR$^3$R$^4$)$_n$—, a group —(CR$^5$R$^6$)$_n$—, or a group —NR$^7$—; p is zero and n is 0, 1 or 2. In another embodiment, Y is —S(O)$_p$— or a group —O(CR$^3$R$^4$)$_n$ or; p is zero and n is 0 or 1. In a further embodiment, Y is a group —O(CR$^3$R$^4$)$_n$— and n is 0.

In one embodiment, R$^3$, R$^4$, R$^5$, and R$^6$ are each independently hydrogen, fluorine, or C$_1$-C$_6$ alkyl. In another embodiment, R$^3$, R$^4$, R$^5$, and R$^6$ are hydrogen.

In one embodiment, R$^7$ is hydrogen, C$_1$-C$_6$ alkyl, or C$_3$-C$_7$ cycloalkyl.

In one embodiment, R$^7$ is hydrogen.

In one embodiment, A is a divalent cycloalkylene radical having 5 or 6 ring atoms; said cycloalkylene ring being attached to W and Y, and fused to a phenyl ring or to a monocyclic heteroaryl ring having 5 or 6 ring atoms, and such phenyl or heteroaryl ring being optionally substituted by one or two groups R$^{24}$.

In a further embodiment, A is a group selected from the group consisting of:

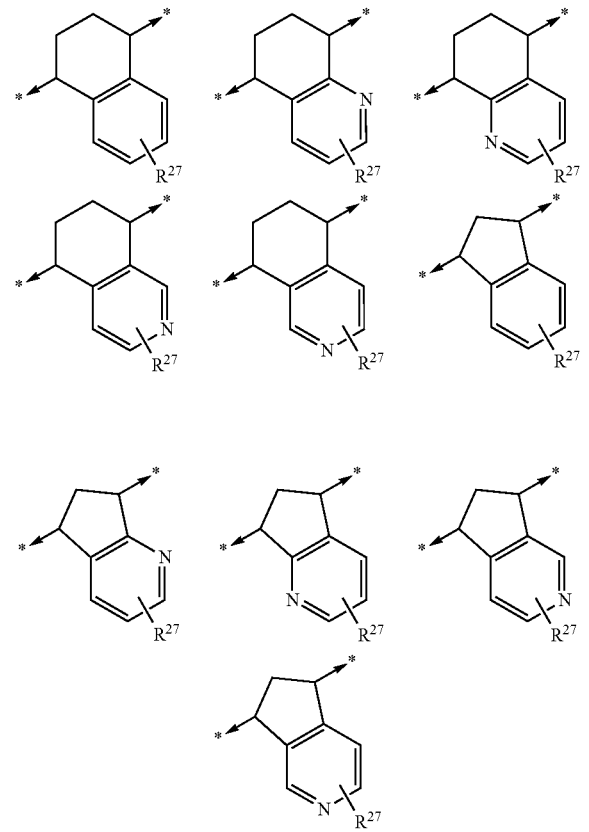

In a still further embodiment, A is group:

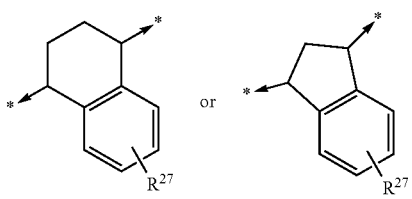

In an additional embodiment, A is group:

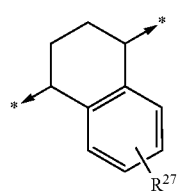

In one embodiment, $R^{27}$ is not present or, if present, is at each occurrence independently selected from the group consisting of: $C_1$-$C_2$ alkyl, —F, —Cl, and cyano; in a further embodiment, $R^{27}$ is not present or, if present, is at each occurrence independently methyl or —F. In a further embodiment, $R^{27}$ is not present.

In one embodiment, $R^1$ is a group of formula (IIa):

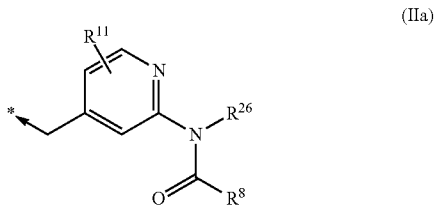

(IIa)

In one embodiment, $R^{11}$ hydrogen.

In one embodiment $R^{26}$ is hydrogen, —$CH_3$, or —$C_2H_5$; in another embodiment, $R^{26}$ is hydrogen, or —$CH_3$; in a further embodiment $R^{26}$ is hydrogen.

In one embodiment, $R^8$ is —($C_1$-$C_6$alkylene)-$NR^AR^B$, —$N(R^AR^B)$, —$N(R^C)$—($C_2$-$C_6$alkylene)-$NR^AR^B$, —$N(R^C)$—($C_3$-$C_7$cycloalkylene)-$NR^AR^B$ or —$R^C$; in another embodiment $R^8$ is —$R^C$.

In one embodiment, $R^8$ is —$CH_2$—OMe.

In another embodiment, $R^1$ is a group of formula (IIb):

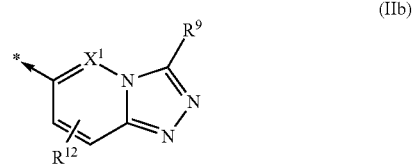

(IIb)

In one embodiment, $X^1$ is a nitrogen atom or a group —CH—; in another embodiment, $X^1$ is a nitrogen atom; in another embodiment, $X^1$ is a group —CH—.

In one embodiment, $R^{12}$ hydrogen.

In one embodiment, $R^9$ is $C_1$-$C_6$ alkyl, $C_3$-$C_6$ cycloalkyl, phenyl which is optionally substituted, 5- or 6-membered monocyclic heteroaryl which is optionally substituted. In a further embodiment, $R^9$ is $C_1$-$C_6$ alkyl, $C_3$-$C_6$ cycloalkyl. In a still further embodiment, $R^9$ is $C_1$-$C_6$ alkyl, for example isopropyl. In another embodiment, $R^9$ is phenyl which is optionally substituted by one or two halogen atoms, for example chlorine.

In another embodiment, $R^9$ is a radical of formula (IIIa) or (IIIb)

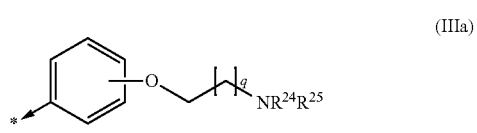

(IIIa)

(IIIb)

In another embodiment, $R^1$ is a group of formula (IIc):

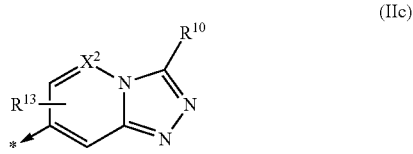
(IIc)

In one embodiment, $X^2$ is a nitrogen atom or a group —CH—; in another embodiment, $X^2$ is a group —CH—.

In one embodiment, $R^{13}$ hydrogen.

In one embodiment, $R^{10}$ is $C_1$-$C_6$ alkyl, $C_3$-$C_6$ cycloalkyl, phenyl which is optionally substituted, 5- or 6-membered monocyclic heteroaryl which is optionally substituted. In a further embodiment, $R^{10}$ is $C_1$-$C_6$ alkyl, $C_3$-$C_6$ cycloalkyl. In a still further embodiment, $R^{10}$ is $C_1$-$C_6$ alkyl.

In another embodiment, $R^{10}$ is a radical of formula (IIIa) or (IIIb)

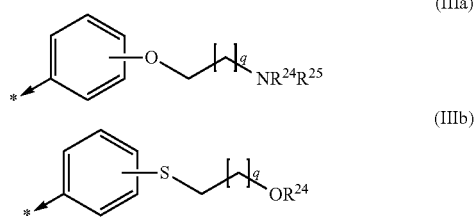
(IIIa)

(IIIb)

In one embodiment, $R^2$ is a radical of formula (IVa):

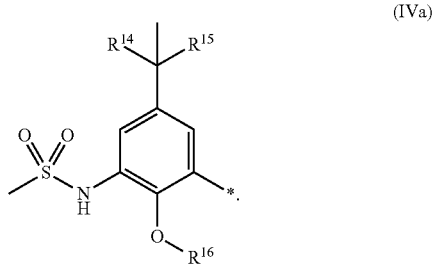
(IVa)

In one embodiment, $R^{14}$ is selected in the group consisting of: —F, —CH$_2$OMe, and —CF$_2$CF$_3$.

In one embodiment, $R^{15}$ and $R^{16}$ are independently —CH$_3$ or —C$_2$H$_5$; in another embodiment, $R^{15}$ and $R^{16}$ are —CH$_3$.

In another embodiment, $R^2$ is a radical of formula (IVb):

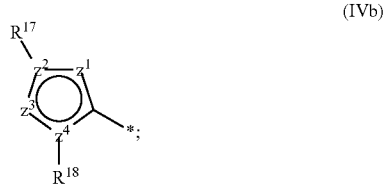
(IVb)

In one embodiment, $R^{17}$ is selected from the group consisting of: lone electron pair, hydrogen, —CF$_3$, —NR$^{E1}$R$^{F1}$, —(C$_3$-C$_6$cycloalkyl), —(C$_4$-C$_6$heterocycloalkyl), aryl, or heteroaryl wherein any of such —(C$_3$-C$_7$cycloalkyl), —(C$_4$-C$_6$heterocycloalkyl), aryl, or heteroaryl may be optionally substituted by a group methyl, isopropyl, or halo. In another embodiment, $R^{17}$ is selected from the group consisting of: lone electron pair, hydrogen, —CF$_3$, morpholine, cyclohexyl, phenyl, or pyridyl.

In another embodiment, $R^{17}$ is a group of general formula (IV)

(IV)

In one embodiment, $R^{20}$ is selected in the group consisting of —F, —CH$_3$; —CH$_2$OH, —CH$_2$OMe, and —CH$_2$SCH$_3$; in another embodiment, $R^{20}$ is selected in the group consisting of —CH$_3$, —CH$_2$OH, and —CH$_2$OMe. In a further embodiment, $R^{20}$ is —CH$_3$.

In one embodiment, $R^{21}$ is —CH$_3$.

In another embodiment, $R^{20}$ and $R^{21}$ as defined above may form, together with the carbon atom to which they are attached, a cyclohexane or cyclopropyl ring; in a further embodiment, $R^{20}$ and $R^{21}$ as defined above may form, together with the carbon atom to which they are attached, a cyclopropyl ring.

In one embodiment, $R^{E1}$ and $R^{F1}$ are each independently $C_1$-$C_3$ alkyl optionally substituted by a group $C_1$-$C_2$ alkyl, —OR$^G$, CN, or halo. In a further embodiment, $R^{E1}$ and $R^{F1}$ are each independently $C_1$-$C_3$ alkyl.

In another embodiment, $R^{E1}$ and $R^{F1}$ form, together with the nitrogen atom to which they are attached, a 5-6-membered saturated monocyclic or bicyclic ring system optionally containing a further heteroatom which is oxygen or nitrogen, said nitrogen atom optionally substituted by $C_1$-$C_2$ alkyl or $C_3$-$C_7$cycloalkyl. In a further embodiment, $R^{E1}$ and $R^{F1}$ form, together with the nitrogen atom to which they are attached, a morpholine, pyran, furan, piperidine, pyrrolidine, or piperazine in which, when possible, the nitrogen atom is optionally substituted by methyl.

In one embodiment, $R^{18}$ is phenyl which is optionally substituted by a group —CN, OH, halo, COOR$^M$, C$_1$-C$_6$alkyl, C$_3$-C$_6$cycloalkyl, —O—(C$_1$-C$_6$alkyl), —O—(C$_3$-C$_6$cycloalkyl), —S—(C$_1$-C$_6$alkyl), —S—(C$_3$-C$_6$cycloalkyl), —NR$^H$R$^J$, —N(R$^L$)(C$_2$-C$_6$alkylene)-NR$^H$R$^J$, —N(R$^L$)(C$_3$-C$_7$cycloalkylene)-NR$^H$R$^J$, —(C$_1$-C$_6$alkylene)-NR$^H$R$^J$, —(C$_3$-C$_7$cycloalkylene)-NR$^H$R$^J$, —O—(C$_2$-C$_6$alkylene)-NR$^H$R$^J$, —O—(C$_3$-C$_7$cycloalkylene)-NR$^H$R$^J$, —S—(C$_2$-C$_6$alkylene)-NR$^H$R$^J$, —S—(C$_3$-C$_7$cycloalkylene)-NR$^H$R$^J$, —N(R$^L$)C(O)—(C$_1$-C$_6$alkylene)-NR$^H$R$^J$, —N(R$^L$)C(O)—(C$_3$-C$_7$cycloalkylene)-NR$^H$R$^J$, —C(O)N(R$^L$)—(C$_2$-C$_6$alkylene)-NR$^H$R$^J$, —C(O)N(R$^L$)—(C$_3$-C$_7$cycloalkylene)-NR$^H$R$^J$, —C(O)N(R$^L$)—(C$_2$-C$_6$alkylene)-OR$^M$, —C(O)N(R$^L$)—(C$_3$-C$_7$cycloalkylene)-OR$^M$, —N(R$^L$)C(O)N(R$^H$R$^J$), —C(O)N(R$^H$R$^J$), —N(R$^L$)C(O)N(R$^L$)—(C$_2$-C$_6$alkylene)-NR$^H$R$^J$, —N(R$^L$)C(O)N(R$^L$)—(C$_3$-C$_7$cycloalkylene)-NR$^H$R$^J$, —O—(C$_2$-C$_6$alkylene)-OR$^M$, —O—(C$_3$-C$_7$cycloalkylene)-OR$^M$, —S—(C$_2$-C$_6$alkylene)-OR$^M$, —S—(C$_3$-C$_7$cycloalkylene)-OR$^M$, —N(R$^L$)S(O)$_2$—(C$_1$-C$_6$alkylene)-NR$^H$R$^J$, —N(R$^L$)S(O)$_2$—(C$_3$-C$_7$cycloalkylene)-NR$^H$R$^J$, —S(O)$_2$N(R$^L$)—(C$_2$-C$_6$alkylene)-NR$^H$R$^J$, —S(O)$_2$N(R$^L$)—(C$_3$-C$_7$cycloalkylene)-NR$^H$R$^J$, —S(O)$_2$N(R$^L$)—(C$_2$-C$_6$alkylene)-OR$^M$, —S(O)$_2$N(R$^L$)—(C$_3$-C$_7$cycloalkylene)-OR$^M$, —N(R$^L$)S(O)$_2$—(C$_2$-C$_6$alkylene)-OR$^M$, —N(R$^L$)S(O)$_2$—(C$_3$-C$_7$cycloalkylene)-OR$^M$, —S(O)$_2$N(R$^H$R$^J$), —N($R^L$)S(O)$_2R^L$, —N($R^L$)C(O)$R^L$, O$R^L$, S$R^L$, —(C$_3$-C$_7$heterocycloalkyl), (C$_5$-C$_7$heterocycloalkyl)-(C$_1$-C$_6$ alkyl), and (C$_5$-C$_7$ heterocycloalkyl)-(C$_3$-C$_6$ cycloalkyl), wherein any of such C$_1$-C$_6$alkyl, C$_3$-C$_6$cycloalkyl, —(C$_2$-C$_6$alkylene)-, —(C$_3$-C$_7$cycloalkylene)-, —(C$_3$-C$_7$heterocycloalkyl), (C$_5$-C$_7$heterocycloalkyl)-(C$_1$-C$_6$ alkyl), (C$_5$-C$_7$ heterocycloalkyl)-(C$_3$-C$_6$ cycloalkyl), and (C$_5$-C$_7$heterocycloalkyl)carbonyl portion in the above listed groups may be optionally substituted by a group C$_1$-C$_6$ alkyl, C$_3$-C$_7$ cycloalkyl, —O$R^M$, or halo.

In another embodiment, $R^{18}$ is —(C$_1$-C$_6$alkyl) or —(C$_3$-C$_7$cycloalkyl).

In one embodiment, $z^1$=—CH—, $z^2$=C, $z^3$ and $z^4$ are N; in another embodiment, $z^1$=O, $z^2$=C, $z^3$ and $z^4$ are N; in a further embodiment, $z^1$=—CH—, $z^2$ and $z^3$ are N, and $z^4$ is —CH—; in an additional embodiment, $z^1$=N, $z^2$ is C, $z^3$ is N and $z^4$ is O; in a still further embodiment, $z^1$=N, $z^2$ is C, $z^3$ is O, and $z^4$ is N.

In an additional embodiment, $R^2$ is a radical of formula (IVb):

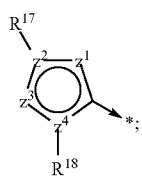
(IVb)

wherein $z^1$=O, $z^2$=C, $z^3$ is N, $z^4$ is N, $R^{18}$ is a lone pair, and $R^{17}$ is a group of general formula (V)

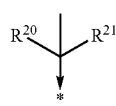
(V)

wherein $R^{20}$ is —CH$_3$ or —CH$_2$OH, and $R^{21}$ is —CH$_3$.

In another embodiment, $R^2$ is a radical of formula (IVb):

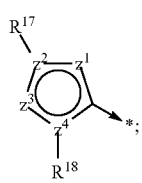
(IVb)

wherein $z^1$=N, $z^2$=C, $z^3$ is N, $z^4$ is O, $R^{18}$ is a lone pair, and $R^{17}$ is a group of formula (V)

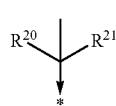
(V)

wherein $R^{20}$ is —CH$_3$ or —CH$_2$OH, and $R^{21}$ is —CH$_3$.

In an additional embodiment, $R^2$ is a radical of formula (IVb):

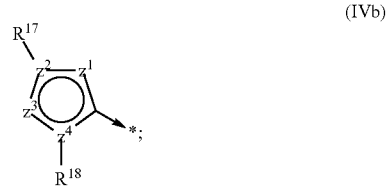
(IVb)

wherein $z^1$=—CH—, $z^2$=N, $z^3$ is N, $z^4$ is —C—, $R^{18}$ is hydrogen, and $R^{17}$ is a group of general formula (V)

(V)

wherein $R^{20}$ is —CH$_3$ or —CH$_2$OH, and $R^{21}$ is —CH$_3$.

In an additional embodiment, $R^2$ is a radical of formula (IVb):

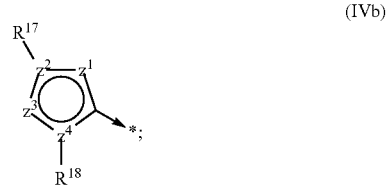
(IVb)

wherein $z^1$=—CH—, $z^2$=N, $z^3$ is N, $z^4$ is —C—, $R^{18}$ is hydrogen, and $R^{17}$ is a aryl which is optionally substituted by a group (C$_1$-C$_6$)alkyl.

In an additional embodiment, $R^2$ is a radical of formula (IVb):

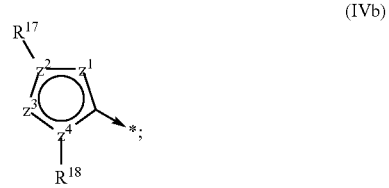
(IVb)

wherein $z^1$=—CH—, $z^2$=C, $z^3$ and $z^4$ are N and $R^{17}$ is a group of general formula (V)

(V)

wherein $R^{20}$ is —CH$_3$ or —CH$_2$OH, and $R^{21}$ is —CH$_3$.

In another embodiment, $R^2$ is a radical of formula (IVb):

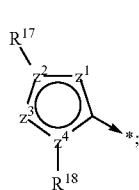

(IVb)

wherein $z^1$=—CH—, $z^2$=C, $z^3$ and $z^4$ are N and $R^{17}$ is a group of general formula (V)

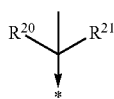

(V)

wherein $R^{20}$ is —CH$_3$ or —CH$_2$OH, $R^{21}$ is —CH$_3$ and wherein $R^{18}$ is phenyl, which is substituted by a group which is —(C$_1$-C$_6$alkylene)-NR$^H$R$^J$ or —O—(C$_2$-C$_6$alkylene)-NR$^H$R$^J$ wherein R$^H$ and R$^J$, which are not both hydrogen, are at each occurrence independently hydrogen, C$_1$-C$_6$ alkyl or C$_3$-C$_6$ cycloalkyl, wherein such C$_1$-C$_6$ alkyl or C$_3$-C$_6$ cycloalkyl is substituted by a group OR$^M$, CN, or halo; alternatively, R$^H$ and R$^J$ may form, together with the nitrogen atom to which they are attached, a 5-11 membered saturated monocyclic or bicyclic heterocyclic ring system in which the 5-11-membered saturated monocyclic or bicyclic ring is substituted by one or more groups OR$^M$, CN, halo, C$_1$-C$_6$ alkyl, or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, OR$^M$, CN, or halo; and wherein optionally, the 5-11-membered saturated monocyclic or bicyclic heterocyclic ring contains a further heteroatom which is oxygen or nitrogen, said nitrogen atom optionally substituted by C$_1$-C$_6$ alkyl or C$_3$-C$_6$ cycloalkyl, wherein any of such alkyl or cycloalkyl may be optionally substituted by a group C$_1$-C$_6$ alkyl, C$_3$-C$_7$ cycloalkyl, OR$^M$, CN, or halo;

or wherein $R^{18}$ is phenyl, which is substituted by a group (C$_5$-C$_7$heterocycloalkyl)-(C$_1$-C$_6$ alkyl), which is substituted by a group C$_1$-C$_6$ alkyl, C$_3$-C$_7$ cycloalkyl, OR$^M$, or halo;

or wherein $R^{18}$ is phenyl, which is substituted by a group C$_1$-C$_6$ alkyl which is substituted by a group C$_3$-C$_7$ cycloalkyl, —OR$^M$, or halo;

or wherein $R^{18}$ is phenyl, which is substituted by a group —CN, —O—(C$_1$-C$_6$alkyl), —NR$^H$R$^J$, —O—(C$_2$-C$_6$alkylene)-OR$^M$, —S—(C$_2$-C$_6$alkylene)-OR$^M$, —(C$_3$-C$_7$heterocycloalkyl), wherein any of such C$_1$-C$_6$alkyl, —(C$_2$-C$_6$alkylene)-, —(C$_3$-C$_7$heterocycloalkyl), portion in the above listed groups may be optionally substituted by a group C$_1$-C$_6$ alkyl, C$_3$-C$_7$ cycloalkyl, OR$^M$, or halo.

In a further embodiment, $R^2$ is a radical of formula (IVb):

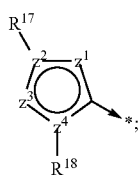

(IVb)

wherein $z^1$=—CH—, $z^2$=C, $z^3$ and $z^4$ are N and $R^{17}$ is a group of general formula (V)

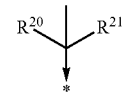

(V)

wherein $R^{20}$ is —CH$_3$ or —CH$_2$OH, and $R^{21}$ is —CH$_3$ and $R^{18}$ is heteroaryl ring which is optionally substituted by a group (C$_5$-C$_7$heterocycloalkyl)-(C$_1$-C$_6$ alkyl), which is optionally substituted by a group C$_1$-C$_6$ alkyl, C$_3$-C$_7$ cycloalkyl, OR$^M$ or halo; or $R^{18}$ is heteroaryl ring which is optionally substituted by a group —(C$_1$-C$_6$alkylene)-NR$^H$R$^J$ or —O—(C$_2$-C$_6$alkylene)-NR$^H$R$^J$.

In an additional embodiment, $R^2$ is a radical of formula (IVb):

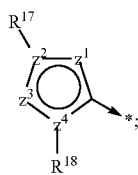

(IVb)

wherein $z^1$=—CH—, $z^2$=C, $z^3$ and $z^4$ are N and $R^{17}$ is a group of general formula (V)

(V)

wherein $R^{20}$ is —CH$_3$ or —CH$_2$OH, and $R^{21}$ is —CH$_3$ and $R^{18}$ is a group —(C$_1$-C$_6$alkyl), optionally substituted by a group —OH, halo or —NR$^H$R$^J$; or a group (C$_5$-C$_7$heterocycloalkyl) or (C$_5$-C$_7$heterocycloalkyl)-(C$_1$-C$_6$alkyl) which may be optionally substituted by a group C$_1$-C$_6$ alkyl, halo, or —OH.

In a further embodiment, $R^2$ is a radical of formula (IVc):

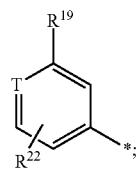

(IVc)

In one embodiment, $R^{19}$ is selected from the group consisting of: hydrogen, $-CF_3$, $-NR^ER^F$, $-(C_3-C_6cycloalkyl)$, $-(C_3-C_6heterocycloalkyl)$, aryl, and heteroaryl wherein any of such $-(C_3-C_6cycloalkyl)$, $-(C_3-C_6heterocycloalkyl)$, aryl, or heteroaryl may be optionally substituted by a group $C_1-C_2$ alkyl, $C_3-C_5$ cycloalkyl, or halo. In another embodiment, $R^{19}$ is selected from the group consisting of: hydrogen, $-CF_3$, morpholine, cyclohexyl, phenyl, or pyridyl wherein any of such morpholine, cyclohexyl, phenyl, or pyridyl may be optionally substituted by a group methyl, $-F$ or $-Cl$.

In another embodiment, $R^{19}$ is a group of general formula (V)

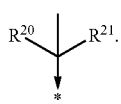

(V)

In one embodiment, T is $-N=$. In another embodiment, T is $-CR^{28}=$.

In one embodiment, $R^{22}$ is H, F, $-Cl$, $-CH_3$, or $-CN$; in another embodiment, $R^{22}$ is H or F.

In one embodiment, $R^{23}$ is H, F, $-Cl$, $-CH_3$, or $-CN$; in another embodiment, $R^{23}$ is $-Cl$.

In one embodiment, compounds of formula (IA) are provided wherein W is NH, Y is a group $-O(CR^3R^4)_n-$ and n is 0, A is group:

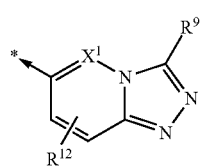

$R^1$ is a group of formula (IIb):

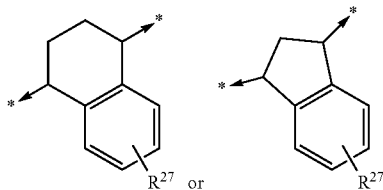

(IIb)

wherein $X^1$ is a group $-CH-$; $R^{12}$ hydrogen; $R^9$ is $C_1-C_6$ alkyl, $C_3-C_6$ cycloalkyl, phenyl which is optionally substituted, or 5- or 6-membered monocyclic heteroaryl which is optionally substituted;

$R^2$ is a radical of formula (IVb):

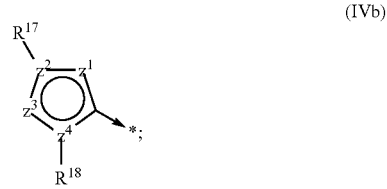

(IVb)

wherein $z^1=-CH-$, $z^2=C$, $z^3$ and $z^4$ are N and $R^{17}$ is a group of general formula (V)

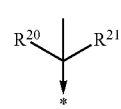

(V)

wherein $R^{20}$ is $-CH_3$ or $-CH_2OH$, and $R^{21}$ is $-CH_3$, and $R^{18}$ is a group $-(C_1-C_6alkyl)$, optionally substituted by a group $-OH$, halo or $-NR^HR^J$; or a group $(C_5-C_7heterocycloalkyl)$ or $(C_5-C_7heterocycloalkyl)-(C_1-C_6alkyl)$ which may be optionally substituted by a group $C_1-C_6$ alkyl, halo or $-OH$.

In one embodiment, compounds of formula (IB) are provided wherein W is NH, Y is a group $-O(CR^3R^4)_n-$ and n is 0, A is group:

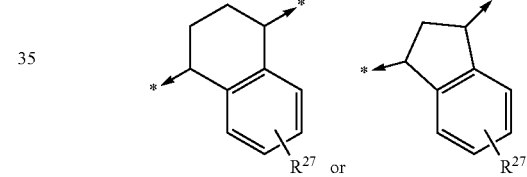

$R^1$ is a group of formula (IIb):

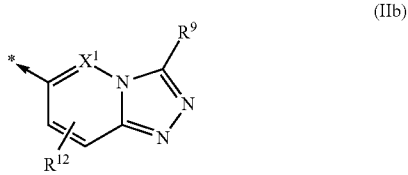

(IIb)

wherein $X^1$ is a group $-CH-$; $R^{12}$ is hydrogen; $R^9$ is $C_1-C_6$ alkyl, $C_3-C_6$ cycloalkyl, phenyl which is optionally substituted, or 5- or 6-membered monocyclic heteroaryl which is optionally substituted;

$R^2$ is a radical of formula (IVb):

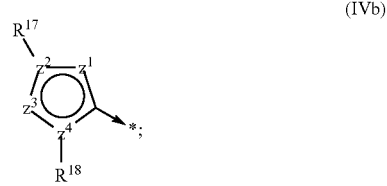

(IVb)

wherein $z^1$=—CH—, $z^2$=C, $z^3$ and $z^4$ are N and $R^{17}$ is a group of general formula (V)

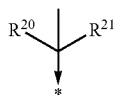

(V)

wherein $R^{20}$ is —CH$_3$ or —CH$_2$OH, and $R^{21}$ is —CH$_3$; and wherein $R^{18}$ is phenyl, which is substituted by a group which is —(C$_1$-C$_6$alkylene)-NR$^H$R$^J$ or —O—(C$_2$-C$_6$alkylene)-NR$^H$R$^J$ wherein R$^H$ and R$^J$, which are not both hydrogen, are at each occurrence independently hydrogen, C$_1$-C$_6$ alkyl or C$_3$-C$_6$ cycloalkyl, wherein such C$_1$-C$_6$ alkyl or C$_3$-C$_6$ cycloalkyl is substituted by a group OR$^M$, CN, or halo; alternatively, R$^H$ and R$^J$ may form, together with the nitrogen atom to which they are attached, a 5-11 membered saturated monocyclic or bicyclic ring system in which the 5-11-membered saturated monocyclic or bicyclic ring is substituted by one or more group OR$^M$, CN, halo, C$_1$-C$_6$ alkyl, or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, OR$^M$, CN, or halo; and wherein optionally, the 5-11-membered saturated monocyclic or bicyclic ring contains a further heteroatom which is oxygen or nitrogen, said nitrogen atom optionally substituted by C$_1$-C$_6$ alkyl or C$_3$-C$_6$ cycloalkyl, wherein any of such alkyl or cycloalkyl may be optionally substituted by a group C$_1$-C$_6$ alkyl, C$_3$-C$_7$ cycloalkyl, OR$^M$, CN, or halo;

or wherein $R^{18}$ is phenyl, which is substituted by a group (C$_5$-C$_7$heterocycloalkyl)-(C$_1$-C$_6$ alkyl), which is substituted by a group C$_1$-C$_6$ alkyl, C$_3$-C$_7$ cycloalkyl, OR$^M$, or halo;

or wherein $R^{18}$ is phenyl, which is substituted by a group C$_1$-C$_6$ alkyl which is substituted by a group C$_3$-C$_7$ cycloalkyl, —OR$^M$, or halo;

or wherein $R^{18}$ is phenyl, which is substituted by a group —CN, —O—(C$_1$-C$_6$alkyl), —NR$^H$R$^J$, —O—(C$_2$-C$_6$alkylene)-OR$^M$, —S—(C$_2$-C$_6$alkylene)-OR$^M$, —(C$_3$-C$_7$heterocycloalkyl), wherein any of such C$_1$-C$_6$alkyl, —(C$_2$-C$_6$alkylene)-, —(C$_3$-C$_7$heterocycloalkyl), portion in the above listed groups may be optionally substituted by a group C$_1$-C$_6$ alkyl, C$_3$-C$_7$ cycloalkyl, OR$^M$, or halo.

In one embodiment, a compound of formula (I) is selected from the group consisting of:

1-(5-tert-Butyl-2-(4-methoxy-phenyl)-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-2-methyl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[3-(2-hydroxyethylsulfanyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[3-(2-hydroxy-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-[1,3,4]oxadiazol-2-yl)-3-[(1S,4S)-4-(3-isopropyl-[1,2,4]triazolo[4,3-a]pyridin-6-yloxy)-1,2,3,4-tetrahydro-naphthalen-1-yl]-urea;

1-[(1S,4S)-4-(3-Isopropyl-[1,2,4]triazolo[4,3-a]pyridin-6-yloxy)-1,2,3,4-tetrahydro-naphthalen-1-yl]-3-(1-p-tolyl-1H-pyrazol-4-yl)-urea;

1-(4-Chloro-3-trifluoromethyl-phenyl)-3-[(1S,4S)-4-(3-isopropyl-[1,2,4]triazolo[4,3-a]pyridin-6-yloxy)-1,2,3,4-tetrahydro-naphthalen-1-yl]-urea;

1-(3-tert-Butyl-[1,2,4]oxadiazol-5-yl)-3-[(1S,4S)-4-(3-isopropyl-[1,2,4]triazolo[4,3-a]pyridin-6-yloxy)-1,2,3,4-tetrahydro-naphthalen-1-yl]-urea;

1-(1-tert-Butyl-1H-pyrazol-4-yl)-3-[(1S,4S)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(2-hydroxy-ethyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(4-hydroxymethyl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[3-(4,4-difluoro-piperidin-1-ylmethyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea, and 1-(5-tert-Butyl-2-{4-[2-(4-methyl-piperazin-1-yl)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

or a pharmaceutically acceptable salt thereof.

In another embodiment, a compound of formula (I) is selected from the group consisting of:

1-(5-tert-Butyl-2-(4-methoxy-phenyl)-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-2-methyl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[3-(2-hydroxyethylsulfanyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[3-(2-hydroxy-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-(5-tert-Butyl-[1,3,4]oxadiazol-2-yl)-3-[(1S,4S)-4-(3-isopropyl-[1,2,4]triazolo[4,3-a]pyridin-6-yloxy)-1,2,3,4-tetrahydro-naphthalen-1-yl]-urea;

1-[(1S,4S)-4-(3-Isopropyl-[1,2,4]triazolo[4,3-a]pyridin-6-yloxy)-1,2,3,4-tetrahydro-naphthalen-1-yl]-3-(1-p-tolyl-1H-pyrazol-4-yl)-urea;

1-(4-Chloro-3-trifluoromethyl-phenyl)-3-[(1S,4S)-4-(3-isopropyl-[1,2,4]triazolo[4,3-a]pyridin-6-yloxy)-1,2,3,4-tetrahydro-naphthalen-1-yl]-urea;

1-(3-tert-Butyl-[1,2,4]oxadiazol-5-yl)-3-[(1S,4S)-4-(3-isopropyl-[1,2,4]triazolo[4,3-a]pyridin-6-yloxy)-1,2,3,4-tetrahydro-naphthalen-1-yl]-urea;

1-(1-tert-Butyl-1H-pyrazol-4-yl)-3-[(1S,4S)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(2-hydroxy-ethyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(4-hydroxymethyl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[3-(4,4-difluoro-piperidin-1-ylmethyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea, and 1-(5-tert-Butyl-2-{4-[2-(4-methyl-piperazin-1-yl)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(4-cyano-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(4-hydroxymethyl-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea;

1-(5-tert-Butyl-2-piperidin-4-yl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(1-methyl-piperidin-4-yl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(2-morpholin-4-yl-ethyl)-2H-pyrazol-3-yl]-3-[(1S,4R)-4-(3-isopropyl[1,2,4]triazolo[4,3-a]pyridin-6-yloxy)-1,2,3,4-tetrahydro-naphthalen-1-yl]-urea;

1-(5-tert-Butyl-2-methyl-2H-pyrazol-3-yl)-3-[(1S,4R)-7-fluoro-4-(3-isopropyl-[1,2,4]triazolo[4,3-a]pyridin-6-yloxy)-1,2,3,4-tetrahydro-naphthalen-1-yl]-urea;

1-[(1S,4R)-4-(3-Isopropyl-[1,2,4]triazolo[4,3-a]pyridin-6-yloxy)-1,2,3,4-tetrahydro-naphthalen-1-yl]-3-(2-p-tolyl-2H-pyrazol-3-yl)-urea;

1-(1-tert-Butyl-1H-pyrazol-4-yl)-3-[(1S,4R)-7-fluoro-4-(3-isopropyl-[1,2,4]triazolo[4,3-a]pyridin-6-yloxy)-1,2,3,4-tetrahydro-naphthalen-1-yl]-urea;

1-(5-tert-Butyl-2-{3-[2-(4-hydroxy-piperidin-1-yl)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(3-morpholin-4-yl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[1-(2-morpholin-4-yl-ethyl)-1H-indazol-6-yl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-{5-tert-Butyl-2-[2-(2-morpholin-4-yl-ethyl)-2H-indazol-6-yl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea;

1-[5-tert-Butyl-2-(2-hydroxy-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea;

1-[5-tert-Butyl-2-(2-morpholin-4-yl-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea;

1-[5-tert-Butyl-2-(2-dimethylamino-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea;

1-[5-tert-Butyl-2-(2-piperidin-1-yl-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea;

1-{5-tert-Butyl-2-[2-(4-methyl-piperazin-1-yl)-ethyl]-2H-pyrazol-3-yl}-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea;

1-[5-tert-Butyl-2-(2-hydroxy-ethyl)-2H-pyrazol-3-yl]-3-{(1S,4R)-4-[3-(2-chloro-phenyl)-[1,2,4]triazolo[4,3-a]pyridin-6-yloxy]-1,2,3,4-tetrahydro-naphthalen-1-yl}-urea;

1-[5-tert-Butyl-2-(2-morpholin-4-yl-ethyl)-2H-pyrazol-3-yl]-3-{(1S,4R)-4-[3-(2-chloro-phenyl)-[1,2,4]triazolo[4,3-a]pyridin-6-yloxy]-1,2,3,4-tetrahydro-naphthalen-1-yl}-urea;

1-(5-tert-Butyl-2-methyl-2H-pyrazol-3-yl)-3-{(1S,4R)-4-[3-(2,6-dichlorophenyl)-[1,2,4]triazolo[4,3-a]pyridin-6-yloxy]-1,2,3,4-tetrahydronaphthalen-1-yl]-urea;

1-[5-tert-Butyl-2-(2-morpholin-4-yl-ethyl)-2H-pyrazol-3-yl]-3-[(1S,4R)-4-(3-cyclohexyl-[1,2,4]triazolo[4,3-a]pyridin-6-yloxy)-1,2,3,4-tetrahydro-naphthalen-1-yl]-urea;

1-(5-tert-Butyl-2-(3-hydroxy-propyl)-2H-pyrazol-3-yl)-3-{(1S,4R)-4-[3-(2,6-dichlorophenyl)-[1,2,4]triazolo[4,3-a]pyridin-6-yloxy]-1,2,3,4-tetrahydronaphthalen-1-yl]-urea;

or a pharmaceutically acceptable salt thereof.

Utility.

As mentioned above the compounds of the present invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides methods for prevention and/or treatment of any disease which benefit from inhibition of the p38 enzyme, said method comprises administering to a patient in need of such treatment a therapeutically effective amount of a compound of the invention.

Compositions.

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebulizer or as an aerosol in a liquid propellant, for example for use in a pressurized metered dose inhaler (PMDI). Propellants suitable for use in a PMDI are known to the skilled person, and include CFC-12, HFA-134a, HFA-227, HCFC-22 ($CCl_2F_2$), and HFA-152 ($CH_4F_2$ and isobutane).

In a preferred embodiment of the present invention, a composition of the present invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, an example is:

| Compound of the invention | 24 mg/canister |
|---|---|
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321, which is incorporated herein by reference in its entirety). Additionally, compounds of the invention may be delivered in multi-chamber devices thus allowing for delivery of combination agents.

Combinations.

Other compounds may be combined with compounds with which the invention is concerned for the prevention and treatment of inflammatory diseases, in particular respiratory diseases. Thus, the present invention is also concerned with pharmaceutical compositions comprising a therapeutically effective amount of a compound of the present invention and one or more other therapeutic agents. Suitable therapeutic agents for a combination therapy with compounds of the present invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, and TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, and AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, formoterol/beclometasone dipropionate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, and arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028, and EP-101; (5) dual pharmacology M3-anticholinergic/β2-adrenoreceptor agonists such as GSK961081, AZD2115, and LAS190792; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, and AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, and GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723, or selective histamine-4 (H4) receptor antagonists, such as ZPL3893787; (9) antitussive agents, such as codeine or dextramorphan; (10) a mucolytic, for example N-acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin, and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO 97/03094 and WO 97/02289, which are incorporated herein by reference in their entireties; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO 2005/026124, WO 2003/053930, and WO 2006/082412, which are incorporated herein by reference in their entireties; (20) A2b antagonists such as those described in WO 2002/42298, which is incorporated herein by reference in its entirety; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and OC000459 and AZD1981 and mixed DP1/CRTH2 antagonists such as AMG 009 and AMG853; (23) PPAR agonists including PPAR alpha agonists (such as fenofibrate), PPAR delta agonists, PPAR gamma agonists such as Pioglitazone, Rosiglitazone, and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate, and theophylline/beclometasone dipropionate; (25) A2a agonists such as those described in EP 1 052 264 and EP 1 241 176, which are incorporated herein by reference in their entireties; (26) CXCR2 or IL-8 antagonists such as SCH 527123 or GSK 656933; (27) IL-R signalling modulators such as kineret and ACZ 885; (28) MCP-1 antagonists such as ABN-912.

The present invention is also directed to kits comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler or a nebulizer.

Methods of Synthesis.

In one aspect of the present invention, a process for the preparation of compounds of the invention is provided, according to general synthetic routes described in this section. In the following reaction schemes, unless otherwise indicated, the groups mentioned assume the same meaning as those reported for compounds of formula (I).

The skilled person may introduce, where appropriate, suitable variations to the conditions specifically described in the examples in order to adapt the synthetic routes to the provision of further compounds of the invention. Such variations may include, but are not limited to, use of appropriate starting materials to generate different compounds, changes in the solvent and temperature of reactions, replacement of reactants with analogous chemical role, introduction or removal of protection/deprotection stages of functional groups sensitive to reaction conditions and reagents, as well as introduction or removal of specific synthetic steps oriented to further functionalization of the chemical scaffold.

Processes which can be used and are described and reported in Examples and Schemes, should not be viewed as limiting the scope of the synthetic methods available for the preparation of the compounds of the invention.

The process described is particularly advantageous as it is susceptible of being properly modulated, through any proper variant known to the skilled person, so as to obtained any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981), which is incorporated herein by reference in its entirety).

Likewise, selective protection and deprotection of any of the said groups, for instance including carbonyl, hydroxyl, or amino groups, may be accomplished according to very well known methods commonly employed in organic synthetic chemistry.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

For example, compounds of the present invention of formula (I) may be prepared according to the route illustrated in Scheme 1:

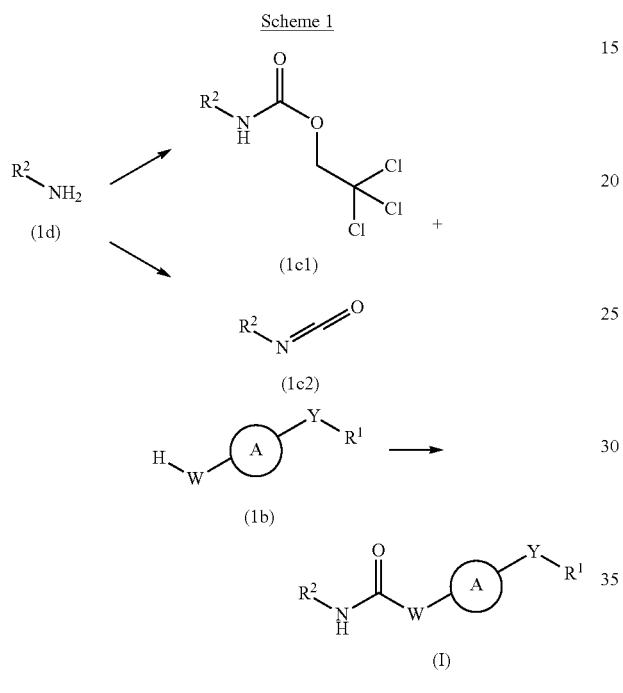

Compounds of general formula (I) may be prepared from compounds of general formula (1b) by reaction with a compound of general formula (1c1) or (1c2) in a suitable solvent such as dimethyl sulfoxide, 1,4-dioxane, DMF, or acetonitrile, in the presence of a base such as diisopropylethylamine or sodium hydroxide at a range of temperatures, preferably between room temperature and 100° C.

Compounds of general formula (1c1) and (1c2) are either known in the literature or may be prepared from amines of general formula (1d) according to known literature procedures (e.g. WO 2006/009741, EP 1 609 789, WO 2008/033999, which are incorporated herein by reference in their entireties).

Alternatively, Compounds of general formula (1d) are either known in the literature or may be synthesized by one skilled in the art by adapting appropriate literature methods (e.g. WO 201/0077836, WO 2006/009741, WO 2008/125014, J. Med. Chem., 2007, 50, 4016, Bulletin des Societes Chimiques Belges, 1987, 96, 675-709, Organic & Biomolecular Chemistry, 2006, 4, 4158-4164, which are incorporated herein by reference in their entireties).

Compounds of general formula (1da), i.e. compounds of formula (1d) wherein $R^2$ is a group of formula (IVb) and $R^{17}$, $R^{18}$, $z^1$, $z^2$, $z^3$ and $z^4$ are as defined above can be prepared from compounds of formula (1e):

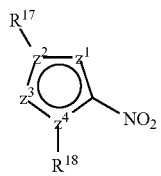

using a suitable reducing agent such as tin (II) chloride, iron, or hydrogen gas with a suitable catalyst such as palladium on carbon, in a suitable solvent such as methanol, ethanol, or acetic acid, at a range of temperatures, preferably between room temperature and 100° C.

Compounds of general formula (1e) are known in the literature or may be prepared by those skilled in the art using literature methods (e.g. WO 2008/034008, WO 2011/0189167, WO 2010/068258, which are incorporated herein by reference in their entireties).

Alternatively, compounds of general formula (1da) as above defined can be prepared from compounds of formula (1f), wherein $R^{17}$, $R^{18}$, $z^1$, $z^2$, $z^3$ and $z^4$ are as defined above and wherein PG is a suitable compatible protecting group known to those skilled in the art, such as benzyl, benzyl carbamate or tert-butyl carbamate:

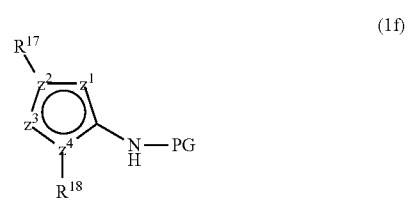

using suitable deprotection conditions such as hydrochloric acid, trifluoroacetic acid, or hydrogen catalysed by for example palladium on carbon, in a suitable solvent such as dichloromethane, methanol, ethanol or acetic acid, at a range of temperatures, preferably between 0° C. and 100° C.

Compounds of general formula (1f) can be prepared by reaction of compounds of formula (1g) shown below, wherein $R^{17}$, $R^{18}$, $z^1$, $z^2$, $z^3$ and $z^4$ are as defined above

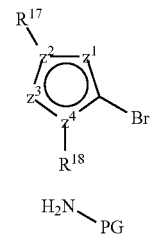

with compounds of formula (1h) as shown above wherein PG is a suitable protecting group known to those skilled in the art, such as benzyl, benzyl carbamate, or tert-butyl carbamate, using suitable conditions such as in the presence of a base such as potassium carbonate or diisopropylethyl amine or under Buchwald conditions (with a catalyst such as Pd(OAc)$_2$, a ligand such as 2,2'-bis(diphenylphosphino)-1,1'-binaphthyl and base such as sodium tert-butoxide), in a suitable solvent such as toluene or tetrahydrofuran, at a range of temperatures, preferably between room temperature and 150° C.

Compounds of general formula (1g) and (1h) are known in the literature or may be prepared by those skilled in the art by adapting appropriate literature methods (e.g. WO 2011/042389, Chemistry-A European Journal, 2011, 17, 6606-6609, S6606/1-S6606/38, which are incorporated herein by reference in their entireties).

Compounds of general formula (Ib), may be prepared according to the route illustrated in Scheme 2.

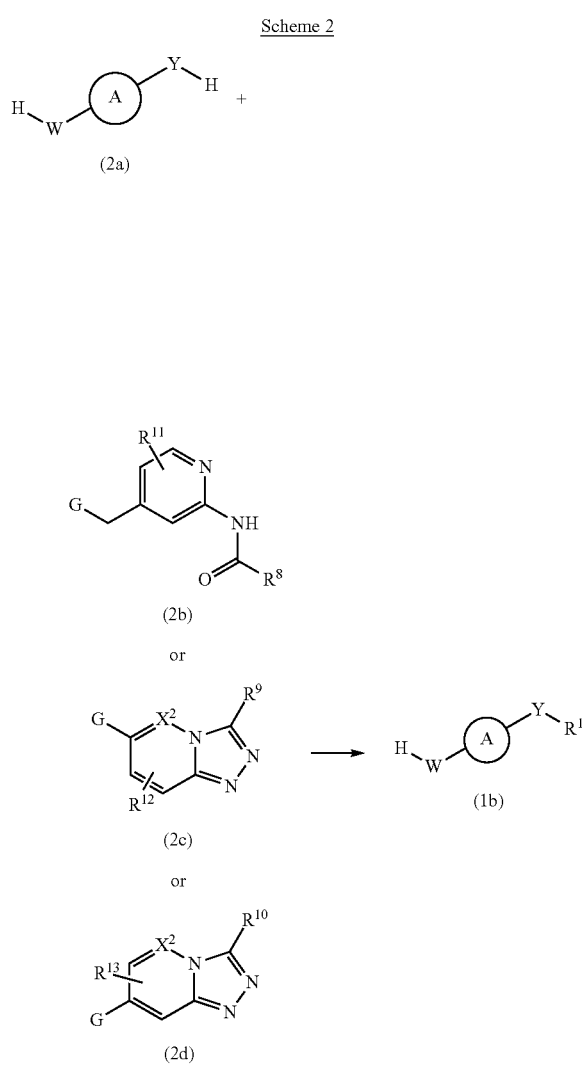

Compounds of general formula (1b) may be prepared from compounds of general formula (2a) by reaction with a compound of general formula (2b), (2c) or (2d), wherein G is a suitable chemical group known to those skilled in the art selected such that it can facilitate a suitable coupling reaction such as nucleophilic displacement or metal catalysed cross coupling. For example, in cases such that when Y is —O—, —S— or —NR$^7$—, examples of G may include halogen or a suitable leaving group such as mesylate or triflate either directly linked or attached via a group —(CR$^3$R$^4$)$_n$—. Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between room temperature and 150° C. For example, in cases such that when Y is —O— and G is —OH or —SH, a method to perform this coupling may involve Mitsunobu conditions (diethylazodicarboxylate/triphenylphosphine) in a suitable solvent such as tetrahydrofuran or 1,4-dioxane at a range of temperatures preferably between −10° C. and 100° C. For example, in cases such as when Y is —O—, —S— or —NR$^7$— and G is a group such as halogen, triflate or boronic acid/ester, a method to perform this coupling may be under metal (for example palladium or copper) catalyzed coupling conditions in the presence of a suitable ligand such as Xantphos or 1,10-phenanthroline in the presence of a base such as caesium carbonate in a suitable solvent such as tetrahydrofuran, 1,4-dioxane, or N,N-dimethylformamide at a range of temperatures preferably between −10° C. and 150° C. For example, in cases such as when Y is —O— and G is a group such as —COOMe, —COOH, isocyanate, —OCOCl or —NHCOOCH$_2$CCl$_3$, examples of conditions to perform this coupling may involve the use of a base such as sodium hydride or triethylamine or a coupling reagent such as HATU in a suitable solvent such as dichloromethane, tetrahydrofuran, 1,4-dioxane, or N,N-dimethylformamide at a range of temperatures preferably between −10° C. and 150° C.

Compounds of formula (2b) are known in the literature or may be prepared by those skilled in the art by adapting appropriate literature methods (e.g. WO 2006,133006, which is incorporated herein by reference in its entirety).

Compounds of formula (2c) may be prepared according to the route in Scheme 3:

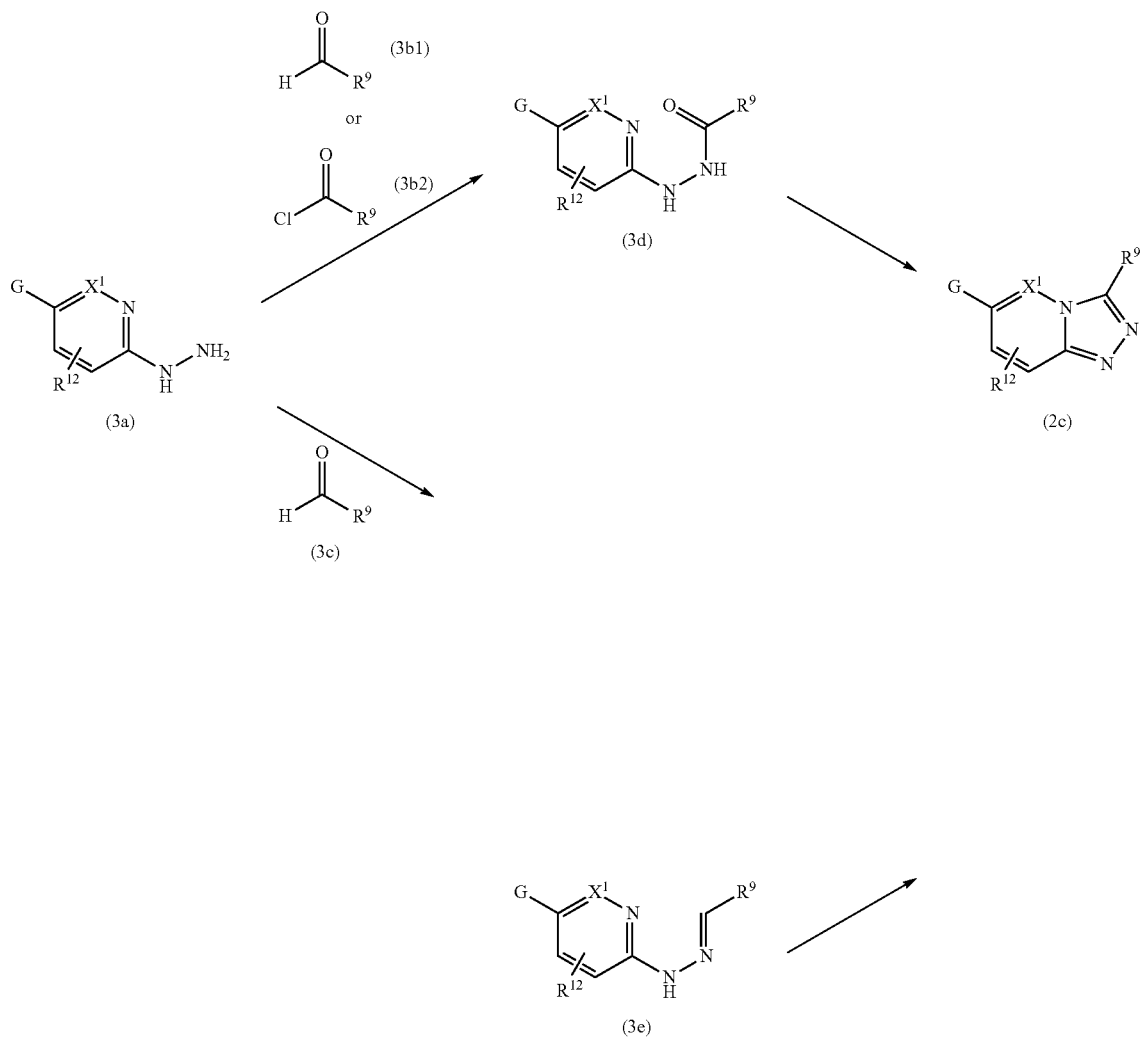

Compounds of general formula (2c) may be prepared from compounds of general formula (3e) as shown above using a suitable oxidant such as chloramine T, lead tetracetate or phenyliodine(III) diacetate, in a suitable solvent such as dichloromethane or ethanol at a range of temperatures, preferably between room temperature and 100° C.

Compounds of general formula (3e) may be prepared from compounds of general formula (3a) by reaction with an aldehyde of general formula (3c) in a suitable solvent such as ethanol or tetrahydrofuran at a range of temperatures, preferably between room temperature and 80° C.

Compounds of formula (3a) and (3c) are known in the literature or may be prepared by literature methods by those skilled in the art.

Alternatively, compounds of formula (2c) may be prepared from compounds of formula (3d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene, or NMP, at a range of temperatures, preferably between room temperature and 120° C.

Compounds of formula (3d) may be prepared from compounds of formula (3a) by reaction with a compound of general formula (3b1) using a suitable acylating/dehydrating agent such as triphenylphosphine/trichloroacetonitrile/HOBt/2-(7-aza-1H-benzotriazole-1-yl)-1,1,3,3-tetramethyluronium hexafluorophosphate or 1-ethyl-3-(3-dimethylaminopropyl)carbodiimide in the presence of a base such as diisopropylethylamine, in a suitable solvent such as dichloromethane or acetonitrile, at a range of temperatures, preferably between room temperature and 150° C.

Alternatively, compounds of formula (3d) may be prepared from compounds of formula (3a) by reaction with a compound of general formula (3b2) in the presence of a base such as diisopropylethylamine, in a suitable solvent such as dichloromethane or THF at a range of temperatures preferably between −10° C. and the boiling point of the solvent.

Compounds of formulae (3b1) and (3b2) are known in the literature or may be prepared by adapting appropriate literature methods by those skilled in the art.

Compounds of formula (2d) may be prepared according to the route in Scheme 4:

Scheme 4

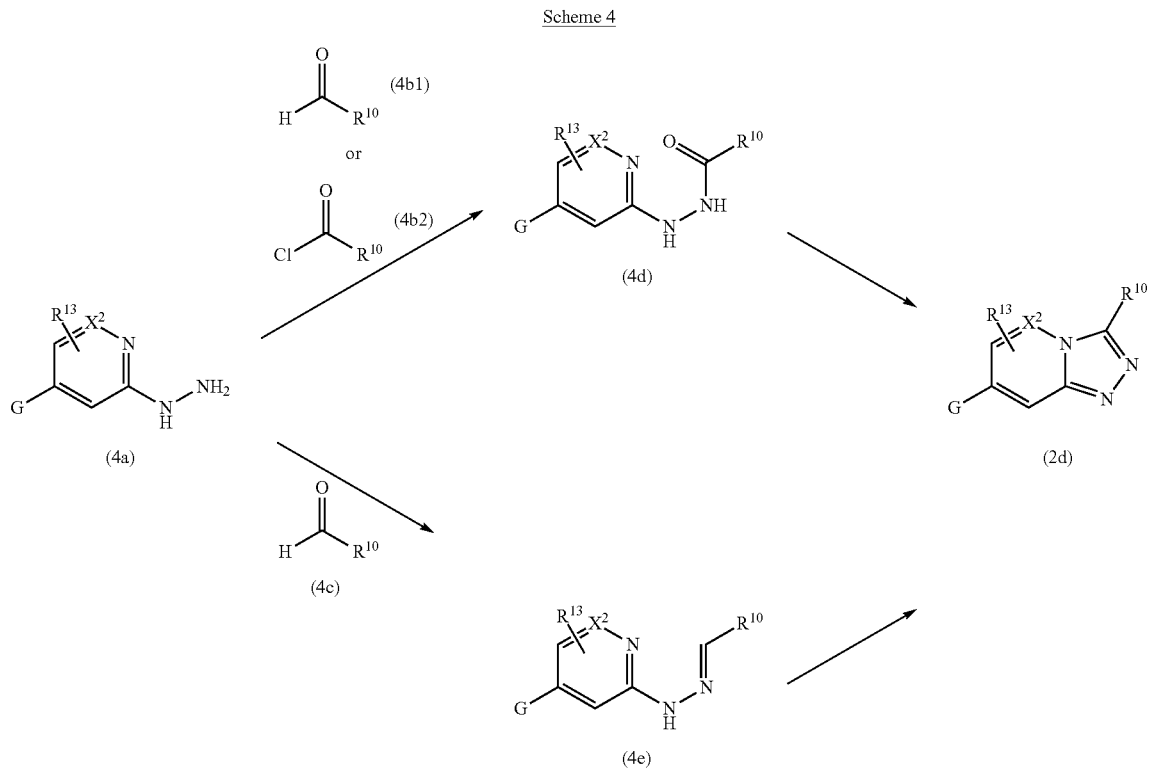

Compounds of general formula (2d) may be prepared from compounds of general formula (4e) using a suitable oxidant such as chloramine T, lead tetracetate, or phenyliodine(III) diacetate, in a suitable solvent such as dichloromethane or ethanol at a range of temperatures, preferably between room temperature and 100° C.

Compounds of general formula (4e) may be prepared from compounds of general formula (4a) by reaction with an aldehyde of general formula (4c) in a suitable solvent such as ethanol or tetrahydrofuran at a range of temperatures, preferably between room temperature and 80° C.

Compounds of formula (4a) and (4c) are known in the literature or may be prepared by literature methods by those skilled in the art.

Alternatively, compounds of formula (2d) may be prepared from compounds of formula (4d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene, or NMP, at a range of temperatures, preferably between room temperature and 120° C.

Compounds of formula (4d) may be prepared from compounds of formula (4a) by reaction with a compound of general formula (4b1) using a suitable acylating/dehydrating agent such as triphenylphosphine/trichloroacetonitrile/HOBt/2-(7-aza-1H-benzotriazole-1-yl)-1,1,3,3-tetramethyluronium hexafluorophosphate or 1-ethyl-3-(3-dimethylaminopropyl)carbodiimide in the presence of a base such as diisopropylethylamine, in a suitable solvent such as dichloromethane or acetonitrile, at a range of temperatures, preferably between room temperature and 150° C.

Alternatively, compounds of formula (4d) may be prepared from compounds of formula (4a) by reaction with a compound of general formula (4b2) in the presence of a base such as diisopropylethylamine, in a suitable solvent such as dichloromethane or THF at a range of temperatures preferably between −10° C. and the boiling point of the solvent.

Compounds of formulae (4b1) and (4b2) are known in the literature or may be prepared by adapting appropriate literature methods by those skilled in the art.

Alternatively, compounds of formula (2c) may be prepared according to the route in Scheme 5:

Scheme 5

(3a) → 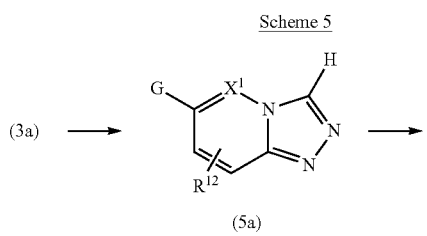 →

(5a)

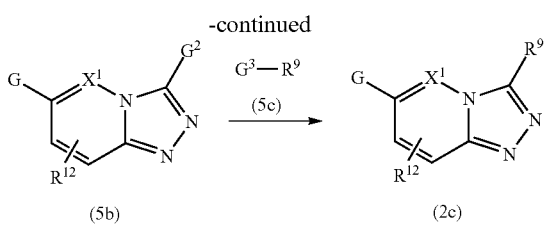

Compounds of general formula (2c) may be prepared by reaction of compounds of general formula (5b) wherein, $G^2$ is a group such as a halogen, with compounds of general formula (5c) wherein $G^3$ is a group such as a halogen, boronic acid, boronic ester, or organo stannane, using a cross-coupling method such as that using a suitable catalyst such as tetrakis(triphenylphosphine)palladium (0) or palladium (II) acetate, in the presence of a base such as caesium carbonate or sodium tert-butoxide, in a suitable solvent such as toluene or DMF at a range of temperatures, preferably between room temperature and 150° C.

Compounds of formula (5b) can be prepared from compounds of general formula (5a) using for example a suitable halogenating agent such as N-bromosuccinimide or N-iodosuccinimide, in a solvent such as DMF or tetrahydrofuran at a range of temperatures, preferably between room temperature and 100° C.

Compounds of formula (5a) may be prepared from compounds of general formula (3a) using a reagent such as triethylorthoformate, in absence or the presence of a solvent such as, ethanol, under neutral, basic or acidic conditions at a range of temperatures preferably room temperature to 100° C. Compounds of formula (3a) can be prepared as described above.

It will be appreciated that the methods described in Scheme 5 can be adapted by those skilled in the art to provide compounds of formula (2d) using compounds of formula (4a).

Compounds of general formula (2aa), i.e. compounds of formula (2a) wherein Y=O and W=NH may be prepared according to the route illustrated in scheme 6:

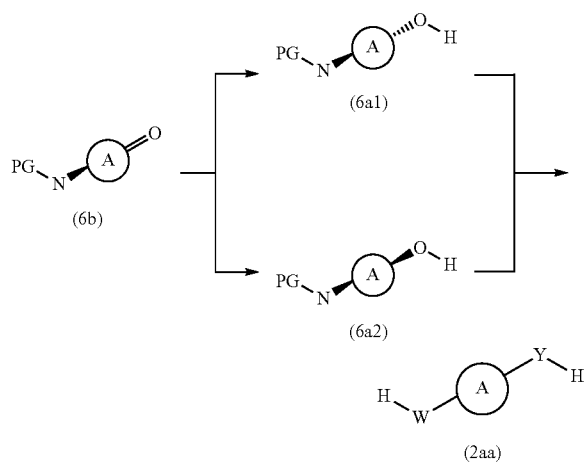

For example, compounds of general formula (2aa) may be prepared as described in WO 2008/043019, which is incorporated herein by reference in its entirety. Compounds of general formula (2aa) may be prepared from compounds of general formula (6a1) or (6a2) wherein PG is a suitable protecting group (such as trifluoroacetate or tert-butyl carbamate) known to those skilled in the art using suitable deprotection conditions such as sodium hydroxide in methanol and water or trifluoroacetic acid in dichloromethane.

Compounds of general formulae (6a1) and (6a2) may be prepared from compounds of general formula (6b).

Compounds of general formula (6a1), wherein PG is an amide, preferably trifluoroacetamide, may be prepared from compounds of general formula (6b) as described in WO 2008/043019, which is incorporated herein by reference in its entirety, using RuCl[S,S-Tsdpen(p-cymene)].

Compounds of general formula (6a2), wherein PG is an amide, preferably trifluoroacetamide, may be prepared from compounds of general formula (6b) as described in WO 2008/043019, which is incorporated herein by reference in its entirety, using RuCl[R,R-Tsdpen(p-cymene)]. It will be recognised that compounds of formula (6b) may be homochiral as illustrated or be the opposite enantiomer or racemic.

It will be realized by those skilled in the art that any combination of stereocentres in (2a) can be prepared using both enantiomers of (6b) and using RuCl[R,R-Tsdpen(p-cymene)] or RuCl[S,S-Tsdpen(p-cymene)]. Compound (2aa) is drawn with no defined stereocenters but any combination thereof can be obtained as illustrated in Scheme 2.

Compounds of formula (6b) can be prepared from compounds of formula (6c)

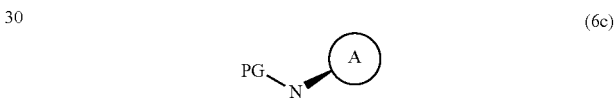

using a suitable oxidant such as potassium permanganate and magnesium sulfate in a suitable solvent methanol/water at a range of temperatures preferably between room temperature and the boiling point of the solvent. It will be recognized that compounds of formula (6c) may be homochiral as illustrated or be the opposite enantiomer or racemic.

Compounds of formula (6c) can be prepared from compounds of formula (6d) where PG is a suitable protecting group such as trifluoroacetate or tert-butyl carbonate:

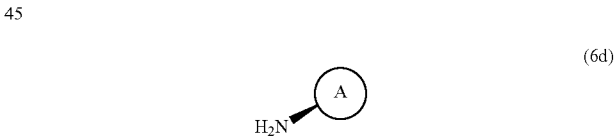

using ethyl trifluoroacetate or di-tert-butyl dicarbonate in the presence of base such as triethylamine or diisopropylethylamine in a solvent such as methanol or dichloromethane at a range of temperatures preferably between 0° C. and the boiling point of the solvent. It will be recognized that compounds of formula (6d) may be homochiral as illustrated or be the opposite enantiomer or racemic.

Compounds of formula (6d) are known in the literature and may be prepared by those skilled in the art by adapting literature methods (e.g. for S-(+)-1-amino-1,2,3,4-tetrahydronaphthalene, see Journal of the Chemical Society, Perkin Transactions 1: 1985, 2039-44; for (S)-(+)-8-amino-5,6,7,8-tetrahydroquinoline, see Journal of Organic Chemistry, 2007, 72, 669-671; and for 1-aminoindan, see Tetrahedron Letters, 2011, 52, 1310-1312, which are incorporated herein by reference in their entireties)

Compounds of formula (Ib), i.e. compounds of formula (1) where $Y=NR^7$ and $W=NH$ and A, $R^1$, $R^2$, and $R^7$ are as defined above, may be prepared, according to the route illustrated in Scheme 7.

facilitate a reaction such as a nucleophilic displacement, for example a halogen or an oxygen atom which has a suitable substituent such as mesylate or triflate, by using a suitable base such as diisopropylethylamine or potassium carbonate

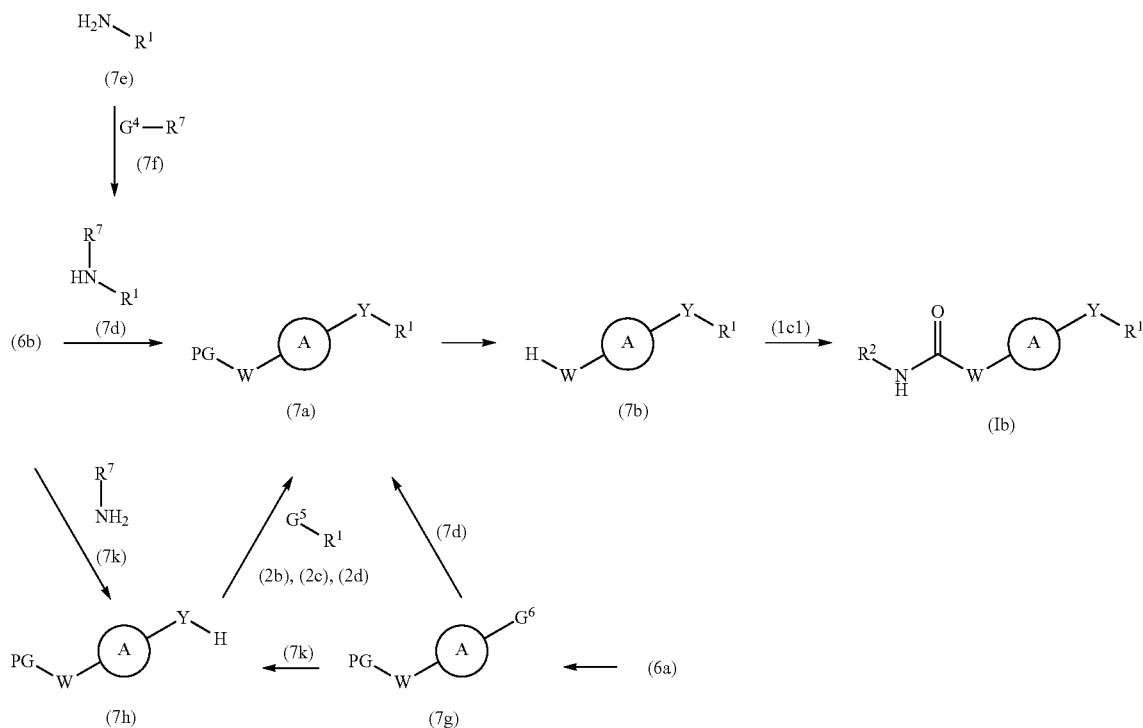

Scheme 7

Compounds of general formula (Ib) as above defined may be prepared from compounds of general formula (7b), where $Y=NR^7$ and $W=NH$ by reaction with a compound of general formula (1c1) in a suitable solvent such as dimethyl sulfoxide, 1,4-dioxane, DMF or acetonitrile, in the presence of a base such as diisopropylethylamine or sodium hydroxide at a range of temperatures, preferably between 0° C. and 100° C.

Compounds of general formula (7b) may be prepared from compounds of general formula (7a), where $Y=NR^7$ and $W=NH$ and wherein PG is a suitable protecting group such as trifluoroacetamide, tert-butyl carbamate or benzyl carbamate using suitable deprotection conditions such as, sodium hydroxide in methanol, trifluoroacetic acid in dichloromethane or hydrogen catalysed by for example palladium on carbon in ethanol, at a range of temperatures, preferably between 0° C. and 100° C.

Compounds of general formula (7a), may be prepared from compounds of general formula (7d) and (6b) using a suitable reducing agent such as sodium triacetoxyborohydride or sodium borohydride in a suitable solvent such as 1,2-dichloroethane, methanol or acetic acid, at a range of temperatures, preferably between 0° C. and 100° C.

Alternatively, compounds of general formula (7a), may be prepared from compounds of general formulae (7d) and (7g), wherein PG is a suitable protecting group known to those skilled in the art, such as trifluoroacetamide, tert-butyl carbamate and benzyl carbamate and $G^6$ is a suitable chemical group known to those skilled in the art selected such that it can in a suitable solvent such as DMF, tetrahydrofuran or acetonitrile at a range of temperatures, preferably between 0° C. and 100° C.

Compounds of formula (7g) can be prepared from compounds of formula (6a) using conditions such as carbon tetrabromide and triphenylphosphine or methanesulfonyl chloride and diisopropylethylamine, in a suitable solvent such as dichloromethane or acetonitrile at a range of temperatures, preferably between 0° C. and 100° C.

Alternatively, compounds of formula (7a) may be prepared from compounds of general formula (7h) by reaction with (2b), (2c) and (2d), in the optional presence of a catalyst such as copper (I) iodide or tris(dibenzylideneacetone)dipalladium(0), in the optional presence of a ligand such as 2,2'-bis (diphenylphosphino)-1,1'-binaphthyl, using a base such as diisopropylethyl amine, sodium tert-butoxide or sodium hydride in a solvent such as DMF, toluene or tetrahydrofuran at a range of temperatures preferably between room temperature and 150° C.

Compounds of formula (7h) can be prepared from compounds of formula (7k) by reaction with compounds of formula (6b); wherein PG is a suitable protecting group known to those skilled in the art, such as trifluoroacetamide, tertbutyl carbamate and benzyl carbamate, by using a suitable reducing agent such as sodium triacetoxyborohydride or sodium borohydride in a suitable solvent such as 1,2-dichloroethane, methanol or acetic acid, at a range of temperatures, preferably between 0° C. and 100° C.

Alternatively, compounds of formula (7h) can be prepared from compounds of formula (7k) using compounds of formula (7g); wherein PG is a suitable protecting group known to those skilled in the art, such as trifluoroacetamide, tert-butyl carbamate and benzyl carbamate and $G^6$ is a suitable chemical group known to those skilled in the art selected such that it can facilitate a nucleophilic displacement reaction, such as a halogen or an oxygen atom which has a suitable substituent such as mesylate or triflate, by using a suitable base such as diisopropylethylamine or potassium carbonate in a suitable solvent such as DMF, tetrahydrofuran or acetonitrile at a range of temperatures, preferably between 0° C. and 100° C.

Compounds of general formula (7d), may be prepared from compounds of general formula (7e) and (7f) wherein $G^4$ is a suitable chemical group known to those skilled in the art selected such that it can facilitate a nucleophilic displacement reaction, such as a halogen or an oxygen atom which has a suitable substituent such as mesylate or triflate, by using a suitable base such as diisopropylethylamine or potassium carbonate in a suitable solvent such as DMF, tetrahydrofuran or acetonitrile at a range of temperatures, preferably between 0° C. and 100° C.

Compounds of formula (7e) and (7f) are known in the literature or may be prepared by those skilled in the art using literature procedures (e.g. Organic Letters, 2002, 4, 3423-3426, which is incorporated herein by reference in its entirety).

Compounds of formula (1ba), i.e. compounds of formula (1b) where $Y=(CR^5R^6)_n$ and $W=NH$, may be prepared according to the route illustrated in Scheme 8.

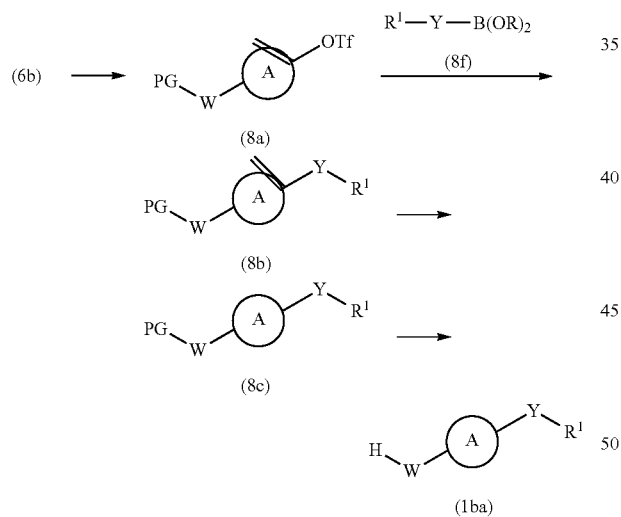

Compounds of formula (1ba) may be prepared from compounds of formula (8c) wherein PG is a suitable protecting group known to those skilled in the art, such as trifluoroacetamide, tert-butyl carbamate and benzyl carbamate by using suitable deprotection conditions such as, sodium hydroxide in methanol, trifluoroacetic acid in dichloromethane or hydrogen gas catalysed by for example palladium on carbon in ethanol, at a range of temperatures, preferably between 0° C. and 100° C.

Compounds of formula (8c) may be prepared from compounds of formula (8b) wherein PG is a suitable protecting group known to those skilled in the art, such as trifluoroacetamide, tert-butyl carbamate, and benzyl carbamate by using hydrogen gas in the presence of a catalyst such as palladium on carbon, in a suitable solvent such as methanol or ethanol, in the presence or absence of an acid such as HCl, at a range of temperatures, preferably between 0° C. and 100° C.

Compounds of formula (8b) may be prepared from compounds of formula (8a) and (8f) by a reaction such as a cross-coupling using a suitable catalyst such as tetrakis(triphenylphosphine)palladium (0) or palladium acetate, and a base such as diisopropylethylamine, sodium tert-butoxide or caesium carbonate in a suitable solvent such as NMP, toluene, or DMF, at a range of temperatures, preferably between 0° C. and 100° C. Alternatively (8b) may be prepared by adapting literature procedures (e.g. those reported in WO 2009/022633, which is incorporated herein by reference in its entirety).

Compounds of formula (8f) are known in the literature or may be prepared by those skilled in the art by adapting literature procedures (e.g. WO 2008/063287, which is incorporated herein by reference in its entirety).

Compounds of formula (8a) may be prepared from compounds of formula (6b) using a triflating agent such as triflic anhydride, in the presence of a suitable base such as pyridine or 2,6-bis(tert-butyl)-4-methylpyridine, in a solvent such as dichloromethane or chloroform at a range of temperatures, preferably between 0° C. and boiling point of the solvent. Alternatively (8a) may be prepared by adapting literature procedures (e.g. those described in WO 2009/022633, which is incorporated herein by reference in its entirety).

Compounds of the invention of formula (Id), i.e. compound of formula (1) where $Y=O$ and $W=O$ and $R^1$, $R^2$ and A are as defined above, may be prepared, according to the route illustrated in Scheme 9.

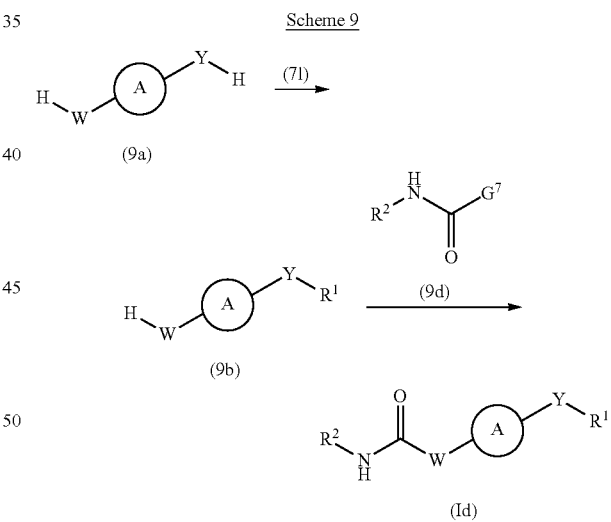

Compounds of general formula (Id) may be prepared from compounds of general formula (9b) where $Y=O$ and $W=O$ and (9d) wherein $G^7$ is a suitable chemical group such as a halogen or alkoxy, using a suitable base such as diisopropylethylamine, potassium carbonate, or sodium hydride in a suitable solvent such as DMF, tetrahydrofuran, or acetonitrile at a range of temperatures, preferably between 0° C. and 100° C.

Compound of formula (9b) can be prepared from compounds of formula (9a) and (2b), (2c), or (2d). Compounds of formula (9a) are known in the literature and can be prepared by those skilled in the art by adapting literature methods (e.g.

Angewandte Chemie, International Edition, 2006, 45, 98-101 and Chimia, 2007, 61, 169-171, which are incorporated herein by reference in their entireties).

Compounds of formula (9d) are known in the literature and can be prepared by those skilled in the art using literature methods. Alternatively, compounds of formula (9d) can be prepared from compounds of formula (1d) using alkyl chloroformate, dialkyl anhydride or phosgene in the optional presence of a base such as sodium hydroxide or diisopropylethylamine in a solvent such as dichloromethane, dioxane, or tetrahydrofuran at a range of temperatures preferably between 0° C. and the boiling point of the solvent.

Compounds of the invention of formula (Ie), i.e. compounds of formula (I) wherein Y=S and W=NH, may be prepared according to the route illustrated in scheme 10:

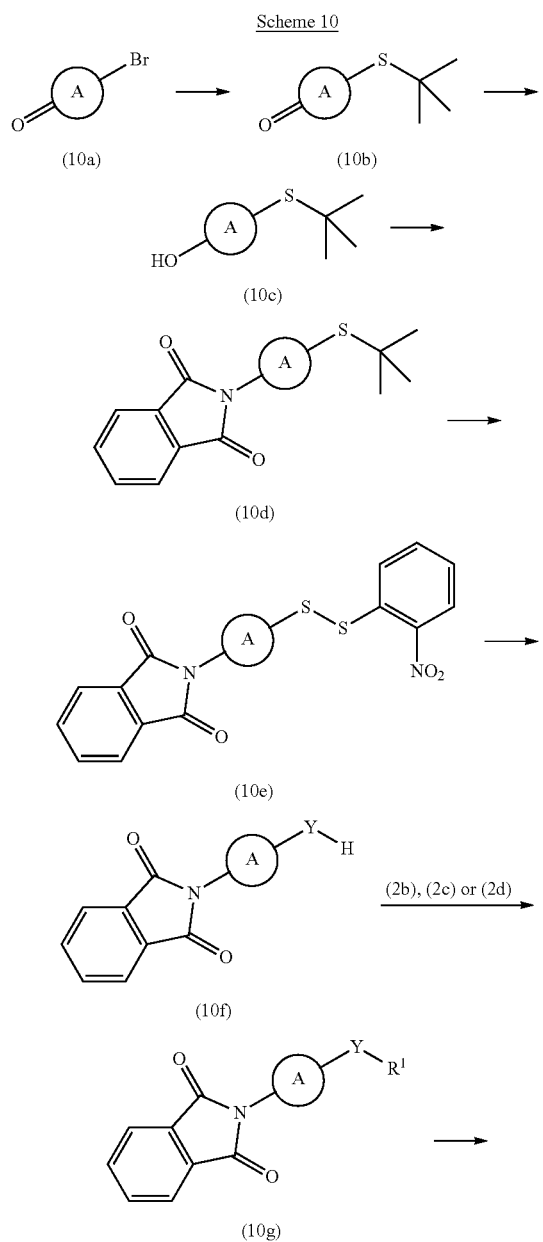

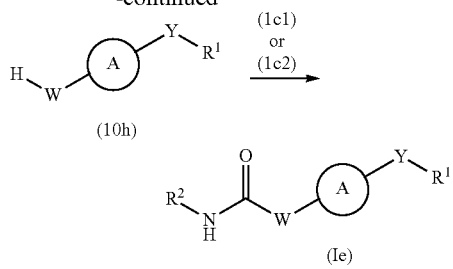

Compounds of general formula (Ie) may be prepared from compounds of general formula (10h), wherein Y=S and W=NH: using compounds of formula (1c1) or (1c2) in a suitable solvent such as dimethyl sulfoxide, 1,4-dioxane, N,N-dimethylformamide, or acetonitrile, in the presence of a base such as diisopropylethylamine at a range of temperatures, preferably between room temperature and 100° C.

Compounds of formula (10h) wherein Y=S and W=NH may be prepared from compounds of formula (10g) using deprotection conditions such as hydrazine in methanol at a range of temperatures preferably between room temperature and the boiling point of the solvent.

Compounds of formula (10g) wherein Y=S, can be prepared from compounds of formula (100f) by reaction with compounds of formulae (2b), (2c) or (2d). Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane, or acetonitrile at a range of temperatures, preferably between room temperature and 150° C. Alternative methods to perform this coupling may involve Mitsunobu conditions (diethylazodicarboxylate/triphenylphosphine) or metal (for example palladium) catalysed coupling conditions in a suitable solvent such as tetrahydrofuran or 1,4-dioxane at a range of temperatures preferably between −10° C. and 150° C.

Compounds of formula (10f) can be prepared from compounds of formula (10e) using dithiothreitol, monopotassium phosphate, potassium carbonate in a solvent such as methanol in the presence of acetic acid at a range of temperatures preferably between room temperature and the boiling point of the solvent.

Compounds of formula (10e) can be prepared from compounds of formula (10d) using 2-nitrobenzenesulfenyl chloride in acetic acid at a range of temperatures preferably between room temperature and 100° C.

Compounds of formula (10d) can be prepared from compounds of formula (100c) using phthalimide, triphenylphosphine, and diisopropyl azodicarboxylate in a solvent such as tetrahydrofuran at a range of temperature preferably between 0° C. and the boiling point of the solvent.

Compounds of formula (10c) can be prepared from compounds of formula (10b) using a reducing agent such as sodium borohydride in a solvent such as methanol at a range of temperatures preferably between 0° C. and the boiling point of the solvent.

Compounds of formula (10b) can be prepared from compounds of formula (10a) using tert-butanethiol in the presence of a base such as diisopropylethyl amine in a solvent such as tetrahydrofuran at a range of temperatures preferably between 0° C. and the boiling point of the solvent.

Compounds of formula (10a) are known in the literature and can be prepared by those skilled in the art using literature methods (e.g. 3-bromo-indan-1-one, see WO 2010/108058, which is incorporated herein by reference in its entirety)

Alternatively, compounds of general formula (1bb), i.e. compounds of formula (1b) wherein Y=CH$_2$ and W=NH may be prepared according to the route illustrated in scheme 11:

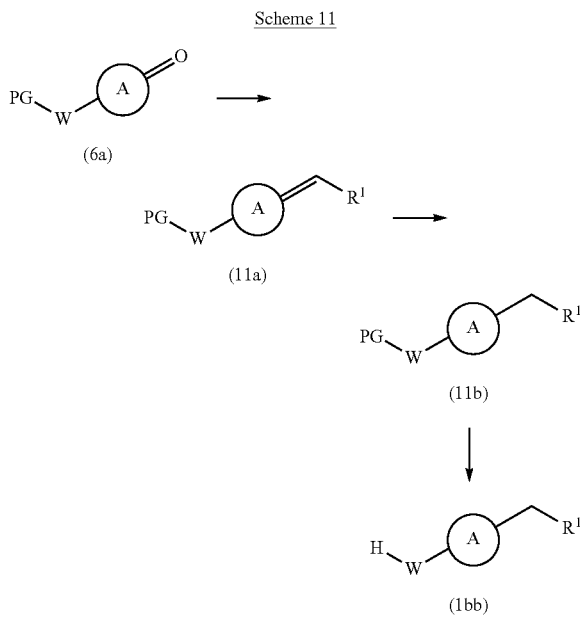

Compounds of general formula (1bb) may be prepared from compounds of general formula (11b) by removal of the protecting group PG using methods known in the art such as aqueous sodium hydroxide in a solvent such as methanol at a range of temperatures preferably between room temperature and 100° C.

Compounds of formula (11b) may be prepared from compounds of general formula (11a) by reaction with a suitable reduction agent for example hydrogen gas in the presence of a suitable catalyst such as palladium on activated charcoal in a suitable solvent such as ethanol at a range of temperatures between room temperature and 70° C. and pressures between atmospheric and 4 Barr.

Compounds of formula (11a) may be prepared from compounds of general formula (6a) by means of a reaction such as a Wittig (or one of the closely related variants such as the Horner-Wadsworth-Emmons) with a suitable substrate such as R$^1$—CH$_2$—P(O)(OMe)$_2$ in the presence of a suitable base such as sodium hydride in a suitable solvent such as tetrahydrofuran at a range of temperatures preferably between −10° C. and 100° C.

Compounds such as R$^1$—CH$_2$—P(O)(OMe)$_2$ may be synthesised from compounds of the general formula R$^1$—CH$_2$-Hal wherein Hal represents a halogen such as —Br or —Cl by reaction with a compound such as trimethylphosphite at a range of temperatures preferably between 0° C. and 100° C.

Compounds such as R$^1$—CH$_2$-Hal may be synthesised from compounds of formula R$^1$—CH$_3$ by means of a reaction such as a radical halogenation using a reagent such as N-bromosuccinimide in the presence of a catalyst such as AIBN in a suitable solvent such as carbon tetrachloride at a range of temperatures preferably between 0° C. and 80° C. Compounds such as R$^1$—CH$_2$-Hal may also be synthesised from compounds formula R$^1$—CH$_2$—OH by means of using halogenating conditions such as carbon tetrabromide and triphenylphosphine in dichloromethane or activation conditions such as methane sulfonyl chloride in dichloromethane in the presence of base such as diisopropylamine.

Compounds such as R$^1$—CH$_3$ and R$^1$—CH$_2$—OH may be prepared by methods outlined above for compounds (2b), (2c) and (2d).

Other features of the invention will become apparent in the course of the following descriptions of exemplary embodiments which are given for illustration of the invention and are not intended to be limiting thereof.

EXAMPLES

General Experimental Details

Abbreviations used in the experimental section:
AcOH=acetic acid;
aq.=aqueous;
DCM=dichloromethane;
DIAD=Diisopropyl azodicarboxylate;
DIPEA=diisopropylethylamine;
DMAP=N,N-dimethylaminopyridine;
DMF=N,N-dimethylformamide;
DMSO=dimethyl sulfoxide;
EDC=1-ethyl-3-(3'-dimethylaminopropyl)carbodiimide Hydrochloride;
EtOAc=ethyl acetate;
EtOH=ethanol;
Et$_2$O=diethyl ether;
Et$_3$N=triethylamine;
EtNiPr$_2$=diisopropylethylamine;
FCC=flash column chromatography;
h=hour;
HATU=2-(7-aza-1H-benzotriazole-1-yl)-1,1,3,3-tetramethyluronium hexafluorophosphate;
HOBt=1-hydroxy-benzotriazole; HPLC=high performance liquid chromatography;
IMS=Industrial Methylated Spirits;
LCMS=liquid chromatography mass spectrometry;
NaOH=sodium hydroxide;
MeCN=acetonitrile;
MeOH=MeOH;
min=minutes;
NH$_3$=ammonia;
NMR=nuclear magnetic resonance;
RT=room temperature;
Rt=retention time;
sat.=saturated;
SCX-2=strong cation exchange chromatography;
TFA=trifluoroacetic acid;
THF=Tetrahydrofuran;
H$_2$O=water;
IMS=industrial methylated spirit;
Xantphos=4,5-Bis(diphenylphosphino)-9,9-dimethylxanthene;
X-Select=Waters X-select HPLC column;
IPA=propan-2-ol;
LDA=lithium diisopropylamide;
MDAP=mass-directed auto-purification;
MeOH=methanol;
Ph$_3$P=triphenylphosphine;
TBAF=tetrabutylammonium fluoride.

In the procedures that follow, after each starting material, reference to a Intermediate/Example number is usually provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on comparisons with data reported in WO 2008/043019, which is incorporated herein by reference in its entirety, for key intermediates. All reactions were carried out under anhydrous conditions and an atmosphere of nitrogen or argon unless specified otherwise. Unless otherwise stated all transformations were carried at ambient temperature (room temperature).

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

Where products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d Genesis column with 7 µm particle size), or a Phenyl-Hexyl column (250×21.2 mm i.d. Gemini column with 5 µm particle size), UV detection between 220-254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid), or a C18-reverse-phase column (19×250 mm, XBridge OBD, with 5 µm particle size), eluting with gradients from 100-0 to 0-100% water/acetonitrile (containing 0.1% NH$_4$OH); or a ChiralPak IC column (10×250 mm i.d., with 5 µm particle size), unless otherwise indicated. Fractions containing the required product (identified by LCMS analysis) were pooled, the organic solvent removed by evaporation, and the remaining aqueous residue lyophilised, to give the final product. Products purified by preparative HPLC were isolated as free base, formate or TFA salts, unless otherwise stated.

The Liquid Chromatography Mass Spectroscopy (LCMS) and HPLC systems used are:
Method 1.
Waters Platform LC Quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line HP1100 DAD detector). MS ionization method—Electrospray (positive and negative ion).
Method 2.
Waters ZMD quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line Waters 996 DAD detector). MS ionization method—Electrospray (positive and negative ion).
Method 3.
Waters ZMD quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line HP1100 DAD detector). MS ionization method—Electrospray (positive and negative ion).
Method 4.
VG Platform II quadrupole spectrometer with a C18-reverse-phase column (30×4.6 mm Phenomenex Luna 3 µm particle size, elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 µl/min split to the ESI source with inline HP1050 DAD detector). MS ionization method—Electrospray (positive and negative ion).
Method 5.
Waters micromass ZQ2000 quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+ 0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 6.

Phenomenex Gemini C18-reverse-phase column (250×21.20 mm 5 μm particle size), elution with A: water+ 0.1% formic acid; B: CH$_3$CN+0.1% formic acid. Gradient— 90% A/10% B to 2% A/98% B over 20 min–flow rate 18 mL/min. Detection—In-line UV detector set at 254 nM wavelength.

Method 7.

Agilent 1260 inifinity purification system. Column: XSE-LECT CSH Prep C18 OBD, partical size 5 μm, 30×150 mm, RT. Elution with A: water+0.1% formic acid; B: CH$_3$CN+ 0.1% formic acid. Gradient—90% A/10% B to 2% A/95% B over 22 min–flow rate 60 mL/min. Detection—In-line Agilent 6100 series single Quadrupole LC/MS.

It is to be understood by the skilled person that, where the expression "partial formate salt" is used, it is to be intended as identifying derivatives where only part of the basic compound has been converted into formate salt and thus containing less than one equivalent of formate counterion. Exact salt/free base ratio is provided by associated NMS analysis.

Example 1

1-(5-tert-Butyl-2-(4-methoxy-phenyl)-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea

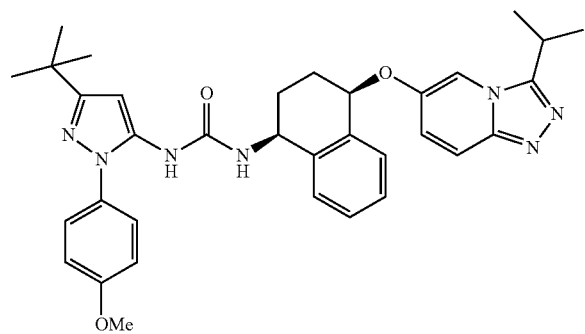 [SMILES: COc1ccc(-n2nc(C(C)(C)C)cc2NC(=O)N[C@H]2CC[C@@H](Oc3ccc4nnc(C(C)C)n4c3)c3ccccc32)cc1]

a. 2,2,2-Trifluoro-N—(S)-1,2,3,4-tetrahydro-naphthalen-1-yl-acetamide (Intermediate 1a)

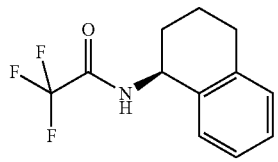 [SMILES: O=C(N[C@H]1CCCc2ccccc21)C(F)(F)F]

Ethyl trifluoroacetate (24.2 mL, 204 mmol) was added dropwise to a solution of (S)-(1,2,3,4-tetrahydro-naphthalen-1-yl)amine (Alfa Aesar; 25.0 g, 170 mmol) and triethylamine (35.5 mL, 255 mmol) in MeOH (250 mL) at RT and stirred for 18 h. The mixture was concentrated to approximately ⅓ of its volume and then partitioned between DCM (200 mL) and water (200 mL). The aqueous layer was extracted into DCM (3×) and the combined organic layers were washed with brine, dried (MgSO$_4$) and concentrated in vacuo to yield the title compound (41.1 g, 169 mmol, 99%). $^1$H NMR (400 MHz, CDCl$_3$): 1.80-1.95 (3H, m), 2.05-2.15 (1H, m), 2.75-2.90 (2H, m), 5.18-5.25 (1H, q, J=5.0 Hz), 6.38-6.48 (1H, br s), 7.12-7.16 (1H, m), 7.20-7.26 (3H, m).

b. 2,2,2-Trifluoro-N—((S)-4-oxo-1,2,3,4-tetrahydro-naphthalen-1-yl)-acetamide (Intermediate 1b)

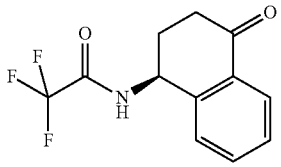 [SMILES: O=C1CC[C@H](NC(=O)C(F)(F)F)c2ccccc21]

Magnesium sulfate monohydrate (46.6 g, 338 mmol) in water (500 mL) was added to an ice cold solution of Intermediate 1a (41.1 g, 169 mmol) in acetone (1.0 L). Potassium permanganate (80.1 g, 507 mmol) was added portionwise (10.0 g portions) over a period of 45 min. The mixture was then stirred for 18 h. Sodium thiosulfate pentahydrate (126 g, 510 mmol) in water (400 mL) was added, and the reaction stirred for min. The mixture was concentrated to ~300 mL, then water (1.0 L), Celite (60g) and EtOAc (1.0 L) were sequentially added. The mixture was thoroughly stirred, and then filtered through a pad of Celite. The aqueous layer was extracted into EtOAc (3×) and the combined organic layers washed with brine, dried (MgSO$_4$) and concentrated in vacuo to yield the title compound (36.6 g, 142 mmol, 84%). $^1$H NMR (400 MHz, CDCl$_3$): 2.20-2.30 (1H, dddd, J 13.3, 10.0, 8.8, 4.5 Hz), 2.43-2.52 (1H, dddd, J 13.3, 7.2, 4.6, 4.6 Hz), 2.67-2.77 (1H, ddd, J 17.4, 10.1, 4.6 Hz), 2.78-2.88 (1H, ddd, J 17.4, 7.1, 4.6 Hz), 5.39-5.47 (1H, td, 8.5, 4.5 Hz), 7.32-7.37

(1H, d, J=7.7 Hz), 7.44-7.49 (1H, t, J=7.6 Hz), 7.59-7.64 (1H, td, J 7.6, 1.4 Hz), 8.03-8.07 (1H, dd, J 7.7, 1.4 Hz).

c. 2,2,2-Trifluoro-N-((1S,4R)-4-hydroxy-1,2,3,4-tetrahydro-naphthalen-1-yl)-acetamide (Intermediate 1c)

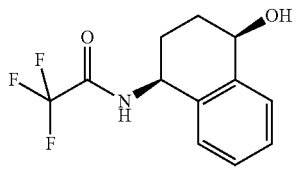 [SMILES: O=C(N[C@H]1CC[C@@H](O)c2ccccc21)C(F)(F)F]

Degassed DMF (argon sparged, 100 mL) was added to Intermediate 1b (8.00 g, 31.3 mmol) and [N-[(1R,2R)-2-(amino-κN)-1,2-diphenylethyl]-4-methylbenzenesulfonamidato-κN]chloro[(1,2,3,4,5,6-η)-1-methyl-4-(1-methylethyl)benzene]-ruthenium (Strem Chemicals Inc.; 594 mg, 0.93 mmol). Triethylamine (8.66 mL, 62.6 mmol) was added slowly to ice cold formic acid (2.34 mL, 62.6 mmol) and stirred for 20 min; this was then added to the DMF solution. The reaction was heated to 60° C. for 18 h. After cooling, the mixture was partitioned between DCM (200 mL) and water (600 mL). The aqueous layer was extracted DCM (3×) and the combined organic layers washed with brine, dried (MgSO$_4$) and concentrated in vacuo. Purification by FCC, using 0-100% EtOAc in cyclohexane, afforded the title compound (7.10 g, 27.4 mmol, 88%). $^1$H NMR (400 MHz, CDCl$_3$): 1.88-1.92 (1H, d, J=4.8 Hz), 1.98-2.18 (4H, m), 4.80-4.88 (1H, m), 5.165-5.24 (1H, m), 6.70-6.80 (1H, br s), 7.25-7.30 (1H, m), 7.30-7.40 (2H, m), 7.45-7.50 (1H, m).

d. (1R,4S)-4-Amino-1,2,3,4-tetrahydro-naphthalen-1-ol (Intermediate 1d)

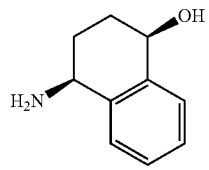 [SMILES: N[C@H]1CC[C@@H](O)c2ccccc21]

Sodium hydroxide (2.10 g, 53.0 mmol) was added to an ice cold solution of Intermediate 1c (3.43 g, 13.2 mmol) in MeOH/water (2:1, 50 mL) and stirred for 3.5 h. The mixture was loaded on to a SCX-2 cartridge, eluting with MeOH then 2M NH$_3$ in MeOH, to yield the title compound (2.30 g, 13.2 mmol, 99%). $^1$H NMR (400 MHz, d$_6$-DMSO): 1.66-1.90 (4H, m), 3.71-3.77 (1H, t, J=5.4 Hz), 4.46-4.54 (1H, t, J=5.4 Hz), 7.14-7.22 (2H, m), 7.32-7.38 (1H, m), 7.40-7.46 (1H, m).

e. Isobutyric acid N'-(5-fluoro-pyridin-2-yl)-hydrazide (Intermediate 1e)

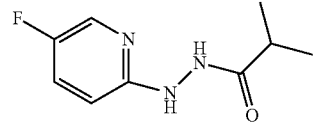

To a solution of 5-fluoro-2-hydrazinyl-pyridine (for reference procedure see WO 2010/022076, which is incorporated herein by reference in its entirety; 2.08 g, 16.4 mmol), isobutyric acid (1.82 mL, 19.6 mmol), and HOBt hydrate (251 mg, 1.64 mmol) in DCM (50 mL), EDC (3.76 g, 19.6 mmol) was added, and the resulting orange solution was stirred at room temperature for 18 h. Sat. aq. NaHCO$_3$ (50 mL) was added, and the mixture was stirred vigorously for 15 min. The organics were washed with sat. aq. NaHCO$_3$ (50 mL), passed through a hydrophobic frit, and concentrated under vacuum to leave a pale brown solid. The solid was suspended in Et$_2$O (50 mL) and filtered, washing with Et$_2$O (25 mL), to leave a white solid (1.48 g, 46%). The ethereal washings were concentrated under vacuum and the residue suspended in Et$_2$O (10 mL), filtered, washed with Et$_2$O (2×2 mL), to leave a white solid (330 mg, 10%). The solids were combined (1.81 g, 56%). $^1$H NMR (400 MHz, CDCl$_3$): 1.23 (6H, d), 2.50 (1H, sept), 6.65 (1H, dd), 6.80 (1H, d), 7.29 (1H, ddd), 7.77 (1H, br s), 8.01 (1H, d).

f. 6-Fluoro-3-isopropyl-[1,2,4]triazolo[4,3-a]pyridine (Intermediate 1f)

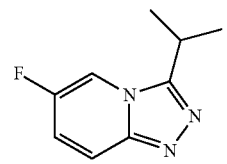

To a solution of Intermediate 1e (1.81 g, 9.18 mmol), triphenylphosphine (4.83 g, 18.4 mmol), and triethylamine (5.12 mL, 36.7 mmol) in THF (25 mL) at 0° C., hexachloroethane (4.36 g, 18.4 mmol) was added in 2 portions at a 1 min intervals. The resulting pale brown solution was allowed to warm to RT then stirred for 2 h. The resulting yellow suspension was filtered, washing with THF (2×25 mL). The combined organics were purified using SCX-2 cartridge (washed with DCM-MeOH (1:1, 100 mL) and MeOH (50 mL), and then the product was eluted with 2M NH$_3$ in MeOH) to give a pale yellow solid (1.60 g, 97%, contaminated with ~2.5%

Ph$_3$P=O). $^1$H NMR (400 MHz, CDCl$_3$): 1.53 (6H, d), 3.32 (1H, sept), 7.15 (1H, ddd), 7.75 (1H, ddd), 7.84 (1H, m).

g. (1S,4R)-4-(3-Isopropyl-[1,2,4]triazolo[4,3-a]pyridin-6-yloxy)-cis-1,2,3,4-tetrahydro-naphthalen-1-ylamine (Intermediate 1g)

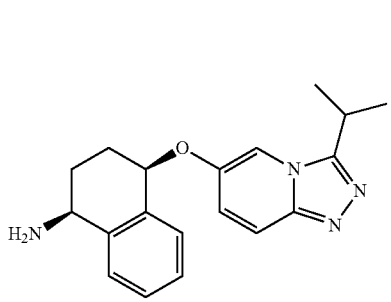 [SMILES: CC(C)c1nnc2ccc(O[C@@H]3CC[C@H](N)c4ccccc43)cn12]

Intermediate 1d (634 mg, 3.88 mmol) was added portionwise to a suspension of sodium hydride (60% in mineral oil, 466 mg, 11.65 mmol) in dry DMF (5 mL), and the mixture stirred at RT for 20 min. Intermediate if (535 mg, 2.99 mmol) was then added portionwise, and the mixture heated at 60° C. for 4 h. The reaction was cooled, quenched with water, and extracted with EtOAc (3×). The combined organic extracts were washed with brine and dried (Na$_2$SO$_4$), evaporated and purified by SCX-2 eluting with MeOH then 2M NH$_3$ in MeOH, to afford the title compound (274 mg, 79%). LCMS (Method 1): Rt 1.76 min, m/z 180 [MH$^+$].

h. 1-(5-tert-Butyl-2-(4-methoxy-phenyl)-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea (Example 1)

A solution of Intermediate 1g (87 mg, 0.27 mmol), DIPEA (318 µL, 1.86 mmol) and [5-tert-butyl-2-(4-methoxy-phenyl)-2H-pyrazol-3-yl]-carbamic acid 2,2,2-trichloroethyl ester (for reference procedure see WO 2001/004115, which is incorporated herein by reference in its entirety; 260 mg, 0.62 mmol) in DMF (5 mL) was heated at 60° C. for 2 h. After cooling, the solution was passed through a SCX-2 cartridge, eluting with MeOH then 2M NH$_3$ in MeOH, to afford the crude title compound. Further purification by HPLC (55-98% H$_2$O in MeCN (0.1% NH$_3$)) gave the title compound as a colourless powder (35 mg, 9.5%). LCMS (Method 5): Rt 4.46 min, m/z 594 [MH$^+$]. $^1$H NMR (400 MHz, d$_6$-DMSO): 1.21 (9H, s), 1.31-1.35 (6H, dd, J 5.8), 1.76-1.93 (3H, m), 2.01-2.08 (2H, m), 3.47-3.57 (1H, m), 3.75 (3H, s), 4.75-4.81 (1H, m), 5.48 (1H, t, J 3.9), 6.26 (1H, s), 6.98-7.05 (3H, m), 7.09-7.13 (1H, m), 7.09-7.13 (6H, m), 7.62-7.65 (1H, d, J 9.98).

Example 2

1-(5-tert-Butyl-2-methyl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea

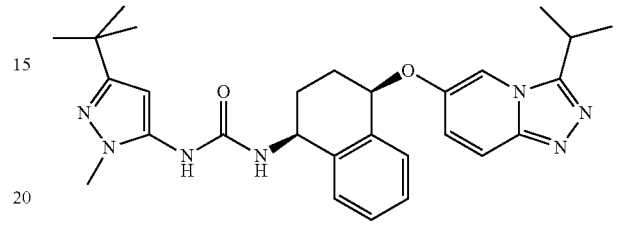

Diisopropylethylamine (54 µL, 0.31 mmol) was added to a solution of Intermediate 1g (100 mg, 0.31 mmol) and (5-tert-butyl-2-methyl-2H-pyrazol-3-yl)-carbamic acid 2,2,2-trichloro-ethyl ester (for reference procedure see US2004/192653, which is incorporated herein by reference in its entirety; 102 mg, 0.31 mmol) in 1,4-dioxane (3.0 mL). The reaction was heated to 100° C. for 18 h. After cooling, the mixture was partitioned between EtOAc (50 mL) and water (50 mL). The aqueous layer was extracted into EtOAc (3×) and the combined organic layers were washed with brine, dried (MgSO$_4$) and concentrated in vacuo. Purification by FCC, using 0-10% [2M NH$_3$ in MeOH] in DCM, followed by HPLC (10-98% MeCN in H$_2$0, 0.1% formic acid) afforded the title compound (63 mg, 0.13 mmol, 41%). LCMS (Method 5: Rt 3.71 mins, m/z 502 [MH$^+$]. $^1$H NMR (400 MHz, CDCl$_3$): 1.24 (9H, s), 1.41-1.44 (3H, d, J 6.9), 1.45-1.48 (3H, d, J 6.9), 1.90-2.00 (1H, m), 2.04-2.17 (2H, m), 2.22-2.30 (1H, m), 3.18-3.29 (1H, sp, J 6.9), 3.72 (3H, s), 5.08-5.15 (1H, td, J 8.8, 5.2), 5.16-5.21 (1H, t, J 3.8), 5.45-5.55 (1H, br d, J 7.4), 6.02 (1H, s), 6.60-6.68 (1H, br s), 6.99-7.04 (1H, dd, J 9.9, 2.1), 7.24-7.28 (2H, m), 7.30-7.36 (1H, m), 7.36-7.44 (2H, m), 7.56-7.60 (1H, d, J 9.9).

Example 3

1-{5-tert-Butyl-2-[3-(2-hydroxyethylsulfanyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea

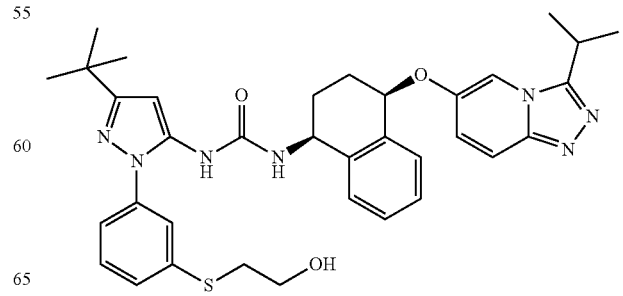

a. Di-tert-butyl 1-{3-[(2-{[tert-butyl(dimethyl)silyl]oxy}ethyl)sulfanyl]phenyl}hydrazine-1,2-dicarboxylate (Intermediate 3a)

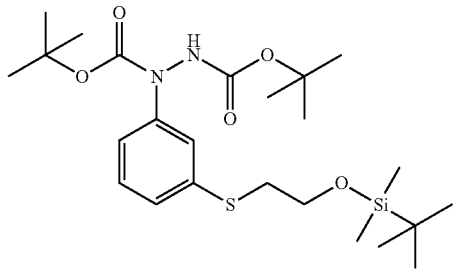 [SMILES: CC(C)(C)OC(=O)NN(C(=O)OC(C)(C)C)c1cccc(SCCO[Si](C)(C)C(C)(C)C)c1]

A mixture of 3-bromothiophenol (1.00 g, 5.29 mmol), bromoethoxydimethylsilyl ether (1.36 mL, 6.35 mmol) and potassium carbonate (1.46 g, 10.58 mmol) in acetone (15 mL) was stirred at RT overnight. The mixture was filtered, evaporated, the residue dried under vacuum, and then dissolved in dry THF (15 mL). nBuLi (1.6M in hexanes, 4.5 mL, 7.28 mmol) was added dropwise at −78° C. and stirred for 10 min. Di-tert-butyl azodicarboxylate (1.54 g, 6.68 mmol) was added in one portion at −78° C. and stirred for min. The mixture was then allowed to warm to RT over 2 h. The mixture was partitioned between saturated ammonium chloride (15 mL) solution and ethyl acetate (3×15 mL). The combined organic extracts were washed with brine (20 mL), dried (Na$_2$SO$_4$) and concentrated in vacuo. The residue was purified by FCC, using 0-20% ethyl acetate in pentane, affording the title compound as a pale yellow oil (1.68 g, 64%). $^1$H NMR (400 MHz, CDCl$_3$): 0.04 (6H, s), 0.84 (9H, s), 1.48 (18H, m), 3.04 (2H, t), 3.79 (2H, t), 7.14-7.24 (2H, m), 7.42 (1H, s).

b. 2-[3-(5-Amino-3-tert-butyl-pyrazol-1-yl)phenylsulfanyl]-ethanol. (Intermediate 3b)

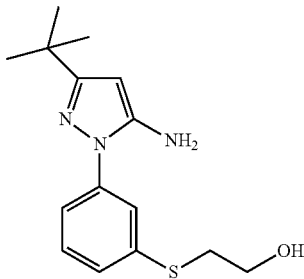 [SMILES: CC(C)(C)c1cc(N)n(-c2cccc(SCCO)c2)n1]

A mixture of Intermediate 3a (1.68 g, 3.37 mmol), pivaloyl acetonitrile (0.42 g, 3.37 mmol), and concentrated HCl solution (1.7 mL) in ethanol (10 mL) was heated under reflux for 3 h. After cooling, the pH was adjusted to ca. 7 (using aqueous saturated NaHCO$_3$), and the mixture partitioned between water (20 mL) and EtOAc (3×20 mL). The combined organic extracts were washed with brine (20 mL), dried (Na$_2$SO$_4$) and concentrated in vacuo. The residue was purified by FCC, eluting with 20-80% EtOAc in pentane, affording the title compound as a pale yellow oil (458 mg, 47%). LCMS (Method 1): Rt 2.35 min, m/z 292 [MH$^+$].

c. {5-tert-Butyl-2-[3-(2-hydroxy-ethylsulfanyl)-phenyl]-2H-pyrazol-3-yl}-carbamic acid 2,2,2-trichloroethyl ester. (Intermediate 3c)

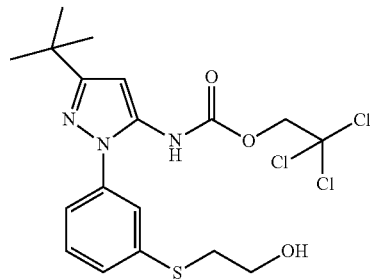 [SMILES: CC(C)(C)c1cc(NC(=O)OCC(Cl)(Cl)Cl)n(-c2cccc(SCCO)c2)n1]

Trichloroethyl chloroformate (0.1 mL, 0.78 mmol) was added to a solution of Intermediate 3b (176 mg, 0.60 mmol) and DIPEA (0.31 mL, 1.81 mmol) in THF (10 mL), and the mixture stirred for 3 h. The mixture was then partitioned between water (15 mL) and EtOAc (3×20 mL), and the combined organic extracts dried (Na$_2$SO$_4$) and concentrated in vacuo. The residue was triturated (cyclohexane) and filtered to give the title compound as a yellow solid (280 mg, 100%). LCMS (Method 1): Rt 3.93 min, m/z 466/468 [MH$^+$]

d. 1-{5-tert-Butyl-2-[3-(2-hydroxy-ethylsulfanyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea. (Example 3)

A solution of Intermediate 1g (100 mg, 0.31 mmol) in DMF (2 mL) with DIPEA (165 µL, 0.97 mmol) and Intermediate 3c (145 mg, 0.31 mmol) was heated at 60° C. for 2 h. After cooling, the mixture was loaded on to a SCX-2 cartridge, eluting with MeOH then 2M NH$_3$ in MeOH, to afford the crude product. Further purification by FCC, eluting with 0-10% [2M NH$_3$ in MeOH] in DCM, followed by HPLC (elution with 30-95% MeCN in H$_2$O (0.1% HCO$_2$H)) gave the title compound as a colourless powder (45 mg). LCMS (Method 5): Rt 4.22 min, m/z 640 [MH$^+$]. $^1$H NMR (400 MHz, CDCl$_3$): 1.33 (9H, s), 1.42-1.47 (6H, m), 1.89-1.97 (1H, m), 2.04-2.13 (2H, m), 2.21-2.28 (1H, m), 3.09 (2H, m), 3.24 (1H, m), 3.73 (2H, m), 5.08 (1H, m), 5.19 (1H, m,), 5.78

(1H, m), 6.38 (1H, s), 6.92 (1H, br s), 7.01 (1H, dd, J 1.92, 9.77), 7.24-7.34 (6H, m), 7.40-7.43 (2H, m), 7.54-7.75 (2H, m).

gave semi-pure title compound (1.26 g). This was used in the next reaction without further purification. LCMS (Method 4): Rt 2.77, m/z 360 [MH⁺].

Example 4

1-{5-tert-Butyl-2-[3-(2-hydroxy-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea b. (5-tert-Butyl-2-{3-[2-(tetrahydro-pyran-2-yloxy)-ethoxy]-phenyl}-2H-pyrazol-3-yl)-carbamic acid 2,2,2-trichloro-ethyl ester (Intermediate 4b)

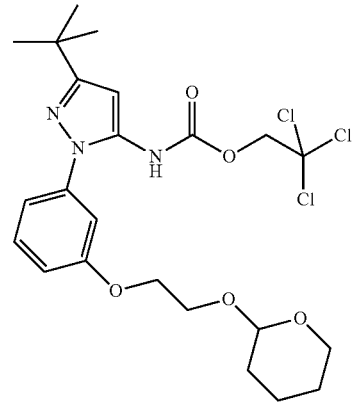

The title compound was prepared starting from 2,2,2-trichloroethylchloroformate and Intermediate 4a by using an analogous procedure to that described for Example 3 step c. LCMS (Method 4): Rt 3.85, m/z 536 [MH⁺].

c. 1-(5-tert-Butyl-2-{3-[2-(tetrahydro-pyran-2-yloxy)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea (Intermediate 4c)

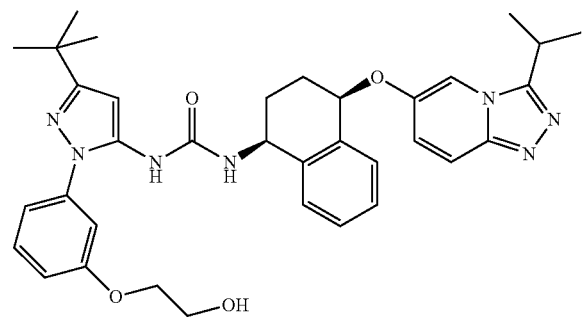 [SMILES: CC(C)c1nnc2ccc(O[C@@H]3CC[C@H](NC(=O)Nc4cc(C(C)(C)C)nn4-c4cccc(OCCO)c4)c4ccccc43)cn12]

a. 5-tert-Butyl-2-{3-[2-(tetrahydro-pyran-2-yloxy)-ethoxy]-phenyl}-2H-pyrazol-3-ylamine (Intermediate 4a)

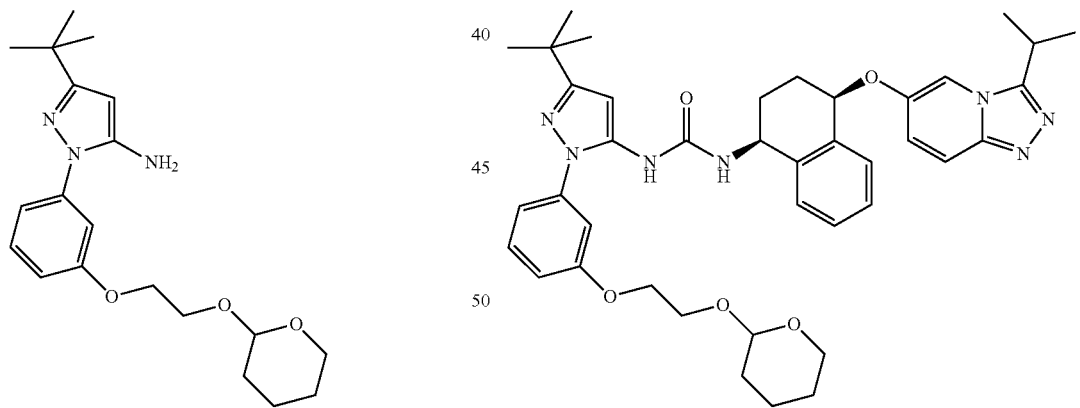

DIAD (847 µL, 4.32 mmol) was added slowly to a solution of 3-(5-amino-3-tert-butyl-1H-pyrazol-1-yl)phenol (for reference procedure see US 2006/35922, which is incorporated herein by reference in its entirety; 500 mg, 2.16 mmol), 2-(tetrahydro-pyran-2-yloxy)-ethanol (439 µL, 3.25 mmol), and triphenylphosphine (1.13 g, 4.32 mmol) in THF (10.0 mL) and stirred for 72 h. The reaction mixture was partitioned between EtOAc (75 mL) and H₂O (75 mL), and the aqueous layer extracted with EtOAc (3×). The combined organic layers were dried (MgSO₄), filtered and evaporated in vacuo. Purification by FCC, using 5-60% EtOAc in cyclohexane, The title compound was prepared starting from Intermediate 4b and Intermediate 1g by using an analogous procedure to that described for Example 1 step h. LCMS (Method 1): Rt 3.63 mins, m/z=708 [MH⁺].

d. 1-{5-tert-Butyl-2-[3-(2-hydroxy-ethoxy)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea (Example 4)

Pyridinium para-toluene sulfonate (44.0 mg, 0.17 mmol) was added to Intermediate 4c (124 mg, 0.17 mmol) in MeOH (3.0 mL). After 2 h, further pyridinium para-toluene sulfonate (100 mg, 0.39 mmol) was added, and the reaction stirred for 12 h. The reaction was then heated to 55° C. for 2 h, then cooled, and the solvent volume reduced to approximately ⅓ of its volume in vacuo. The residue was partitioned between EtOAc (50 mL) and saturated NaHCO$_3$ (50 mL). The aqueous layer was extracted into EtOAc (3×), then the combined organic layers washed with brine, dried (MgSO$_4$) and evaporated in vacuo. The product was purified by FCC, using 0-10% MeOH in DCM, then further purified by HPLC (C18 X-select column, 10-98% MeCN in H$_2$O, 0.1% formic acid) to give the title compound (50.0 mg, 0.08 mmol, 47%). LCMS (Method 5): Rt 4.04 mins, m/z 624 [MH$^+$]. $^1$H NMR (400 MHz, CDCl$_3$): 1.30 (9H, s), 1.40-1.44 (3H, d, J=6.9 Hz), 1.44-1.47 (3H, d, J=6.9 Hz), 1.84-1.98 (1H, m), 2.00-2.10 (2H, m), 2.18-2.26 (1H, m), 3.16-3.26 (1H, sp, J=6.9 Hz), 3.87-3.92 (2H, m), 4.03-4.07 (2H, m), 5.01-5.09 (1H, td, J 8.9, 5.3 Hz), 5.14-5.17 (1H, t, J=4.0 Hz), 5.47-5.52 (1H, br d, J=8.7 Hz), 6.29 (1H, s) 6.60 (1H, br s), 6.80-6.84 (1H, m), 6.96-7.00 (1H, dd, J 9.9, 2.1 Hz), 7.07-7.11 (2H, m), 7.23-7.30 (5H, m), 7.38-7.40 (1H, d, J=1.6 Hz), 7.53-7.57 (1H, d, J=9.9 Hz).

Example 5

1-(5-tert-Butyl-[1,3,4]oxadiazol-2-yl)-3-[(1S,4S)-4-(3-isopropyl-[1,2,4]triazolo[4,3-a]pyridin-6-yloxy)-1,2,3,4-tetrahydro-naphthalen-1-yl]-urea

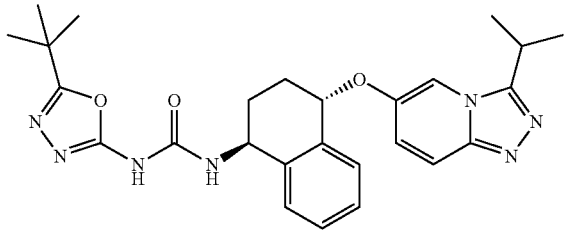 [SMILES: CC(C)c1nnc2ccc(O[C@H]3CC[C@H](NC(=O)Nc4nnc(C(C)(C)C)o4)c4ccccc43)cn12]

a. 2,2,2-Trifluoro-N-((1S,4S)-4-hydroxy-1,2,3,4-tetrahydro-naphthalen-1-yl)-acetamide (Intermediate 5a)

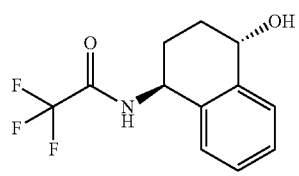 [SMILES: O=C(N[C@H]1CC[C@H](O)c2ccccc21)C(F)(F)F]

Argon was bubbled through a solution of Intermediate 1b (8.00 g, 31.1 mmol) and [N-[(1S,2S)-2-(amino-κN)-1,2-diphenylethyl]-4-methylbenzenesulfonamidato-κN]chloro[(1,2,3,4,5,6-η)-1-methyl-4-(1-methylethyl)benzene]-ruthenium (Strem Chemicals Inc.; 0.06 g, 0.93 mmol) in dry DMF (100 mL) for 10 min. A premixed combination of formic acid (2.4 mL, 62.2 mmol) and Et$_3$N (8.60 mL, 62.2 mmol) was added, and the mixture stirred at 50° C. for 24 h. The mixture was cooled to room temperature and concentrated to ~25 mL. Water (70 mL) was added and the resulting precipitate filtered, and washed with DCM (3×30 mL) and diethyl ether (30 mL) to leave a solid (4.75 g). The filtrate was decanted to leave a dark solid. Subsequent purification by FCC using 0-30% EtOAc in cyclohexane gave a solid. This was combined with the first obtained solid to give a beige solid (5.93 g, 74%). $^1$H NMR (400 MHz, d$_6$-DMSO): 1.60-1.83 (2H, m), 2.06-2.17 (2H, m), 4.60 (1H, m), 5.08 (1H, m), 5.28 (1H, d), 7.07 (1H, m), 7.25 (1H, ddd), 7.28 (1H, ddd), 7.50 (1H, dd), 9.78 (1H, d).

b. (1S,4S)-4-Amino-1,2,3,4-tetrahydro-naphthalen-1-ol (Intermediate 5b)

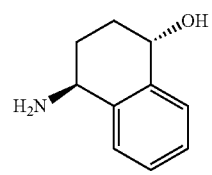 [SMILES: N[C@H]1CC[C@H](O)c2ccccc21]

To a grey solution of Intermediate 5a (5.55 g, 21.4 mmol) in MeOH (50 mL), NaOH (1.28 g, 32.1 mmol) in water (15 mL) was added, and the mixture stirred at room temperature for 3 days. NaOH (1.28 g, 32.1 mmol) was further added and the brown solution was stirred for 5 h. The solution was applied directly to an SCX-2 column, washing with MeOH and eluting with 2M NH$_3$ in MeOH, and concentrated under vacuum to leave a grey solid. The solid was suspended in DCM (50 mL) with sonication, then filtered and dried under vacuum to leave a pale grey solid (2.93 g, 84%). $^1$H NMR (400 MHz, d$_6$-DMSO): 1.41-1.64 (2H, m), 2.02-2.13 (2H, m), 3.82 (1H, dd), 4.55 (1H, dd), 5.08 (1H, br s), 7.13-7.22 (2H, m), 7.35-7.49 (2H, m).

c. (1S,4S)-4-(3-Isopropyl-[1,2,4]triazolo[4,3-a]pyridin-6-yloxy)-1,2,3,4-tetrahydro-naphthalen-1-ylamine (Intermediate 5c)

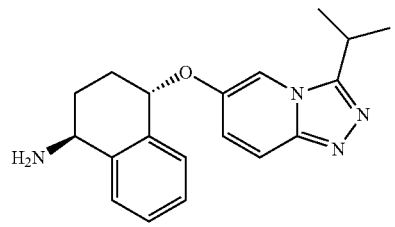 [SMILES: CC(C)c1nnc2ccc(O[C@H]3CC[C@H](N)c4ccccc43)cn12]

To a suspension of sodium hydride (60% in mineral oil, 1.07 g, 26.8 mmol) in dry DMF (20 mL) at room temperature under nitrogen, Intermediate 5b (1.89 g, 11.6 mmol) was added portionwise over 2 min, and the resulting brown solution was stirred for 20 min. Intermediate 1f (1.60 g, 8.93 mmol) was added, and the solution stirred at 60° C. for 2 h. The dark brown solution was cooled to room temperature and concentrated under vacuum. The residue was purified by SCX-2, washing with MeOH (200 mL) and eluting with 2M NH$_3$ in MeOH, to leave a dark brown foam (3.21 g). Further purification by FCC, using 2-10% [2M NH$_3$ in MeOH] in DCM, gave a brown foam (2.11 g, 76%). $^1$H NMR (400 MHz, d$_6$-DMSO): 1.37 (3H, d), 1.39 (3H, d), 1.59 (1H, m), 1.91

(1H, m), 2.11 (1H, m), 2.33 (1H, m), 3.58 (1H, sept), 3.96 (1H, dd), 5.55 (1H, dd), 7.18-7.37 (4H, m), 7.51 (1H, d), 7.68 (1H, d), 8.20 (1H, d).

d. (5-tert-Butyl-[1,3,4]oxadiazol-2-yl)-carbamic acid 2,2,2-trichloro-ethyl ester (Intermediate 5d)

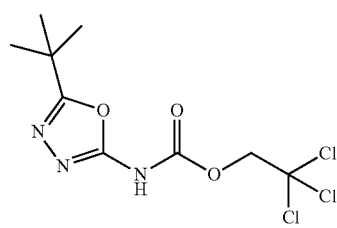 [SMILES: CC(C)(C)c1nnc(NC(=O)OCC(Cl)(Cl)Cl)o1]

To a suspension of 5-tert-butyl-[1,3,4]oxadiazol-2-ylamine (Atlantic, 141 mg, 1.00 mmol) and Et$_3$N (279 µL, 2.00 mmol) in MeCN (2 mL), 2,2,2-trichloroethyl chloroformate (207 µL, 1.50 mmol) was added in 4 portions over 1 min at RT (CARE: exotherm to ~40° C.). The resulting suspension was stirred for 1 h. The suspension was filtered, washing the solid with MeCN (3 mL), and concentrated to leave a yellow-brown paste. Purification by FCC, using 0-2.5% MeOH in DCM, gave a buff foam (232 mg, 73%). $^1$H NMR (400 MHz, CDCl$_3$): 1.42 (9H, s), 4.86 (2H, s).

e. 1-(5-tert-Butyl-[1,3,4]oxadiazol-2-yl)-3-[(1S,4S)-4-(3-isopropyl-[1,2,4]triazolo[4,3-a]pyridin-6-yloxy)-1,2,3,4-tetrahydro-naphthalen-1-yl]-urea (Example 5)

A solution of Intermediate 5d (83.1 mg, 0.263 mmol), Intermediate 5c (80.6 mg, 0.250 mmol), and DIPEA (54.4 µL, 0.313 mmol) in DMF (2 mL) was stirred at 125° C. for 45 min. After cooling, the mixture was concentrated in vacuo to give a brown oil. This was suspended in water (5 mL) and extracted with DCM (2×5 mL). The combined organics were passed through a hydrophobic frit and concentrated under vacuum to leave a brown oil. Purification by FCC, using 0-8% MeOH in EtOAc, followed by trituration (diethyl ether) afforded a buff solid (99.6 mg). Further purification by HPLC (10-98% MeCN in H$_2$O, 0.1% HCO$_2$H) gave the title compound as a flocculent white solid (25.9 mg, 21%). LCMS (Method 5): Rt 3.77 min, m/z 490 [MH$^+$]. $^1$H NMR (400 MHz, CDCl$_3$): 1.39 (9H, s), 1.52 (3H, d), 1.55 (3H, d), 2.00 (1H, m), 2.21-2.36 (2H, m), 2.43 (1H, m), 3.32 (1H, sept), 5.28-5.34 (2H, m), 7.12 (1H, dd), 7.30-7.38 (3H, m), 7.47-7.50 (2H, m), 7.73 (1H, d), 8.35 (1H, br s), 8.49 (1H, br d).

Example 6

1-[(1S,4S)-4-(3-Isopropyl-[1,2,4]triazolo[4,3-a]pyridin-6-yloxy)-1,2,3,4-tetrahydro-naphthalen-1-yl]-3-(1-p-tolyl-1H-pyrazol-4-yl)-urea

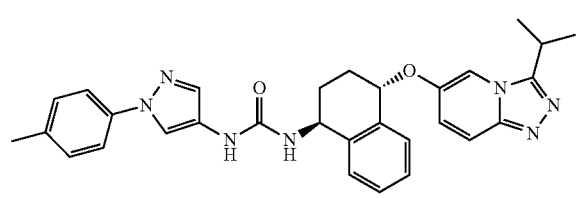 [SMILES: Cc1ccc(-n2cc(NC(=O)N[C@H]3CC[C@H](Oc4ccc5nnc(C(C)C)n5c4)c4ccccc43)cn2)cc1]

a. 4-Nitro-1-p-tolyl-1H-pyrazole (Intermediate 6a)

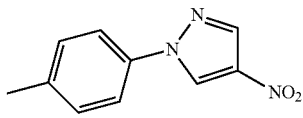

To 4-tolylboronic acid (544 mg, 4.00 mmol), 4-nitropyrazole (226 mg, 2.00 mmol), copper (II) acetate (545 mg, 3.00 mmol), and 4 Å sieves (1.5 g) in DCM (15 mL), was added pyridine (0.32 mL, 4 mmol) at RT, and stirred for 5 h. The mixture was filtered through Celite, washing with DCM, then evaporated to dryness. The residue was purified by FCC, eluting with 0-30% ethyl acetate in cyclohexane, to give the title compound as a white solid (126 mg, 31%). LCMS (Method 3): Rt 3.93 min, m/z 204.1 [MH$^-$].

b. 4-Amino-1-p-tolyl-1H-pyrazole (Intermediate 6b)

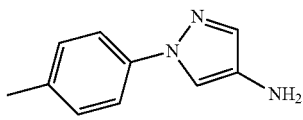

Intermediate 6a (212 mg, 1.04 mmol) was dissolved in ethanol (20 mL) then hydrogenated over 10% palladium on carbon for 4 h under hydrogen atmosphere. The mixture was then filtered through Celite, washing with ethanol, and evaporated to dryness. The residue was purified by FCC, eluting with 0-10% MeOH in DCM, to give the title compound as a pale brown solid (154 mg, 86%). LCMS (Method 3): Rt 1.92 min, m/z 174.1 [MH⁻].

c. (1-p-Tolyl-1H-pyrazol-4-yl)-carbamic acid 2,2,2-trichloro-ethyl ester (Intermediate 6c)

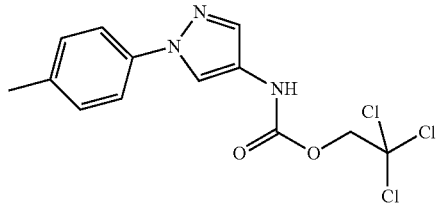 [SMILES: Cc1ccc(-n2cc(NC(=O)OCC(Cl)(Cl)Cl)cn2)cc1]

Intermediate 6b (150 mg, 0.87 mmol) dissolved in DCM (10 mL) was cooled using an ice bath, and then treated sequentially with triethylamine (0.18 mL, 1.30 mmol) and trichloroethyl chloroformate (0.15 mL, 1.08 mmol). The mixture was stirred with cooling for 45 min, then evaporated to dryness. Residue was purified by FCC, eluting with 0-30% ethyl acetate in cyclohexane, to give the title compound as a beige solid (286 mg, 95%). LCMS (Method 3): Rt 4.25 min, m/z 348/350/352 [MH⁺].

d. 1-[(1S,4S)-4-(3-Isopropyl-[1,2,4]triazolo[4,3-a]pyridin-6-yloxy)-1,2,3,4-tetrahydro-naphthalen-1-yl]-3-(1-p-tolyl-1H-pyrazol-4-yl)-urea (Example 6)

A solution of Intermediate 6c (65.0 mg, 0.19 mmol), Intermediate 5c (50.0 mg, 0.155 mmol), and DIPEA (0.127 mL, 0.8 mmol) in DMF (1 mL) was heated at 110° C. for 75 min and 50° C. for 64 h. After cooling, the mixture was concentrated to dryness and the residue purified by FCC, eluting with 0-10% MeOH in DCM, to give the impure product (63 mg). Further purification by HPLC (Method 6) gave the title compound as a white solid (45 mg, 56%). LCMS (Method 5): Rt 4.06 min, m/z 522.1 [MH⁺]. ¹H NMR (400 MHz, d₆-DMSO): 1.36-1.41 (6H, m), 1.76-1.85 (1H, m), 1.98-2.08 (1H, m), 2.13-2.28 (2H, m), 2.33 (3H, s), 3.59 (1H, quintet, J 6.8), 4.96-5.03 (1H, m), 5.62 (1H, t, J 4.6), 6.74 (1H, d, J 8.5), 7.24 (1H, dd, J 9.9, 2.1), 7.26-7.46 (6H, m), 7.62-7.66 (2H, m), 7.68 (1H, s), 7.70 (1H, dd, J 9.9, 0.8), 8.24 (1H, br d), 8.26 (1H, s), 8.31 (1H, s).

Example 7

1-(4-Chloro-3-trifluoromethyl-phenyl)-3-[(1S,4S)-4-(3-isopropyl-[1,2,4]triazolo[4,3-a]pyridin-6-yloxy)-1,2,3,4-tetrahydro-naphthalen-1-yl]-urea

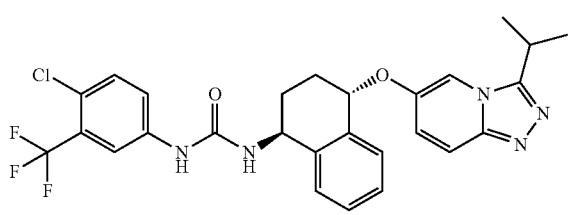 [SMILES: CC(C)c1nnc2ccc(O[C@H]3CC[C@H](NC(=O)Nc4ccc(Cl)c(C(F)(F)F)c4)c4ccccc43)cn12]

The title compound was prepared starting from 4-chloro-3-(trifluoromethyl)aniline (Aldrich) by using analogous procedures to those described for Example 5. LCMS (Method 5): Rt 4.72 min, m/z 544 [MH⁺]; ¹H NMR (400 MHz, d₆-DMSO): 1.38 (3H, d), 1.40 (3H, d), 1.83 (1H, m), 2.04 (1H, m), 2.21 (2H, m), 3.58 (1H, sept), 5.00 (1H, m), 5.62 (1H, m), 6.84 (1H, d), 7.24 (1H, dd), 7.30-7.41 (3H, m), 7.44 (1H, d), 7.56 (1H, d), 7.58 (1H, d), 7.70 (1H, d), 8.13 (1H, m), 8.24 (1H, d), 8.83 (1H, s).

Example 8

1-(3-tert-Butyl-[1,2,4]oxadiazol-5-yl)-3-[(1S,4S)-4-(3-isopropyl-[1,2,4]triazolo[4,3-a]pyridin-6-yloxy)-1,2,3,4-tetrahydro-naphthalen-1-yl]-urea

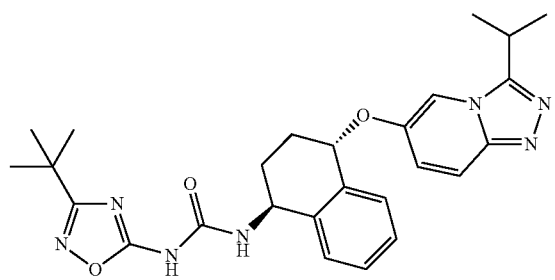 [SMILES: CC(C)c1nnc2ccc(O[C@H]3CC[C@H](NC(=O)Nc4nc(C(C)(C)C)no4)c4ccccc43)cn12]

The title compound was prepared starting from 3-tert-butyl-1,2,4-oxadiazol-5-amine (Enamine) using analogous procedures to those described for Example 5. LCMS (Method 5): Rt 4.12 min, m/z 490 [MH⁺]; ¹H NMR (400 MHz, CDCl₃): 1.25 (9H, s), 1.50 (3H, d), 1.54 (3H, d), 1.99 (1H, m), 2.22-2.34 (2H, m), 2.52 (1H, m), 3.29 (1H, sept), 5.27 (1H, ddd), 5.36 (1H, dd), 7.16 (1H, dd), 7.32-7.41 (3H, m), 7.49 (1H, d), 7.52 (1H, d), 7.75 (1H, dd), 8.64 (1H, d), 8.76 (1H, s).

Example 9

1-(1-tert-Butyl-1H-pyrazol-4-yl)-3-[(1S,4S)-4-(3-isopropyl-[1,2,4]triazolo[4,3-a]pyridin-6-yloxy)-1,2,3,4-tetrahydro-naphthalen-1-yl]-urea

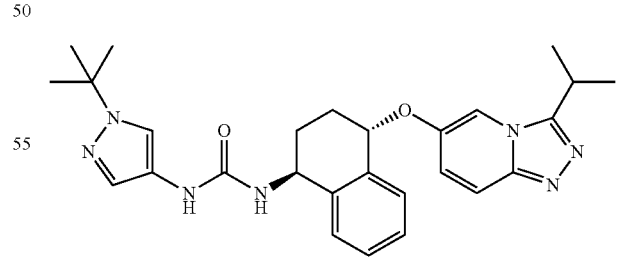

The title compound was prepared starting from 1-tert-butyl-1H-pyrazol-4-amine (Enamine) using analogous procedures to those described for Example 5. LCMS (Method 5): Rt 3.50 min, m/z 488 [MH⁺]; ¹H NMR (400 MHz, CDCl₃): 1.46 (3H, d), 1.49 (3H, d), 1.56 (9H, s), 1.89 (1H, m), 2.10-2.27 (2H, m), 2.38 (1H, m), 3.28 (1H, sept), 5.22 (1H, ddd), 5.28 (1H, dd), 5.49 (1H, br s), 6.63 (1H, br s), 7.14 (1H, dd), 7.26-7.36 (3H, m), 7.39 (1H, d), 7.45 (1H, d), 7.48 (1H, m), 7.60 (1H, d), 7.71 (1H, s).

Example 10

1-[5-tert-Butyl-2-(2-hydroxy-ethyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea

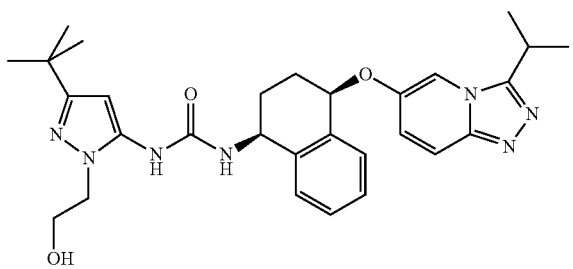 [SMILES: CC(C)c1nnc2ccc(O[C@@H]3CC[C@H](NC(=O)Nc4cc(C(C)(C)C)nn4CCO)c4ccccc43)cn12]

a. 2-(5-Amino-3-tert-butyl-pyrazol-1-yl)-ethanol (Intermediate 10a)

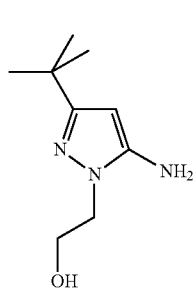

A solution of 4,4-dimethyl-3-oxo-pentanenitrile (5.00 g, 40.0 mmol), concentrated HCl (0.1 mL), and 2-hydrazino ethanol (2.98 mL, 44.0 mmol) in ethanol (40 mL) was refluxed for 20 h. The reaction mixture was then concentrated in vacuo. The resulting oily solid was washed with cyclohexane (30 mL), and dissolved in MeOH (5 mL) and H$_2$O (5 mL) and lyophilised to give the title compound as a white powder (7.13 g, 97%). LCMS (Method 3): Rt 0.43 min, m/z 184 [MH$^+$].

b. 5-tert-Butyl-2-[2-(tert-butyl-dimethyl-silanyloxy)-ethyl]-2H-pyrazol-3-ylamine (Intermediate 10b)

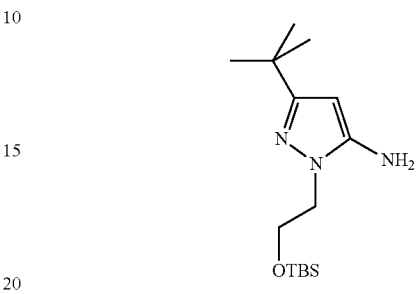

A solution of Intermediate 10a (1.00 g, 5.46 mmol), tert-butyl-dimethyl-chlorosilane (823 mg. 5.46 mmol), and imidazole (774 mg, 11.38 mmol) in DMF (9 mL) was stirred at RT under a nitrogen atmosphere for 18 h. Additional tert-butyl-dimethyl-chlorosilane (823 mg. 5.46 mmol) and imidazole (774 mg, 11.38 mmol) were added to the reaction mixture and stirred for 6 h. The reaction mixture was diluted with NH$_4$Cl saturated aqueous solution (10 mL) and DCM (10 mL). The layers were separated and aqueous layer was extracted with DCM (3×10 mL). The combined organic layers were dried (MgSO$_4$), filtered, concentrated in vacuo and purified by FCC, using 0-50% EtOAc in cyclohexane, to give the title compound (1.15 g, 70%). LCMS (Method 3): Rt 3.06, 3.23 min, m/z 298 [MH$^+$].

c. {5-tert-Butyl-2-[2-(tert-butyl-dimethyl-silanyloxy)-ethyl]-2H-pyrazol-3-yl}-carbamic acid 2,2,2-trichloro-ethyl ester (Intermediate 10c)

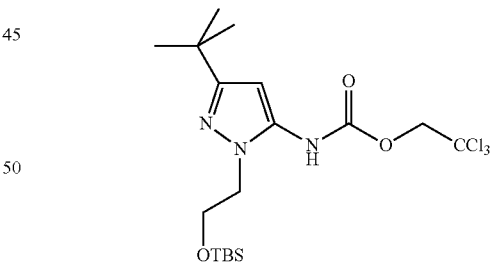

To a solution of Intermediate 10b (1.14 g, 3.85 mmol) and Et$_3$N (0.80 mL, 5.77 mmol) in THF (38 mL), 2,2,2-trichloro chloroformate (583 μL, 4.23 mmol) was added dropwise at 0° C. and then warmed to RT over 1 h. The reaction mixture was left to stand for a further 18 h. The mixture was diluted NH$_4$Cl saturated aqueous solution (10 mL) and DCM (10 mL). The layers were separated and aqueous layer was extracted with DCM (3×10 mL). The combined organic layers were dried (MgSO$_4$), filtered, concentrated in vacuo and purified three times by FCC, using 0-30% EtOAc in cyclohexane, to give the title compound as a yellow oil (354 mg, 19%). Rf=0.6 (50% EtOAc in cyclohexane); $^1$H NMR (300 MHz, CDCl$_3$):

0.02 (s, 6H), 0.81 (s, 9H), 1.23 (s, 9H), 3.88 (t, J=4.5 Hz, 2H), 4.15 (t, J=4.5 Hz, 2H), 4.77 (s, 2H), 6.16 (s, 1H), 8.30 (br s, 1H).

d. 1-{5-tert-Butyl-2-[2-(tert-butyl-dimethyl-silanyloxy)-ethyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea (Intermediate 10d)

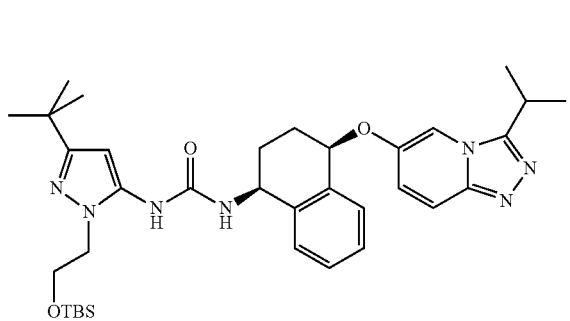 [SMILES: CC(C)c1nnc2ccc(O[C@@H]3CC[C@H](NC(=O)Nc4cc(C(C)(C)C)nn4CCO[Si](C)(C)C(C)(C)C)c4ccccc43)cn12]

A solution of Intermediate 10c (176 mg, 0.37 mmol), Intermediate 1g (100 mg, 0.31 mmol), and DIPEA (0.16 mL, 0.93 mmol) in THF (2 mL) was heated at 60° C. for 19 h. The reaction mixture was diluted with H₂O (5 mL) and DCM (5 mL). The layers were separated, and aqueous layer was extracted with DCM (3×5 mL). The combined organic layers were dried (MgSO₄), filtered, concentrated in vacuo and then purified by FCC, using 0-5% [2M NH₃ in MeOH] in DCM, to give the title compound as a white powder (108 mg, 19%). Rf=0.4 (5% [2M NH₃ in MeOH] in DCM); LCMS (Method 3): Rt 4.27 min, m/z 646 [MH⁺].

e.1-[5-tert-Butyl-2-(2-hydroxy-ethyl)-2H-pyrazol-3-yl]-3-[(1S,4R)-4-(3-isopropyl[1,2,4]triazolo[4,3-a]pyridin-6-yloxy)-1,2,3,4-tetrahydro-naphthalen-1-yl]-urea (Example 10)

To a solution of Intermediate 10d (100 mg, 0.15 mmol) in THF (2 mL), TBAF (1M in THF, 0.23 mL, 0.23 mmol) was added at RT and stirred for 10 min. The reaction mixture was diluted with H₂O (5 mL) and DCM (5 mL). The layers were separated, and aqueous layer was extracted with DCM (3×5 mL). The combined organic layers were dried (MgSO₄), filtered, concentrated in vacuo and then purified by FCC using 0-5% [2M NH₃ in MeOH] in DCM). The residue was washed with water and purified by HPLC (30%-100% MeCN in H₂O, 0.1% formic acid) to give the title compound as a white powder (47 mg, 57%). Rf=0.2 (5% [2M NH₃ in MeOH] in DCM) LCMS (Method 5): Rt 3.59 min, m/z 532 [MH⁺]. ¹H NMR (400 MHz, CDCl₃): ¹H NMR (300 MHz, CDCl₃): 1.25 (s, 9H), 1.43 (d, J=6.9 Hz, 3H), 1.46 (d, J=6.9 Hz, 3H), 1.92-2.30 (m, 4H), 3.25 (p, J=6.9 Hz, 1H), 3.95 (t, J=4.7 Hz, 2H), 4.15 (dd, J=5.3, 3.5 Hz, 2H), 5.09-5.16 (m, 1H), 5.92 (d, J=8.0 Hz, 1H), 6.12 (s, 1H), 6.92 (dd, J=9.8, 1.9 Hz, 1H), 7.22-7.27 (m, 2H), 7.33 (td, J=5.8, 3.0 Hz, 1H), 7.40 (s, 1H), 7.43 (br s, 2H), 7.47 (d, J=7.8 Hz, 1H), 7.70 (s, 1H).

Example 11

1-[5-tert-Butyl-2-(4-hydroxymethyl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea

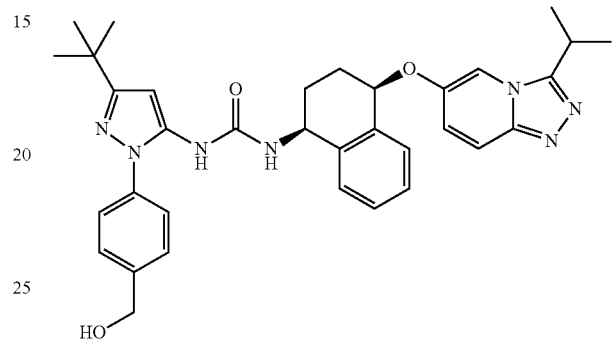

The title compound was prepared starting from [4-(5-Amino-3-tert-butyl-1H-pyrazol-1-yl)phenyl]methanol (for reference procedure see WO 2011/070368, which is incorporated herein by reference in its entirety) using analogous procedures to those described in Example 3. LCMS (Method 5): Rt 4.01 min, m/z 594.2 [MH⁺]; ¹H NMR (400 MHz, CDCl₃): 1.30 (9H, s), 1.37-1.40 (3H, d, J=6.9 Hz), 1.40-1.43 (3H, d, J=6.9 Hz), 1.84-1.96 (1H, m), 2.00-2.10 (2H, m), 2.16-2.25 (1H, m), 3.17-3.24 (1H, sp, J=6.9 Hz), 4.60 (2H, s), 5.01-5.09 (1H, td, J 9.0, 5.6 Hz), 5.14-5.19 (1H, t, J=3.9 Hz), 5.70-5.78 (1H, br s), 6.32 (1H, s), 6.86 (1H, br s), 6.95 (1H, dd, J 9.8, 2.0 Hz), 7.23-7.31 (5H, m), 7.39-7.46 (4H, m).

Example 12

1-{5-tert-Butyl-2-[3-(4,4-difluoro-piperidin-1-ylmethyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea

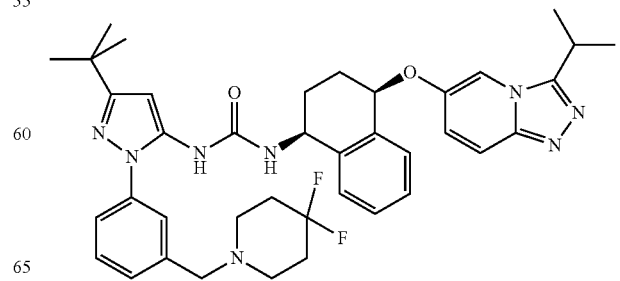

a. 1-(3-Bromo-benzyl)-4,4-difluoro-piperidine (Intermediate 12a)

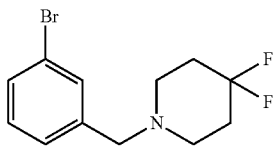 [SMILES: FC1(F)CCN(Cc2cccc(Br)c2)CC1]

A mixture of 3-bromobenzyl bromide (3.43 g, 13.73 mmol), 4,4-difluoro-piperidine hydrochloride (2.20 g, 13.97 mmol), and potassium carbonate (4.82 g, 34.86 mmol) in acetonitrile (50 mL) was stirred at RT for 16 h. The mixture was filtered and evaporated, and the residue partitioned between water (30 mL) and EtOAc (3×30 mL). The combined organic extracts were washed with water (2×50 mL) and dried (Na$_2$SO$_4$). The solvent was evaporated to give the title compound as a colourless oil (3.96 g, 99%). LCMS (Method 1): Rt 1.89 min, m/z 290/292 [MH$^+$].

b. Di-tert-butyl 1-{3-[(4,4-difluoropiperidin-1-yl)methyl]phenyl}hydrazine-1,2-dicarboxylate (Intermediate 12b)

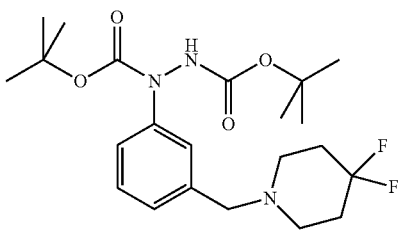 [SMILES: CC(C)(C)OC(=O)NN(C(=O)OC(C)(C)C)c1cccc(CN2CCC(F)(F)CC2)c1]

n-Butyllithium (1.6 M in hexanes, 4.5 mL, 7.28 mmol) was added dropwise to a stirred solution of Intermediate 12a (1.98 g, 6.82 mmol) in dry THF (15 mL) at −78° C. under nitrogen. The mixture was stirred at −78° C. for 10 min, then di-tert-butyl azodicarboxylate (1.73 g, 7.51 mmol) was added in one portion. The mixture was stirred at −78° C. for 20 min, then allowed to warm to RT over 20 min. The mixture was then partitioned between saturated ammonium chloride solution (15 mL) and ethyl acetate (3×20 mL). The combined organic extracts were washed with brine (20 mL) and dried (Na$_2$SO$_4$). The solvent was evaporated and the residue purified by FCC, eluting with 0-100% EtOAc in pentane, to give the title compound as a pale yellow oil (1.30 g, 43%). LCMS (Method 1): Rt 2.54 min, m/z 442 [MH$^+$].

c. 5-tert-Butyl-2-[3-(4,4-difluoro-piperidin-1-ylmethyl)-phenyl]-2H-pyrazol-3-ylamine. (Intermediate 12c)

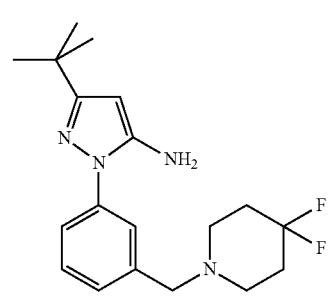 [SMILES: CC(C)(C)c1cc(N)n(-c2cccc(CN3CCC(F)(F)CC3)c2)n1]

A mixture of Intermediate 12b (1.30 g, 2.94 mmol), pivaloyl acetonitrile (0.37 g, 2.94 mmol), and concentrated HCl (1.5 mL) in ethanol (10 mL) was heated under reflux for 3 h. The cooled mixture was taken to ca. pH 7 with aqueous saturated NaHCO$_3$, and the mixture partitioned between water (15 mL) and EtOAc (3×15 mL). The combined organic extracts were washed with brine (20 mL) and dried (Na$_2$SO$_4$). The solvent was evaporated, and the residue purified by FCC, eluting with 0-100% EtOAc in pentane, to give the title compound as a pale yellow solid (450 mg, 43%). LCMS (Method 1): Rt 1.93 min, m/z 349 [MH$^+$].

d. {5-tert-Butyl-2-[3-(4,4-difluoro-piperidin-1-ylmethyl)-phenyl]-2H-pyrazol-3-yl}-carbamic acid 2,2,2-trichloro-ethyl ester. (Intermediate 12d)

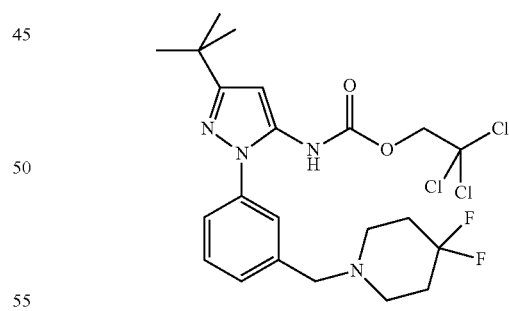

2,2,2-Trichloroethyl chloroformate (0.077 mL, 0.57 mmol) was added to a solution of Intermediate 12c (200 mg, 0.57 mmol) and DIPEA (0.31 mL, 1.81 mmol) in THF (5 mL), and the mixture stirred for 3 h. The mixture was then partitioned between water (10 mL) and EtOAc (3×15 mL), and the combined organic extracts dried (Na$_2$SO$_4$). The solvent was evaporated and the residue triturated under pentane and filtered to give the title compound as a yellow solid (215 mg, 72%). LCMS (Method 1): Rt 2.89 min, m/z 523/525 [MH$^+$]

e. 1-{5-tert-Butyl-2-[3-(4,4-difluoro-piperidin-1-ylmethyl)-phenyl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea. (Example 12)

The title compound was prepared using Intermediate 12d and Intermediate 1g in an analogous procedure to that described in Example 1 step h. LCMS (Method 5): Rt 2.52 min, m/z 697 [MH$^+$]; $^1$H NMR (300 MHz, CDCl$_3$): 1.33 (9H, s), 1.48 (6H, dd, J 7.0, 13.0 Hz), 1.90-2.15 (8H, m), 2.24-2.31 (1H, m), 2.56 (4H, br s), 3.21-3.31 (1H, m), 3.59 (2H, br s), 5.06-5.13 (1H, m), 5.18-5.21 (1H, m), 5.34 (1H, br s), 6.30 (1H, br s), 6.36 (1H, br s), 7.03-7.06 (1H, m), 7.29 (4H, br s), 7.39-7.47 (3H, m), 7.53 (1H, br s), 7.62-7.65 (1H, m).

Example 13

1-(5-tert-Butyl-2-{4-[2-(4-methyl-piperazin-1-yl)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea, formic acid salt

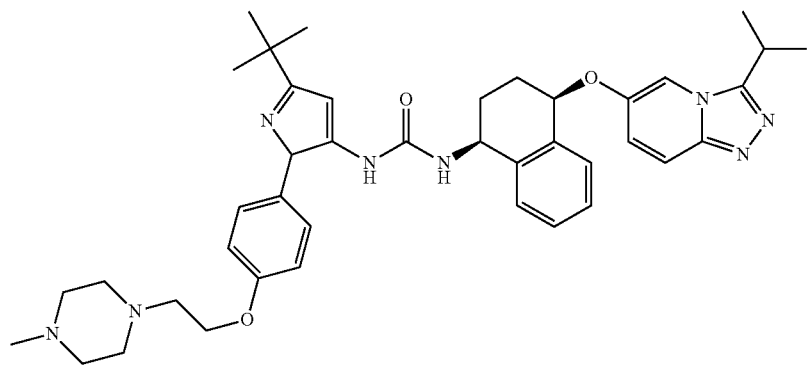 [SMILES: CC(C)c1nnc2ccc(O[C@@H]3CC[C@H](NC(=O)NC4=CC(C(C)(C)C)=NC4c4ccc(OCCN5CCN(C)CC5)cc4)c4ccccc43)cn12]

a. 5-tert-Butyl-2-(4-methoxy-phenyl)-2H-pyrazol-3-ylamine (Intermediate 13a)

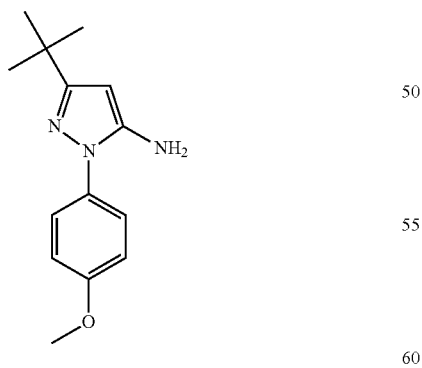

4,4-Dimethyl-3-oxo-pentanenitrile (14.28 g, 114 mmol) and 4-methoxyphenyl hydrazine (19.89 g, 114 mmol) were dissolved in a mixture of absolute ethanol (170 mL) and glacial acetic acid (5.0 mL) then heated to reflux for 3 h, before allowing to standing overnight at RT. The resulting red/brown solid was filtered off, and the filtrate was then diluted with water (500 mL), and basified with 880 ammonia solution until the pH=5. This aqueous solution was extracted into diethyl ether (3×). The combined organics were dried (MgSO₄) and evaporated in vacuo to a brown oil. Trituration (pentane) gave the title compound as a light purple/brown solid (23.07 g, 94.1 mmol, 82%). LCMS (method 1): Rt 2.87 min, m/z 246/247 [MH⁺].

b. 4-(5-Amino-3-tert-butyl-pyrazol-1-yl)-phenol (Intermediate 13b)

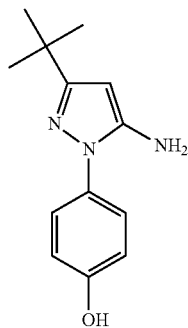 [SMILES: CC(C)(C)c1cc(N)n(-c2ccc(O)cc2)n1]

Intermediate 13a (10.0 g, 40.8 mmol) was dissolved in DCM (80.0 mL), and aluminium trichloride (28.0 g, 204.0 mmol) was added portionwise. The reaction was heated to reflux for 4 h. Additional aluminium trichloride (28.0 g, 204.0 mmol) was added portionwise, and the reaction heated at reflux overnight. After cooling, the mixture was carefully added portionwise to saturated aqueous NaHCO₃ (300 mL). The mixture was extracted with ethyl acetate (300 mL) and separated. The aqueous layer was filtered under vacuo and acidified with 1N HCl until pH=7. This aqueous layer was then re-extracted into ethyl acetate, and the organic extracts were dried (MgSO₄) and evaporated in vacuo. Purification by FCC, using 0-40% EtOAc in DCM, gave the title compound (5.0 g, 21.6 mmol, 53%). LCMS (method 1): Rt 2.77 min, m/z 232/233 [MH⁺].

c. 5-tert-Butyl-2-{4-[2-(4-methyl-piperazin-1-yl)-ethoxy]-phenyl}-2H-pyrazol-3-ylamine (Intermediate 13c)

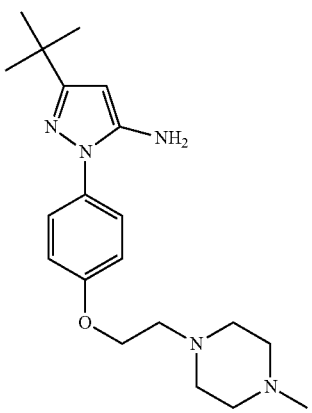 [SMILES: CN1CCN(CCOc2ccc(-n3nc(C(C)(C)C)cc3N)cc2)CC1]

To a solution of Intermediate 13b (1.15 g, 5.0 mmol), 2-(4-methyl-piperazin-1-yl)-ethanol (864 mg, 6.0 mmol), and triphenylphosphine (2.62 g, 10.0 mmol) in THF (10 mL), was added diisopropyl azodicarboxylate (2.0 g, 10.0 mmol) dropwise and stirred for 75 min. The mixture was diluted with diethyl ether (50 mL) and extracted with 10% aqueous citric acid soln (2×). The combined aqueous layers were basified with solid potassium carbonate until pH=9. The aqueous layer was then extracted with ethyl acetate (3×). The combined ethyl acetate layers were washed with brine, dried (NaSO₄) and evaporated in vacuo. Purification by FCC using 0-12% [9:1 MeOH/880 ammonia] in DCM. The resulting product was crystallised (diethyl ether) to give the title compound (270 mg, 0.756 mmol, 15%). LCMS (Method 1): Rt 2.31, 1.72 min, m/z 358/359 [MH⁺].

d. (5-tert-Butyl-2-{4-[2-(4-methyl-piperazin-1-yl)-ethoxy]-phenyl}-2H-pyrazol-3-yl)-N,N-bis-carbamic acid 2,2,2-trichloro-ethyl ester (Intermediate 13d)

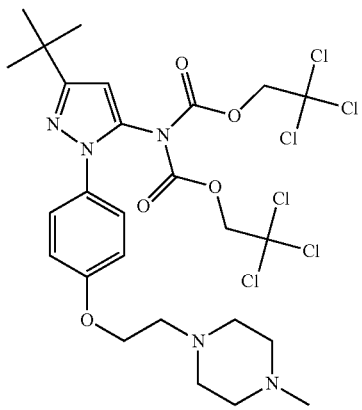 [SMILES: CN1CCN(CCOc2ccc(-n3nc(C(C)(C)C)cc3N(C(=O)OCC(Cl)(Cl)Cl)C(=O)OCC(Cl)(Cl)Cl)cc2)CC1]

Trichloroethylchloroformate (144 mg, 0.68 mmol) was added dropwise to a solution of Intermediate 13c (115 mg, 0.34 mmol) and diisopropylethylamine (129 mg, 1.0 mmol) in THF (4 mL) and stirred for 2 h. This mixture was diluted with ethyl acetate (25 mL) and washed with water, brine and dried (MgSO₄) and evaporated in vacuo to gave the title compound (240 mg, 0.34 mmol, 100%). LCMS (method 1): Rt 3.02 min, m/z 708 [MH⁺].

e. 1-(5-tert-Butyl-2-{4-[2-(4-methyl-piperazin-1-yl)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea, formic acid salt (Example 13)

Intermediate 1g (95 mg, 0.295 mmol) and Intermediate 13d (175 mg, 0.33 mmol) in a mixture of DMF (0.50 mL) and diisopropylethylamine (110 mg, 0.85 mmol) were heated to 60° C. for 3 h. The solution was loaded onto an SCX-2 cartridge, washing with MeOH and eluting with 2M NH₃ in MeOH. The resulting residue was purified by HPLC (C18 X-select column, 10-30% MeCN in H₂O, 0.1% formic acid) to give the title compound (15 mg, 6.4%). LCMS (Method 5): Rt 3.34 mins, m/z=706.4 [MH⁺]. ¹H NMR (400 MHz, CDCl₃): 1.34 (9H, s), 1.48 (6H, dd, J 7.0, 16.4 Hz), 1.90-2.30 (4H, m), 2.40 (3H, s), 2.75 (8H, br s), 2.91 (2H, t, J=5.3 Hz), 3.28 (1H, m), 4.11 (2H, t, J=5.3 Hz), 5.10 (1H, m), 5.20 (1H, t, J=4.0 Hz), 6.16 (1H, br d), 6.39 (1H, s), 6.89 (2H, d, J=9.0

Hz), 7.04 (1H, dd, J 2.1, 10.0 Hz), 7.18 (1H, br s), 7.25-7.34 (2H, m), 7.36-7.40 (3H, m), 7.47 (1H, m), 7.60 (1H, d, J=10.1 Hz), 8.14 (1H, br s).

Example 14

1-[5-tert-Butyl-2-(4-cyano-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea

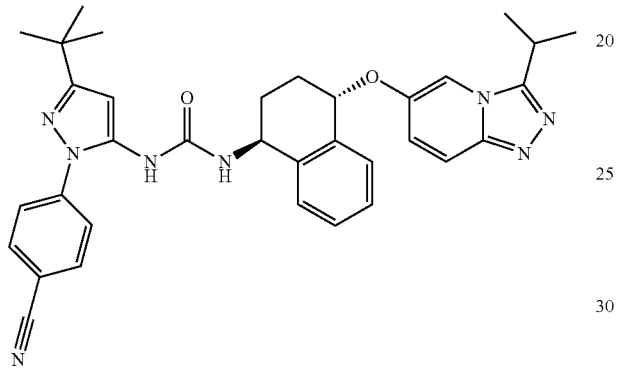

a. 4-(5-Amino-3-tert-butyl-pyrazol-1-yl)-benzonitrile (Intermediate 14a)

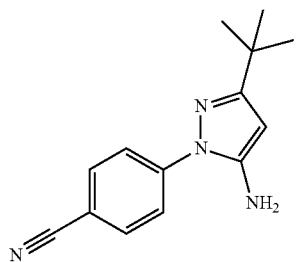 [SMILES: CC(C)(C)c1cc(N)n(-c2ccc(C#N)cc2)n1]

A cream suspension of 4-cyanophenylhydrazine hydrochloride (1.70 g, 10.0 mmol) and 4,4-dimethyl-3-oxopentanenitrile (1.31 g, 10.5 mmol) in EtOH (25 mL) was stirred at reflux for 4 h, then at RT for 64 h, and again at reflux for 24 h. The solution was cooled to RT, concentrated in vacuo, and partitioned between water (50 mL) and EtOAc (75 mL). The organics were washed with brine (50 mL), dried (Na$_2$SO$_4$), filtered and concentrated in vacuo to leave an orange solid (2.28 g, 95%). LCMS (Method 3): Rt 3.45 min, m/z 241 [MH$^+$].

b. [5-tert-Butyl-2-(4-cyano-phenyl)-2H-pyrazol-3-yl]-carbamic acid 2,2,2-trichloro-ethyl ester (Intermediate 14b)

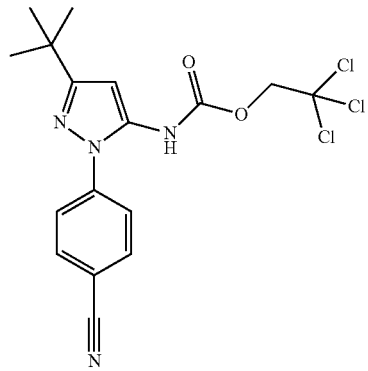 [SMILES: CC(C)(C)c1cc(NC(=O)OCC(Cl)(Cl)Cl)n(-c2ccc(C#N)cc2)n1]

To a suspension of Intermediate 14a (2.28 g, 9.49 mmol) in EtOAc (25 mL) and aq. NaOH solution (1M, 23.7 mL, 23.7 mmol) was added 2,2,2-trichloroethyl chloroformate (1.57 mL, 11.4 mmol) dropwise over 2 min. A precipitate formed which redissolved after 15 min, then the orange solution was stirred at RT for 90 min. 2,2,2-Trichloroethyl chloroformate (0.391 mL, 2.85 mmol) was added, and the orange mixture stirred at RT for 16 h. The layers were separated, and the aqueous extracted with EtOAc (25 mL). The combined organics were washed with brine (25 mL), dried (Na$_2$SO$_4$), filtered and concentrated in vacuo to leave an orange-red oil. Recrystallisation from cyclohexane gave an off-white solid (3.12 g, 79%). LCMS (Method 3): Rt 4.46 min, m/z 415, 417 [MH$^+$].

c. 1-[5-tert-Butyl-2-(4-cyano-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea. (Example 14)

A solution of Intermediate 14b (61.6 mg, 0.148 mmol), Intermediate 5c (43.4 mg, 0.135 mmol), and DIPEA (0.029 mL, 0.169 mmol) in dioxane-DMF (3:1, 2.0 mL) was stirred at 60° C. for 18 h. Water (3 mL) was added, then the mixture extracted with DCM-MeOH (9:1, 2×3 mL). The combined organics were passed through a hydrophobic frit and concentrated in vacuo to leave an orange oil. FCC, using 2-8% MeOH in DCM, gave the title compound as a white solid after freeze-drying (35.0 mg, 44%). LCMS (Method 5): Rt 4.46 min, m/z 589 [MH$^+$]. $^1$H NMR (400 MHz, d$_6$-DMSO): 1.28 (9H, s), 1.37 (3H, d, J 7.1), 1.39 (3H, d, J 7.1), 1.75 (1H, m), 2.01 (1H, m), 2.09-2.22 (2H, m), 3.57 (1H, sept, J 6.9), 4.88 (1H, m), 5.58 (1H, t, J 4.5), 6.38 (1H, s), 7.06 (1H, d, J 8.2), 7.23 (1H, dd, J 9.9, 2.2), 7.27 (1H, d, J 7.3), 7.29-7.38 (2H, m), 7.42 (1H, d, J 7.5), 7.69 (1H, dd, J 9.9, 0.9), 7.75 (2H, d, J 8.9), 7.96 (2H, d, J 8.7), 8.21 (2H, s).

Example 15

1-[5-tert-Butyl-2-(4-hydroxymethyl-phenyl)-2H-pyrazol-3-yl]-3-[(1S,4S)-4-(3-isopropyl-[1,2,4]triazolo[4,3-a]pyridin-6-yloxy)-1,2,3,4-tetrahydro-naphthalen-1-yl]-urea

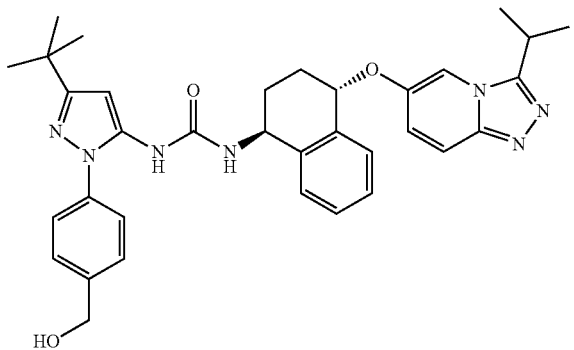 [SMILES: CC(C)c1nnc2ccc(O[C@H]3CC[C@H](NC(=O)Nc4cc(C(C)(C)C)nn4-c4ccc(CO)cc4)c4ccccc43)cn12]

The title compound was prepared starting from [4-(5-amino-3-tert-butyl-1H-pyrazol-1-yl)phenyl]methanol (for reference procedure see WO 2011/070368, which is incorporated herein by reference in its entirety) using analogous procedures to those described in Example 5. LCMS (Method 5): Rt 4.01 min, m/z 594.2 [MH$^+$]. $^1$H NMR (400 MHz, d$_6$-DMSO): 1.27 (9H, s), 1.37 (3H, d, J 7.2), 1.38 (3H, d, J 7.2), 1.74 (1H, m), 2.01 (1H, m), 2.11-2.16 (2H, m), 3.56 (1H, m), 4.55 (2H, d, J 3.1), 4.89 (1H, m), 5.29 (1H, s), 5.57 (1H, t, J 3.9), 6.33 (1H, s), 7.04 (1H, d, J 8.1), 7.22 (1H, dd, J 9.9, 2.1), 7.35-7.44 (8H, m), 7.68 (1H, m), 8.02 (1H, s), 8.21 (1H, d, J 2.0).

Example 16

1-(5-tert-Butyl-2-piperidin-4-yl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea

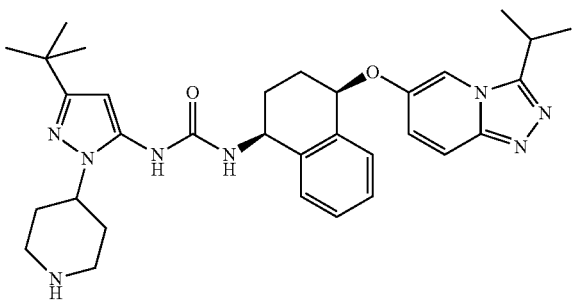 [SMILES: CC(C)c1nnc2ccc(O[C@@H]3CC[C@H](NC(=O)Nc4cc(C(C)(C)C)nn4C4CCNCC4)c4ccccc43)cn12]

a. 4-Hydrazino-piperidine-1-carboxylic acid benzyl ester (Intermediate 16a)

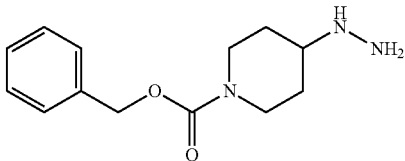 [SMILES: NNC1CCN(C(=O)OCc2ccccc2)CC1]

A solution of 1-CBZ-4-piperidone (2.92 g, 12.5 mmol) and hydrazine hydrate (2.01 mL, 18.8 mmol) in MeOH (25 mL) was stirred at 50° C. for 30 min, then cooled to RT and NaBH$_4$ (1.18 g, 31.3 mmol) added (CARE: gas evolution and exotherm to ~45° C.). The solution was stirred at RT for 30 min, then 50° C. for 18 h. The cooled solution was concentrated in vacuo, suspended in water (25 mL) and extracted with DCM (2×25 mL). The combined organics were passed through a hydrophobic frit and concentrated in vacuo to leave a clear oil. FCC, using 0-10% [2H NH$_3$ in MeOH] in DCM, gave the title compound as a clear oil (1.80 g, 58%). LCMS (Method 3): Rt 2.03 min, m/z 250 [MH$^+$].

b. 4-(5-Amino-3-tert-butyl-pyrazol-1-yl)-piperidine-1-carboxylic acid benzyl ester (Intermediate 16b)

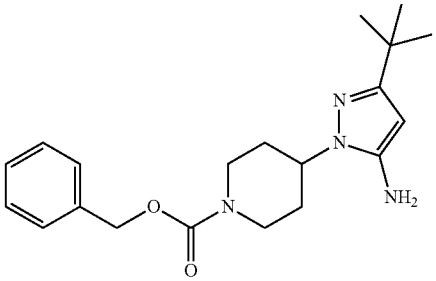 [SMILES: CC(C)(C)c1cc(N)n(C2CCN(C(=O)OCc3ccccc3)CC2)n1]

A yellow solution of Intermediate 16a (1.80 g, 7.22 mmol), 4,4-dimethyl-3-oxopentanenitrile (1.08 g, 8.66 mmol), and HCl (4M in dioxane, 2.70 mL, 10.8 mmol) in EtOH (25 mL) was stirred at reflux for 4 h. The cooled solution was applied to an SCX-2 cartridge (50 g), washed with MeOH (100 mL). The product was eluted with 2M NH$_3$ in MeOH (100 mL); concentration in vacuo left a yellow oil (772 mg). FCC, using 0-5% MeOH in DCM, gave the title compound as a yellow gum (550 mg, 21%). LCMS (Method 3): Rt 2.88 min, m/z 357 [MH⁺].

c. 4-[3-tert-Butyl-5-(2,2,2-trichloro-ethoxycarbonylamino)-pyrazol-1-yl]-piperidine-1-carboxylic acid benzyl ester (Intermediate 16c)

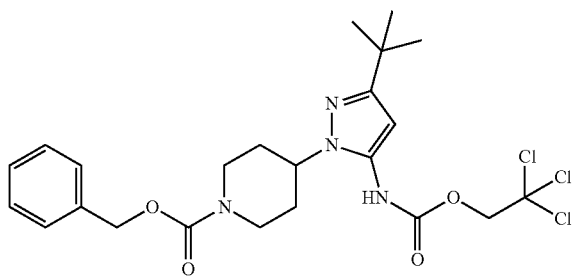 [SMILES: CC(C)(C)c1cc(NC(=O)OCC(Cl)(Cl)Cl)n(C2CCN(C(=O)OCc3ccccc3)CC2)n1]

To a solution of Intermediate 16b (550 mg, 1.54 mmol) in aqueous NaOH solution (1M, 3.85 mL, 3.85 mmol) and EtOAc (5 mL) at RT, was added 2,2,2-trichloroethyl chloroformate (0.32 mL, 2.31 mmol) over 2 min, then the mixture stirred vigorously for min. The aqueous layer was extracted with EtOAc (10 mL), then the combined organics washed with brine (10 mL), dried (MgSO₄), filtered and concentrated in vacuo to leave a yellow-brown oil. FCC, using 0-30% EtOAc in cyclohexane, gave the title compound as a white foam (337 mg, 41%). LCMS (Method 3): Rt 4.81 min, m/z 531, 533 [MH⁺].

d. 4-(3-tert-Butyl-5-{3-[(1S,4R)-4-(3-isopropyl-[1,2,4]triazolo[4,3-a]pyridin-6-yloxy)-1,2,3,4-tetrahydro-naphthalen-1-yl]-ureido}-pyrazol-1-yl)-piperidine-1-carboxylic acid benzyl ester (Intermediate 16d)

A brown solution of Intermediate 16c (337 mg, 0.634 mmol), Intermediate 1g (195 mg, 0.603 mmol), and DIPEA (0.131 mL, 0.754 mmol) in DMF (5 mL) was stirred at 100° C. for 90 min. The cooled solution was concentrated in vacuo, suspended in water (5 mL) and extracted with DCM (2×5 mL). The combined organics was passed through a hydrophobic frit and concentrated in vacuo to leave a brown gum. FCC, using 4.5% MeOH in DCM, gave the title compound as a yellow-brown oil (364 mg, 86%). LCMS (Method 3): Rt 3.96 min, m/z 705 [MH⁺].

e. 1-(5-tert-Butyl-2-piperidin-4-yl-2H-pyrazol-3-yl)-3-[(1S,4R)-4-(3-isopropyl-[1,2,4]triazolo-[4,3-a]pyridin-6-yloxy)-1,2,3,4-tetrahydro-naphthalen-1-yl]-urea (Example 16)

A suspension of Intermediate 16d (165 mg, 0.234 mmol), Pd/C (10%, 16 mg), and 2M NH₃ in MeOH (0.117 mL, 0.234 mmol) in EtOH (5 mL) under N₂ was evacuated and purged with H₂ twice, then stirred at rt for 8 h. The suspension was filtered through Celite, then the filter-cake washed with EtOH (10 mL). The combined organics were concentrated in vacuo to ~0.5 mL volume, then applied to an SCX-2 cartridge (5 g) and washed with MeOH (5 mL). The product was eluted with 2M NH₃ in MeOH (25 mL); concentration in vacuo left a pale yellow solid that was triturated with diethyl ether (10 mL) to leave a buff solid (121 mg). Half of this material was purified by HPLC(XBridge C18, 25-98% MeCN in H₂O, 0.1% NH₄OH) to give the title compound as a white solid after freeze-drying (20.0 mg, 15%). LCMS (Method 5): Rt 3.16 min, m/z 571 [MH⁺]. ¹H NMR (400 MHz, d₆-DMSO): 1.16 (9H, s), 1.33 (3H, d, J 6.8), 1.35 (3H, d, J 6.8), 1.68 (2H, m), 1.79 (2H, m), 1.91 (2H, m), 2.09 (2H, m), 2.47 (2H, m), 2.98 (2H, d, J 12.3), 3.50 (1H, sept, J 6.8), 3.92 (1H, m), 4.82 (1H, m), 5.51 (1H, t, J 4.5), 5.97 (1H, s), 6.88 (1H, d, J 8.6), 7.14 (1H, dd, J 9.9, 2.1), 7.26 (1H, m), 7.31-7.38 (3H, m), 7.65 (1H, dd, J 9.8, 0.8), 8.07 (1H, br s), 8.18 (1H, d, J 2.0).

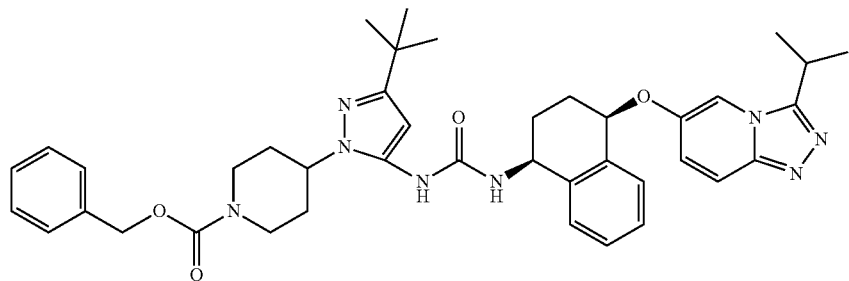 [SMILES: CC(C)c1nnc2ccc(O[C@@H]3CC[C@H](NC(=O)Nc4cc(C(C)(C)C)nn4C4CCN(C(=O)OCc5ccccc5)CC4)c4ccccc43)cn12]

Example 17

1-[5-tert-Butyl-2-(1-methyl-piperidin-4-yl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea

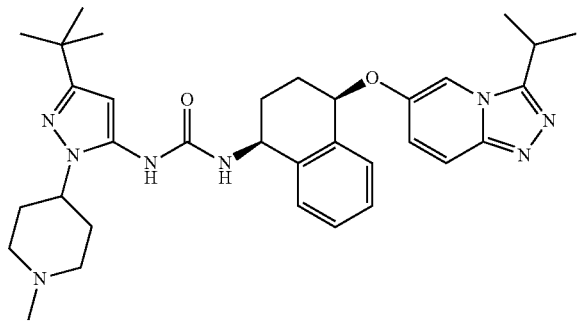 [SMILES: CC(C)c1nnc2ccc(O[C@@H]3CC[C@H](NC(=O)Nc4cc(C(C)(C)C)nn4C4CCN(C)CC4)c4ccccc43)cn12]

A mixture of Example 16 (half crude material, assume 64.8 mg, 0.114 mmol) and formaldehyde (37% in water, 0.092 mL, 1.14 mmol) in DCM (2 mL) was stirred at RT for 10 min, then AcOH (0.013 mL, 0.227 mmol) and NaBH(OAc)$_3$ (48.1 mg, 0.227 mmol) were added sequentially, and the solution stirred at RT for 3 h. The solution was concentrated in vacuo to ~0.5 mL volume, applied to an SCX-2 cartridge (2 g) and washed with MeOH (15 mL). The product was eluted with 2M NH$_3$ in MeOH (10 mL); concentration in vacuo left a pale yellow solid (82.6 mg). HPLC (XBridge C18, 30-98% MeCN in H$_2$O, 0.1% NH$_4$OH) gave the title compound as a white solid after freeze-drying (30.8 mg, 46%). LCMS (Method 5): Rt 3.18 min, m/z 585 [MH$^+$]. $^1$H NMR (400 MHz, d$_6$-DMSO): 1.21 (9H, s), 1.38 (H, d, J 6.8), 1.40 (3H, d, J 6.8), 1.75 (2H, t, J 12.2), 1.91-2.04 (6H, m), 2.07-2.17 (2H, m), 2.18 (3H, s), 2.87 (2H, d, J 10.6), 3.58 (1H, sept, J 6.8), 3.88 (1H, m), 4.88 (1H, m), 5.56 (1H, t, J 4.7), 6.02 (1H, s), 6.89 (1H, d, J 8.6), 7.19 (1H, dd, J 9.8, 2.1), 7.31 (1H, m), 7.36-7.43 (3H, m), 7.70 (1H, d, J 9.8), 8.06 (1H, s), 8.22 (1H, d, J 2.0).

Example 18

1-[5-tert-Butyl-2-(2-morpholin-4-yl-ethyl)-2H-pyrazol-3-yl]-3-[(1S,4R)-4-(3-isopropyl[1,2,4]triazolo[4,3-a]pyridin-6-yloxy)-1,2,3,4-tetrahydro-naphthalen-1-yl]-urea

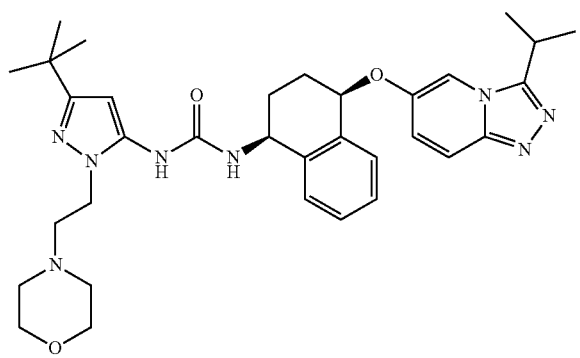 [SMILES: CC(C)c1nnc2ccc(O[C@@H]3CC[C@H](NC(=O)Nc4cc(C(C)(C)C)nn4CCN4CCOCC4)c4ccccc43)cn12]

To a stirred solution of Example 10 (136 mg, 0.26 mmol) and Et$_3$N (0.11 mL, 0.77 mmol) in DCM (2.5 mL), was added mesyl chloride (31 µL, 0.31 mmol) at 0° C. under N$_2$. After 15 min, the reaction mixture was warmed to RT. After 15 min, H$_2$O (5 mL) and DCM (5 mL) were added. The layers were separated and aqueous layer was extracted with DCM. The combined organics were dried, filtered, concentrated in vacuo. The resulting residue was dissolved in THF (2.5 mL), then DIPEA (49 µL, 0.28 mmol) and morpholine (67 µL, 0.77 mmol) added sequentially. The resulting mixture was heated at reflux for 21 h. The reaction mixture was cooled to RT, then H$_2$O (5 mL) and DCM (5 mL) were added. The layers were separated and aqueous extracted with DCM (3×5 mL). The combined organics were dried (MgSO$_4$), filtered and concentrated in vacuo. The residue was purified by FCC, using 0-10% [2M NH$_3$ in MeOH] in DCM, and then prep HPLC (Gemini C18 column, 20%-98% MeCN in H$_2$O, 0.1% HCO$_2$H, 20 min) to give the title compound as a white powder after freeze-drying (64 mg, 41%). LCMS (Method 5): Rt 3.21 min, m/z 601 [MH$^+$]. $^1$H NMR (400 MHz, CDCl$_3$): 1.22 (9H, s), 1.47 (3H, d, J 6.9), 1.50 (3H, d, J 6.9), 2.00-2.12 (3H, m), 2.25-2.31 (1H, m), 2.53-2.56 (4H, m), 2.68-2.70 (2H, m), 3.28 (1H, m), 3.80 (4H, t, J 4.7), 4.16 (2H, t, J 4.7), 5.12-5.15 (1H, m), 5.20 (1H, d, J 4.2), 5.46 (1H, d, J 8.8), 5.89 (1H, s), 7.09 (1H, dd), 7.27-7.30 (2H, m), 7.36-7.40 (1H, m), 7.45 (1H, d, J 2.0), 7.47 (1H, d, J 7.9), 7.67 (1H, dd, J 9.9, 0.8), 9.43 (1H, s).

Example 19

1-(5-tert-Butyl-2-methyl-2H-pyrazol-3-yl)-3-[(1S,4R)-7-fluoro-4-(3-isopropyl-[1,2,4]triazolo[4,3-a]pyridin-6-yloxy)-1,2,3,4-tetrahydro-naphthalen-1-yl]-urea

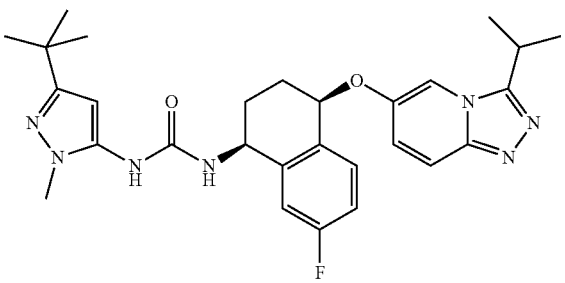 [SMILES: CC(C)c1nnc2ccc(O[C@@H]3CC[C@H](NC(=O)Nc4cc(C(C)(C)C)nn4C)c4cc(F)ccc43)cn12]

a. (1R,4S)-4-Amino-6-fluoro-1,2,3,4-tetrahydro-naphthalen-1-ol (Intermediate 19a)

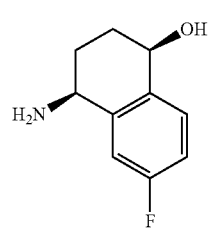 [SMILES: N[C@H]1CC[C@@H](O)c2ccc(F)cc21]

To a solution of 2,2,2-trifluoro-N-((1S,4R)-7-fluoro-4-hydroxy-1,2,3,4-tetrahydro-naphthalen-1-yl)-acetamide (synthesised in an analogous manner to that described in WO 2009/048474, which is incorporated herein by reference in its entirety) (2.31 g, 8.34 mmol) in MeOH (22.5 mL), was added a solution of sodium hydroxide (0.834 g, 20.8 mmol) in water (15 mL) and the mixture was stirred at RT for 65 h. The mixture was concentrated in vacuo, then applied to an SCX-2 cartridge (50 g), washing with methanol then eluting basic components with 0.2-1 M ammonia in methanol. Product containing fractions were combined and concentrated in vacuo. The residue was purified by FCC, using 0-10% [2M NH$_3$ in MeOH] in DCM, to give the title compound (1.29 g, 86%). $^1$H NMR (300 MHz, d$_6$-DMSO): 1.60-2.15 (6H, m), 3.62-3.71 (1H, m), 4.49 (1H, t, J 4.7), 5.15 (1H, br s), 6.98 (1H, dt, J 8.6, 2.8), 7.28 (1H, dd, J 10.7, 2.8), 7.36 (1H, dd, J 8.6, 6.2).

b. (1S,4R)-7-Fluoro-4-(3-isopropyl-[1,2,4]triazolo[4,3-a]pyridin-6-yloxy)-1,2,3,4-tetrahydronaphthalen-1-ylamine (Intermediate 19b)

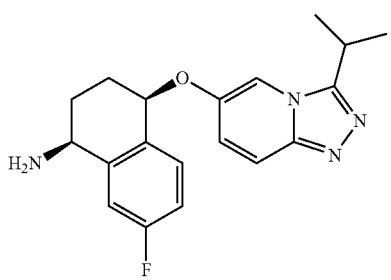 [SMILES: CC(C)c1nnc2ccc(O[C@@H]3CC[C@H](N)c4cc(F)ccc43)cn12]

Intermediate 19a (837 mg, 4.62 mmol) was dissolved in dry DMF (15 mL) under Ar, then NaH (60% in mineral oil, 556 mg, 13.9 mmol) was added, and the mixture stirred for 15 min. Intermediate 1f (893 mg, 4.99 mmol) was added, and the reaction heated at 60° C. for 2 h. The reaction was cooled, quenched by addition of water and extracted with DCM (4×30 mL). The combined organic layers were washed with brine, dried (Na$_2$SO$_4$), filtered and concentrated in vacuo. The residue was purified by FCC, eluting with 0-20% [2M NH$_3$ in MeOH] in DCM, to give the title compound (429 mg, 27%). LCMS (Method 3): Rt 1.96, m/z 363 [MNa$^+$].

c. 1-(5-tert-Butyl-2-methyl-2H-pyrazol-3-yl)-3-[(1S,4R)-7-fluoro-4-(3-isopropyl-[1,2,4]triazolo[4,3-a]pyridin-6-yloxy)-1,2,3,4-tetrahydro-naphthalen-1-yl]-urea (Example 19)

Intermediate 19b (85.0 mg, 0.250 mmol) and (5-tert-butyl-2-methyl-2H-pyrazol-3-yl)-carbamic acid 2,2,2-trichloro-ethyl ester (US2004/192653, 99 mg, 0.300 mmol) were dissolved in 1,4-dioxane (3 mL) and DIPEA (70 μL, 0.400 mmol). The reaction was heated at reflux for 1.75 h, then more (5-tert-butyl-2-methyl-2H-pyrazol-3-yl)-carbamic acid 2,2,2-trichloro-ethyl ester (35 mg, 0.100 mmol) and DIPEA (3 drops) were added. After a further 4 h the mixture was concentrated in vacuo. The residue was purified by FCC, using 0-15% MeOH in DCM, to give impure product (82 mg). Further purification twice by HPLC (C18 X-select column, 40-98% MeCN in H$_2$O, 0.1% HCO$_2$H) gave the title compound as a white powder after freeze-drying (44 mg, 34%). LCMS (Method 5): Rt 3.83 min, m/z 520.1 [MH$^+$]. $^1$H NMR (400 MHz, d$_6$-DMSO): 1.21 (9H, s), 1.35-1.43 (6H, m), 1.85-2.25 (4H, m), 3.51-3.62 (4H, m), 4.80-4.91 (1H, m), 5.50-5.57 (1H, m), 6.02 (1H, s), 7.09 (1H, d, J 8.8), 7.11-7.17 (2H, m), 7.20 (1H, dd, J 9.6, 2.2), 7.44-7.50 (1H, m), 7.69 (1H, d, J 9.6), 8.22 (1H, br d), 8.40 (1H, s).

Example 20

1-[(1S,4R)-4-(3-Isopropyl-[1,2,4]triazolo[4,3-a]pyridin-6-yloxy)-1,2,3,4-tetrahydro-naphthalen-1-yl]-3-(2-p-tolyl-2H-pyrazol-3-yl)-urea

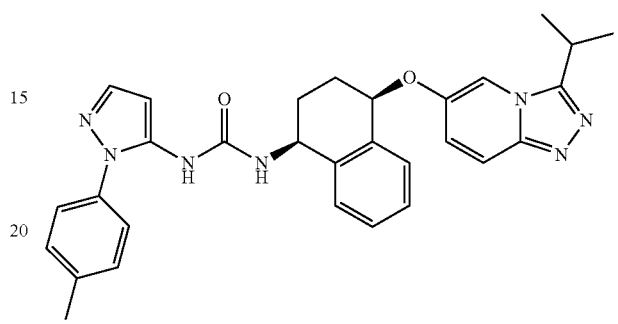

a. (2-p-Tolyl-2H-pyrazol-3-yl)-carbamic acid 2,2,2-trichloro-ethyl ester (Intermediate 20a)

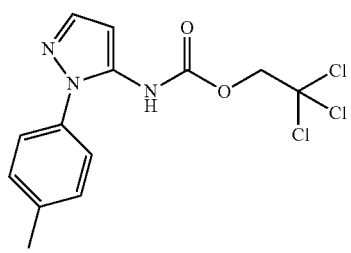 [SMILES: Cc1ccc(-n2nccc2NC(=O)OCC(Cl)(Cl)Cl)cc1]

NaOH (107 mg, 2.67 mmol) was added to a stirred solution of 2-p-tolyl-2H-pyrazol-3-ylamine (for reference procedure see WO 2009/150614, which is incorporated herein by reference in its entirety, 346 mg, 2.00 mmol) in water (1 mL) and EtOAc (4 mL). The mixture was cooled to 0° C., and 2,2,2-trichloroethyl chloroformate (385 L, 2.80 mmol) added. Stirring was continued for 30 min at 0° C. and then for 2 h at RT. The mixture was partitioned between water and EtOAc. The organic phase was washed with brine and concentrated to dryness in vacuo to give the title compound as an orange residue. LCMS (Method 3): Rt 3.90 min, m/z 348, 350 [MH$^+$].

b. 1-[(1S,4R)-4-(3-Isopropyl-[1,2,4]triazolo[4,3-a]pyridin-6-yloxy)-1,2,3,4-tetrahydro-naphthalen-1-yl]-3-(2-p-tolyl-2H-pyrazol-3-yl)-urea (Example 20)

A mixture of Intermediate 1g (50.0 mg, 0.16 mmol), Intermediate 20a (54.0 mg, 0.16 mmol), and DIPEA (54.0 μL, 0.31 mmol) in DMF (2.5 mL) was heated to 100° C. for 1 h. After cooling, the mixture was partitioned between EtOAc and water, and then extracted into EtOAc (3×). The combined organic extracts were washed with sat. aq. NaHCO$_3$ solution, brine, and evaporated in vacuo. The residue was purified by FCC, using 0-10% [2M NH$_3$ in MeOH] in DCM, to give a beige solid (30 mg). Further purification by HPLC (5-98%

MeCN in H₂O, 0.1% HCO₂H) gave the title compound as a white solid after freeze-drying (17 mg, 20%). LCMS (Method 5): Rt 3.68 min, m/z 522 [MH⁺]. ¹H NMR (400 MHz, d₆-DMSO): 1.35-1.40 (6H, m), 1.81-1.98 (2H, m), 2.02-2.15 (2H, m), 2.37 (3H, s), 3.57 (1H, sept, J 6.6), 4.83 (1H, m), 5.52 (1H, t, J 4.2), 6.40 (1H, d, J 1.8), 7.16 (1H, dd, J 9.6, 2.2), 7.21-7.42 (8H, m), 7.51 (1H, d, J 1.8), 7.67 (1H, d, J 9.6), 8.20 (1H, m), 8.29 (1H, m), 8.45 (1H, br s).

Example 21

1-(1-tert-Butyl-1H-pyrazol-4-yl)-3-[(1S,4R)-7-fluoro-4-(3-isopropyl-[1,2,4]triazolo[4,3-a]pyridin-6-yloxy)-1,2,3,4-tetrahydro-naphthalen-1-yl]-urea

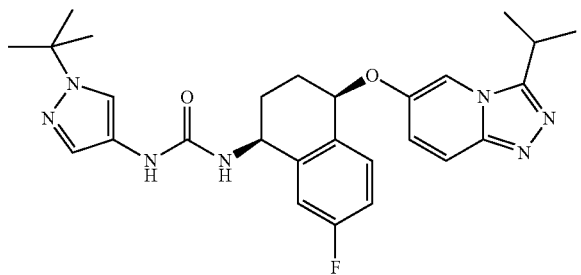 [SMILES: CC(C)c1nnc2ccc(O[C@@H]3CC[C@H](NC(=O)Nc4cnn(C(C)(C)C)c4)c4cc(F)ccc43)cn12]

The title compound was prepared starting from 1-tert-butyl-1H-pyrazol-4-amine (Enamine) and Intermediate 19b using analogous procedures to those described for Example 5. LCMS (Method 5): Rt 3.65 min, m/z 506.2 [MH⁺]. ¹H NMR (400 MHz, d₆-DMSO): 1.36-1.42 (6H, m), 1.49 (9H, s), 1.84-2.25 (4H, m), 3.57 (1H, sept, J 7.0), 4.80-4.89 (1H, m), 5.50-5.55 (1H, m), 6.72 (1H, d, J 8.8), 7.09-7.21 (3H, m), 7.37 (1H, d, J 0.8), 7.43-7.49 (1H, m), 7.69 (1H, d), 7.77 (1H, d), 8.14 (1H, s), 8.21 (1H, d).

Example 22

1-(5-tert-Butyl-2-{3-[2-(4-hydroxy-piperidin-1-yl)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea formate salt

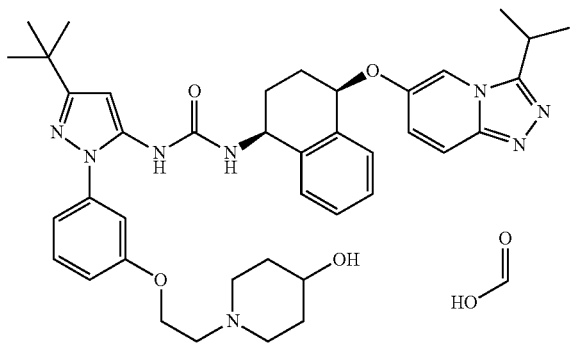 [SMILES: CC(C)c1nnc2ccc(O[C@@H]3CC[C@H](NC(=O)Nc4cc(C(C)(C)C)nn4-c4cccc(OCCN5CCC(O)CC5)c4)c4ccccc43)cn12 ; O=CO]

a. 5-tert-Butyl-2-(3-triisopropylsilanyloxy-phenyl)-2H-pyrazol-3-ylamine (Intermediate 22a)

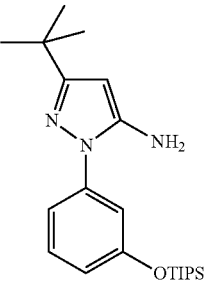

Triisopropylsilylchloride (1.02 mL, 3.96 mmol) was added to a solution of 3-(5-amino-3-tert-butyl-pyrazol-1-yl)-phenol (915 mg, 3.96 mmol) and imidazole (646 mg, 9.50 mmol) in DMF (15 mL) at 0° C. The reaction was stirred at RT over the weekend then partitioned between EtOAc and water. The aqueous layer was then extracted with EtOAc (3×). The combined organic layers were washed with brine, dried (MgSO₄), filtered and evaporated in vacuo. The residue was purified by FCC, using 0-40% EtOAc in cyclohexane, to give the title compound (1.53 g, 99%). LCMS (Method 4): Rt 4.78 min, m/z 388 [MH⁺].

b. [5-tert-Butyl-2-(3-triisopropylsilanyloxy-phenyl)-2H-pyrazol-3-yl]-carbamic acid 2,2,2-trichloro-ethyl ester (Intermediate 22b)

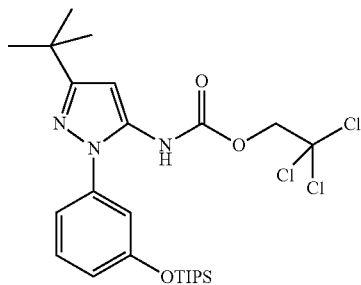

2,2,2-Trichloroethylchloroformate (1.09 mL, 7.92 mmol) was added to a solution of Intermediate 22a (1.53 g, 3.96 mmol) and DIPEA (2.75 mL, 15.8 mmol) in THF (40 mL) at 0° C. The reaction was stirred at RT for 3 h then partitioned between EtOAc and water. The aqueous layer was then extracted with EtOAc (3×). The combined organic layers were washed with brine, dried (MgSO₄), filtered and evaporated in vacuo. The residue was purified by FCC, using 0-50%

EtOAc in cyclohexane, to give the title compound (2.22 g, 99%). LCMS (Method 4): Rt 5.55 min, m/z 560, 562 [MH+].

c. 1-[5-tert-Butyl-2-(3-triisopropylsilanyloxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea (Intermediate 22c)

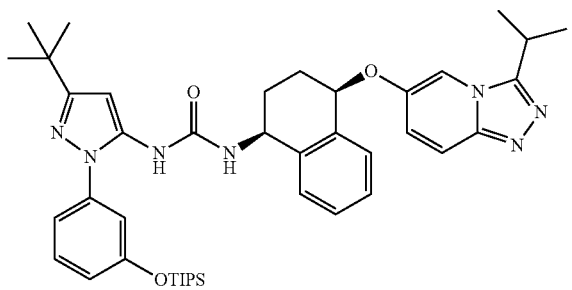

Intermediate 22b (390 mg, 0.69 mmol) was added to a solution of Intermediate 1g (223 mg, 0.69 mmol) and DIPEA (240 µL, 1.38 mmol) in 1,4-dioxane (6.0 mL). The reaction was heated to 60° C. for 3 h and heated at 45° C. overnight. The reaction was cooled and partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% MeOH in DCM, to give the title compound (258 mg, 50%). LCMS (Method 2): Rt 4.93 min, m/z 736 [MH+].

d. 1-[5-tert-Butyl-2-(3-hydroxy-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea (Intermediate 22d)

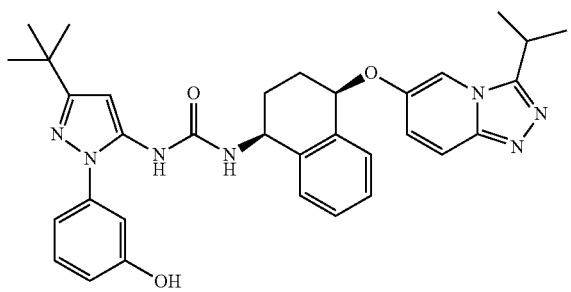 [SMILES: CC(C)c1nnc2ccc(O[C@@H]3CC[C@H](NC(=O)Nc4cc(C(C)(C)C)nn4-c4cccc(O)c4)c4ccccc43)cn12]

TBAF (1M in THF, 350 µL, 0.35 mmol) was added to a solution of Intermediate 22c (258 mg, 0.35 mmol) in THF (5.0 mL) at 0° C. The reaction was stirred for 1 h then partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% MeOH in DCM, to give the title compound as an off-white solid (150 mg, 75%). LCMS (Method 1): Rt 4.11 min, m/z 580 [MH+]. ¹H NMR (400 MHz, d₄-MeOD): 1.30 (9H, s), 1.42 (3H, d, J 6.9), 1.45 (3H, d, J 6.9), 1.88-2.16 (3H, m), 2.20-2.30 (1H, m), 3.51 (1H, sept, J 6.9), 4.90 (1H, dd, J 8.9, 5.6), 5.45 (1H, t, J 4.1), 6.33 (1H, s), 6.84 (1H, ddd, J 8.3, 2.6, 0.8), 6.88-6.94 (2H, m), 7.19-7.26 (2H, m), 7.26-7.33 (4H, m), 7.61 (1H, d, J 10.0), 8.01 (1H, s).

e. 1-(5-tert-Butyl-2-{3-[2-(4-hydroxy-piperidin-1-yl)-ethoxy]-phenyl}-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea Formate Salt (Example 22)

DIAD (51.0 µL, 0.260 mmol) was added to a solution of Intermediate 22d (75.0 mg, 0.13 mmol), 4-hydroxy-1-piperidine-ethanol (28.0 mg, 0.19 mmol), and Ph₃P (68.0 mg, 0.26 mmol) in THF (1.5 mL) at 0° C. The reaction was stirred at RT over the weekend then partitioned between EtOAc and water. The aqueous layer was extracted with EtOAc (3×). The combined organic layers were washed with brine, dried (MgSO₄), filtered and evaporated in vacuo. The residue was purified by FCC, using 0-10% [2M NH₃ in MeOH] in DCM. Further purification by HPLC (C18 X-select column, 25-98% MeCN in H₂O, 0.1% HCO₂H) gave the title compound as a white powder after freeze-drying (57 mg, 62%). LCMS (Method 5): Rt 3.32 min, m/z 707.4 [MH+]. ¹H NMR (400 MHz, d₄-MeOD): 1.31 (9H, s), 1.42 (3H, d, J 6.8), 1.45 (3H, d, J 6.8), 1.62-1.72 (2H, m), 1.86-2.04 (4H, m), 2.04-2.14 (1H, m), 2.21-2.30 (1H, m), 2.69-2.79 (2H, m), 3.11-3.19 (4H, m), 3.51 (1H, sept, J 6.9), 3.70-3.78 (1H, m), 4.26 (2H, t, J 5.3), 4.89 (1H, dd, J 8.9, 5.8), 5.45 (1H, t, J 4.1), 6.33 (1H, s), 7.05 (1H, ddd, J 8.4, 2.7, 0.8), 7.09-7.13 (2H, m), 7.19-7.25 (3H, m), 7.26-7.33 (2H, m), 7.42 (1H, t, J 8.1), 7.61 (1H, dd, J 9.7, 0.6), 8.01 (1H, d, J 1.7), 8.42 (1H, br s).

Example 23

1-[5-tert-Butyl-2-(3-morpholin-4-yl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea

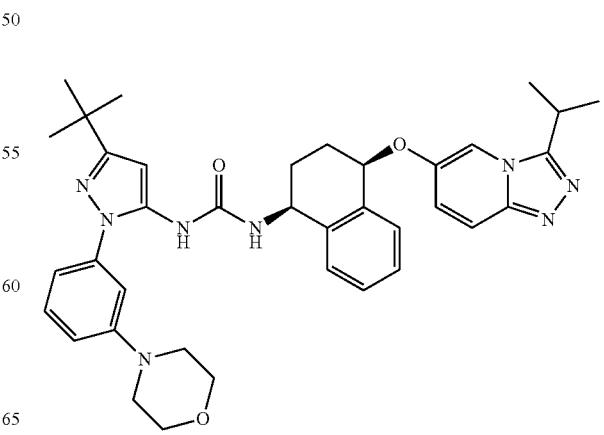

a. 2-(3-Bromo-phenyl)-5-tert-butyl-2H-pyrazol-3-ylamine (Intermediate 23a)

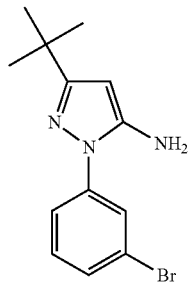 [SMILES: CC(C)(C)c1cc(N)n(-c2cccc(Br)c2)n1]

A mixture of 3-bromophenylhydrazine hydrochloride (5.00 g, 22.4 mmol) and 4,4-dimethyl-3-oxo-pentanenitrile (4.29 g, 33.6 mmol) in absolute ethanol (55 mL) was stirred at reflux for 18 h and cooled, then concentrated in vacuo. The residue was suspended in sat. aq. NaHCO$_3$ (50 mL) and extracted with EtOAc (3×50 mL). The combined organics were dried (Na$_2$SO$_4$) and concentrated in vacuo. The residue was purified by FCC, using 0-5% [2M NH$_3$ in MeOH] in DCM, to give the title compound (3.56 g, 54%). LCMS (Method 1): Rt 3.33 min, m/z 294, 296 [MH$^+$].

b. Di-tert-butyl[1-(3-bromophenyl)-3-tert-butyl-1H-pyrazol-5-yl]imidodicarbonate (Intermediate 23b)

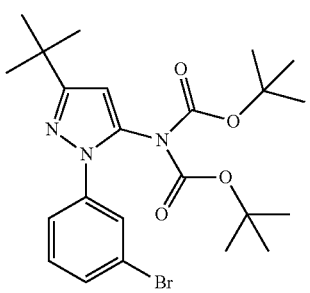 [SMILES: CC(C)(C)OC(=O)N(C(=O)OC(C)(C)C)c1cc(C(C)(C)C)nn1-c1cccc(Br)c1]

To a solution of Intermediate 23a (1.50 g, 5.10 mmol) and N,N-dimethyl-4-aminopyridine (31 mg, 0.26 mmol) in DCM (30 mL), was added di-tert-butyl dicarbonate (3.33 g, 15.3 mmol), and the mixture was stirred at RT for 20 h. The mixture was diluted with DCM, washed with water, then dried (MgSO$_4$), filtered and concentrated in vacuo. The residue was purified by FCC, using 0-2.5% MeOH in DCM, to give the title compound (1.97 g, 78%). $^1$H NMR (400 MHz, d$_4$-MeOH): 1.33 (27H, s), 6.13 (1H, s), 7.25 (1H, d J 3.9), 7.28 (1H, d J 8.0), 7.35-7.40 (1H, m), 7.41-7.47 (1H, m).

c. [5-tert-Butyl-2-(3-morpholin-4-yl-phenyl)-2H-pyrazol-3-yl]-carbamic acid tert-butyl ester (Intermediate 23c)

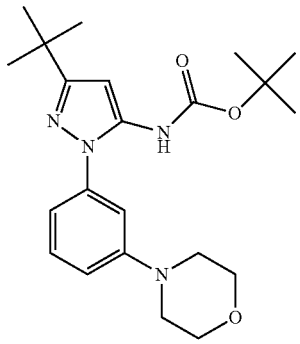 [SMILES: CC(C)(C)OC(=O)Nc1cc(C(C)(C)C)nn1-c1cccc(N2CCOCC2)c1]

A mixture of Intermediate 23b (900 mg, 1.80 mmol), morpholine (240 mg, 2.70 mmol), potassium-tert-butoxide (303 mg, 2.70 mmol), 2-dicyclohexylphosphino-2',4',6'-triisopropyl biphenyl (87 mg, 0.18 mmol), and tris(dibenzylideneacetone)dipalladium(0) (81 mg, 0.09 mmol) in THF (9 mL) was irradiated in the microwave at 100° C. for 20 min. The reaction was diluted with water and extracted with EtOAc (×2). The combined organics were washed with brine, dried (MgSO$_4$), filtered and evaporated in vacuo. The residue was purified by FCC, using 0-100% EtOAc in cyclohexane, to give the title compound (290 mg, 40%). LCMS (Method 7): Rt 3.94 min, m/z 401 [MH$^+$].

d. 5-tert-Butyl-2-(3-morpholin-4-yl-phenyl)-2H-pyrazol-3-ylamine (Intermediate 23d)

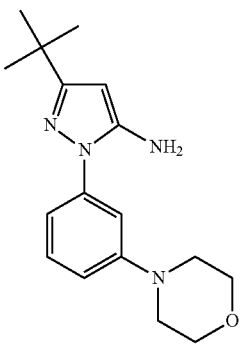 [SMILES: CC(C)(C)c1cc(N)n(-c2cccc(N3CCOCC3)c2)n1]

A solution of Intermediate 23c (290 mg, 0.725 mmol) and TFA (3 mL) in DCM (4 mL) was stirred at RT for 1 h. The reaction mixture was applied to an SCX-2 cartridge (10 g) and washed with MeOH. The product was eluted with 2M NH$_3$ in e. [5-tert-Butyl-2-(3-morpholin-4-yl-phenyl)-2H-pyrazol-3-yl]-carbamic acid 2,2,2-trichloro-ethyl ester (Intermediate 23e)

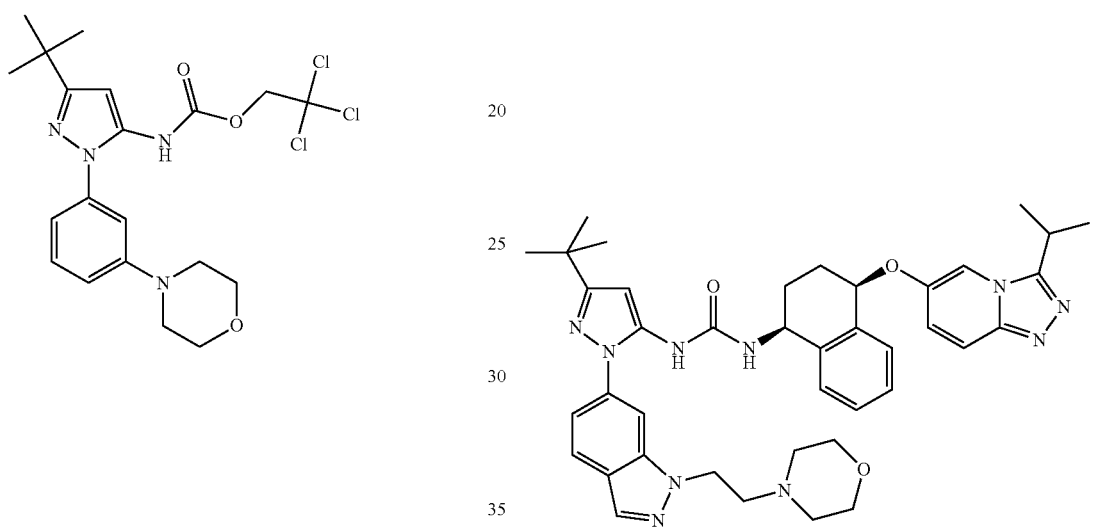

2,2,2-Trichloroethylchloroformate (175 mg, 0.82 mmol) was added dropwise to a solution of Intermediate 23d (190 mg, 0.63 mmol) and DIPEA (244 mg, 1.89 mmol) in THF (10 mL), and the mixture stirred at RT for 1.5 h. The mixture was diluted with water and extracted with EtOAc (×2). The combined organic layers were washed with brine, dried (MgSO₄), filtered and evaporated in vacuo. The residue was purified by FCC, using 0-50% EtOAc in cyclohexane, to give the title compound (140 mg, 46%). LCMS (Method 4): Rt 3.94, m/z 475 [MH⁺].

f. 1-[5-tert-Butyl-2-(3-morpholin-4-yl-phenyl)-2H-pyrazol-3-yl]-3-[(1S,4R)-4-(3-isopropyl-[1,2,4]triazolo[4,3-a]pyridin-6-yloxy)-1,2,3,4-tetrahydro-naphthalen-1-yl]-urea (Example 23)

A solution of Intermediate 1g (64 mg, 0.20 mmol), Intermediate 23e (140 mg, 0.29 mmol), and DIPEA (103 mg, 0.80 mmol) in DMF (2 mL) was stirred at 60° C. for 1 h. The reaction mixture was applied to an SCX-2 cartridge (25 g) and washed with MeOH. The product was eluted with 2M NH₃ in MeOH; concentration in vacuo gave a residue. FCC, using 0-10% [2M NH₃ in MeOH] in DCM, followed by HPLC (C6-Ph column, 10-70% MeCN in H₂O, 0.1% HCO₂H) gave the title compound as a white powder after freeze-drying (46 mg, 38%). LCMS (Method 5): Rt 4.39 min, m/z 649.2 [MH⁺]. ¹H NMR (400 MHz, d₄-MeOH): 1.30 (9H, s), 1.44 (6H, m), 1.85-2.05 (2H, m), 2.05-2.16 (1H, m), 2.19-2.29 (1H, m), 3.15 (4H, t, J 3.8), 3.47-3.56 (1H, m), 3.76 (4H, t, J 4.9), 4.86-4.92 (1H, m), 5.44 (1H, t, J 4.3), 6.32 (1H, s), 6.91 (1H, d, J 8.1), 7.00-7.05 (2H, m), 7.19-7.38 (6H, m), 7.60 (1H, d, J 9.5), 8.00 (1H, d, J 1.6).

Example 24

1-{5-tert-Butyl-2-[1-(2-morpholin-4-yl-ethyl)-1H-indazol-6-yl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea

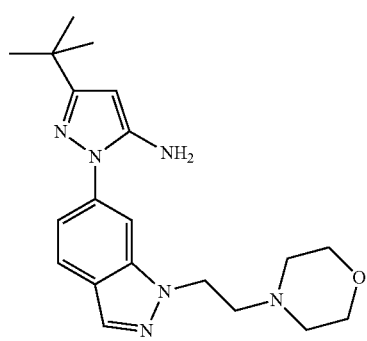

a. 5-tert-Butyl-2-[1-(2-morpholin-4-yl-ethyl)-1H-indazol-6-yl]-2H-pyrazol-3-ylamine (Intermediate 24a) and 5-tert-Butyl-2-[2-(2-morpholin-4-yl-ethyl)-2H-indazol-6-yl]-2H-pyrazol-3-ylamine (Intermediate 24b)

97
-continued

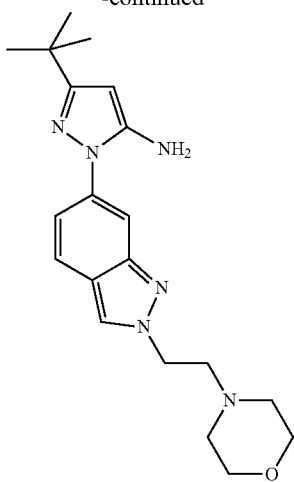

A solution of 5-tert-butyl-2-(1H-indazol-6-yl)-2H-pyrazol-3-ylamine (US2008/113967, 200 mg, 0.78 mmol) was formed in DMF (10 mL). 4-(2-chloroethyl)morpholine hydrochloride salt (160 mg, 0.86 mmol) and K$_2$CO$_3$ (276 mg, 2.0 mmol) were added, and the mixture heated at 50° C. overnight. The mixture was allowed to cool to RT then partitioned between EtOAc/water and extracted with EtOAc. The combined organics were dried over Na$_2$SO$_4$, filtered and concentrated in vacuo. Purification by FCC, using 0-10% MeOH in EtOAc, gave two products. First eluting: 5-tert-butyl-2-[1-(2-morpholin-4-yl-ethyl)-1H-indazol-6-yl]-2H-pyrazol-3-ylamine (Intermediate 24a; 134 mg, 57%) as a yellow solid. LCMS (Method 1): Rt 1.81, m/z 369 [MH$^+$]. Second eluting: 5-tert-butyl-2-[2-(2-morpholin-4-yl-ethyl)-2H-indazol-6-yl]-2H-pyrazol-3-ylamine (Intermediate 24b; 86 mg, 30%) as a yellow solid. LCMS (Method 1): Rt 1.68, m/z 369 [MH$^+$]. Regioisomer structure confirmation using $^1$H NMR nOe.

b. {5-tert-Butyl-2-[1-(2-morpholin-4-yl-ethyl)-1H-indazol-6-yl]-2H-pyrazol-3-yl}-carbamic acid 2,2,2-trichloro-ethyl ester (Intermediate 24c)

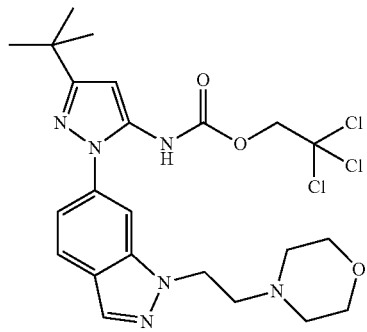 [SMILES: CC(C)(C)c1cc(NC(=O)OCC(Cl)(Cl)Cl)n(-c2ccc3cnn(CCN4CCOCC4)c3c2)n1]

A solution of Intermediate 24a (134 mg, 0.36 mmol) was formed in THF (10 mL). DIPEA (125 µL, 0.72 mmol) was added followed by the dropwise addition of a solution of 2,2,2-trichloroethylchloroformate (50 µL, 0.36 mmol) in THF (2 mL). The mixture was stirred at RT for 4 h, then partitioned between EtOAc/water and extracted with EtOAc. The combined organics were dried over Na$_2$SO$_4$, filtered and concentrated in vacuo. Purification by FCC, using 0-10% MeOH in EtOAc, gave the title compound (200 mg, 99%) as a colourless film. LCMS (Method 4): Rt 2.59, m/z 543, 545 [MH$^+$].

c. 1-{5-tert-Butyl-2-[1-(2-morpholin-4-yl-ethyl)-1H-indazol-6-yl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea (Example 24)

The title compound was prepared as an off-white solid (65 mg, 50%) using Intermediate 1g (71 mg, 0.22 mmol) and Intermediate 24c (100 mg, 0.18 mmol) in a similar manner to Example 1. LCMS (Method 5): Rt 3.40 min, m/z 717 [MH$^+$]. $^1$H NMR (400 MHz, d$_6$-DMSO): 1.30 (9H, s), 1.37 (3H, d, J 6.9), 1.38 (3H, d, J 6.9), 1.80-1.97 (2H, m), 2.05-2.10 (2H, m), 2.41 (4H, br s), 2.75 (2H, br s), 3.49 (4H, br s), 3.56 (1H, sept, J 6.9), 4.52 (2H, m), 4.79-4.85 (1H, m), 5.52 (1H, t, J 4.5), 6.40 (1H, s), 7.06 (1H, d, J 8.5), 7.13 (1H, dd, J 9.7, 2.0), 7.22-7.29 (4H, m), 7.36-7.39 (1H, m), 7.68 (1H, d, J 9.7), 7.83 (1H, s), 7.87 (1H, d, J 8.5), 8.13-8.19 (3H, m).

Example 25

1-{5-tert-Butyl-2-[2-(2-morpholin-4-yl-ethyl)-2H-indazol-6-yl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea

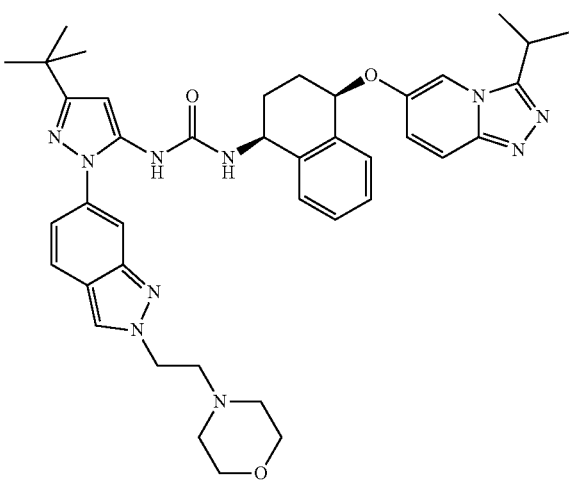 [SMILES: CC(C)c1nnc2ccc(O[C@@H]3CC[C@H](NC(=O)Nc4cc(C(C)(C)C)nn4-c4ccc5cn(CCN6CCOCC6)nc5c4)c4ccccc43)cn12]

a. {5-tert-Butyl-2-[2-(2-morpholin-4-yl-ethyl)-2H-indazol-6-yl]-2H-pyrazol-3-yl}-carbamic acid 2,2,2-trichloro-ethyl ester (Intermediate 25a)

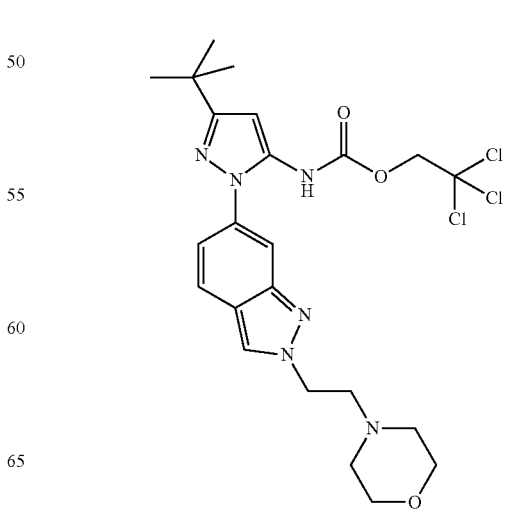

To a solution of Intermediate 24b (86 mg, 0.23 mmol) in THF (10 mL) was added DIPEA (80 μL, 0.46 mmol), followed by the dropwise addition of a solution of 2,2,2-trichloroethylchloroformate (32 μL, 0.23 mmol) in THF (2 mL). The mixture was stirred at RT for 4 h, then partitioned between EtOAc/water and extracted with EtOAc. The combined organics were dried over $Na_2SO_4$, filtered and concentrated in vacuo. Purification by FCC, using 0-20% MeOH in EtOAc, gave the title compound (32 mg, 26%) as a yellow solid. LCMS (Method 4): Rt 2.64, 0.2 m/z 543, 545 [MH$^+$].

b. 1-{5-tert-Butyl-2-[2-(2-morpholin-4-yl-ethyl)-2H-indazol-6-yl]-2H-pyrazol-3-yl}-3-[(1S,4R)-4-(3-isopropyl-[1,2,4]triazolo[4,3-a]pyridin-6-yloxy)-1,2,3,4-tetrahydro-naphthalen-1-yl]-urea (Example 25)

The title compound was prepared as an off-white solid (16 mg, 47%) using Intermediate 1g (23 mg, 0.07 mmol) and Intermediate 25a (32 mg, 0.06 mmol) in a similar manner to example 1. LCMS (Method 5): Rt 3.43 min, m/z 717 [MH$^+$]. $^1$H NMR (400 MHz, d$_6$-DMSO): 1.29 (9H, s), 1.37 (3H, d, J 6.1), 1.38 (3H, d, J 6.1), 1.81-1.97 (2H, m), 2.03-2.13 (2H, m), 2.42 (4H, t, J 4.3), 2.85 (2H, t, J 6.3), 3.50-3.60 (5H, m), 4.56 (2H, t, J 6.3), 4.80-4.86 (1H, m), 5.52 (1H, t, J 4.3), 6.36 (1H, s), 7.11 (1H, d, J 8.5), 7.14-7.19 (2H, m), 7.25-7.30 (3H, m), 7.36-7.39 (1H, m), 7.65 (1H, m), 7.68 (1H, d, J 9.8), 7.83 (1H, d, J 9.0), 8.16 (1H, s), 8.20 (1H, m), 8.48 (1H, s).

Example 26

1-[5-tert-Butyl-2-(2-hydroxy-ethyl)-2H-pyrazol-3-yl]-3-{(1S,4R)-4-[3-(2,6-dichloro-phenyl)-[1,2,4]triazolo[4,3-a]pyridin-6-yloxy]-1-1,2,3,4-tetrahydro-naphthalen-1-yl}-urea

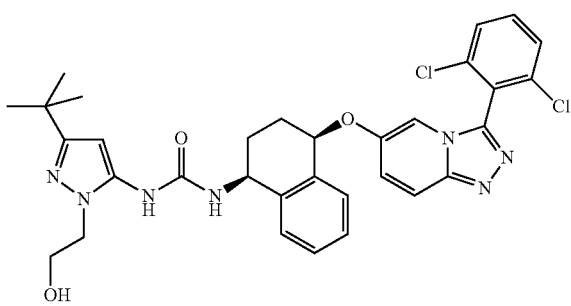 [SMILES: CC(C)(C)c1cc(NC(=O)N[C@H]2CC[C@@H](Oc3ccc4nnc(-c5c(Cl)cccc5Cl)n4c3)c3ccccc32)n(CCO)n1]

a. [5-tert-Butyl-2-(2-hydroxy-ethyl)-2H-pyrazol-3-yl]-carbamic acid 2,2,2-trichloro-ethyl ester (Intermediate 26a)

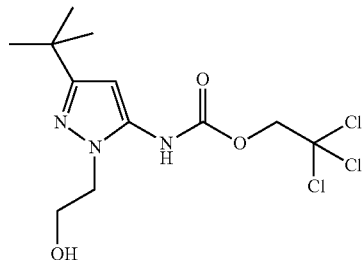 [SMILES: CC(C)(C)c1cc(NC(=O)OCC(Cl)(Cl)Cl)n(CCO)n1]

To a mixture of Intermediate 10a (367 mg, 2.0 mmol) in water (1 mL) and EtOAc (4 mL), was added NaOH (107 mg, 2.67 mmol) followed by 2,2,2-trichloro chloroformate (385 μL, 2.80 mmol). The reaction mixture was stirred at RT for 2 h and then diluted with additional EtOAc. The organic layer was washed with water followed by brine, dried and concentrated in vacuo. The resultant residue was purified by FCC, using 0-80% EtOAc in DCM to afford the title compound (466 mg, 65%) as a colourless oil which solidified on standing. LCMS (Method 3): Rt 3.73 min, m/z 358, 360 [MH$^+$].

b. 2,6-Dichloro-benzoic acid N'-(5-fluoro-pyridin-2-yl)-hydrazide (Intermediate 26b)

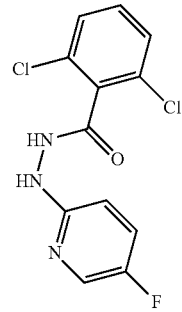 [SMILES: O=C(NNc1ccc(F)cn1)c1c(Cl)cccc1Cl]

DIPEA (2.73 mL, 15.7 mmol) was added dropwise to a solution of (5-fluoro-pyridin-2-yl)-hydrazine (for reference procedure see WO 2010/022076, which is incorporated herein by reference in its entirety; 1.0 g, 7.87 mmol) and 2,6-dichloro-benzoyl (1.65 g, 7.87 mmol) in DCM (50 mL). The reaction mixture was stirred at RT for 30 min and then suspended in DCM and water. The resulting suspension was filtered and the solid was collected by filtration, washed with c. 3-(2,6-Dichloro-phenyl)-6-fluoro-[1,2,4]triazolo[4,3-a]pyridine (Intermediate 26c)

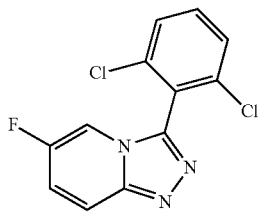 [SMILES: Fc1ccc2nnc(-c3c(Cl)cccc3Cl)n2c1]

Hexachloroethane (2.60 g, 11.0 mmol) was added portionwise over 5 min at RT to a stirred mixture of Intermediate 26b (1.65 g, 5.50 mmol), triphenylphosphine (2.88 g, 11.0 mmol), and triethylamine (3.06 mL, 22.0 mmol) in THF (50 mL). The reaction mixture was stirred at RT for 18 h and then allowed to stand at RT for 72 h. The resulting suspension was filtered and the filtrate was concentrated in vacuo and purified by FCC using SCX-2 cartridge. The cartridge was washed with MeOH, and the product was eluted with 2M $NH_3$ in MeOH to give the title compound (1.44 g, 93%) as a beige solid. LCMS (Method 3): Rt 3.08 min, m/z 282, 284 [MH+].

d. (1S,4R)-4-[3-(2,6-Dichloro-phenyl)-[1,2,4]triazolo[4,3-a]pyridin-6-yloxy]-1,2,3,4-tetrahydro-naphthalen-1-ylamine (Intermediate 26d)

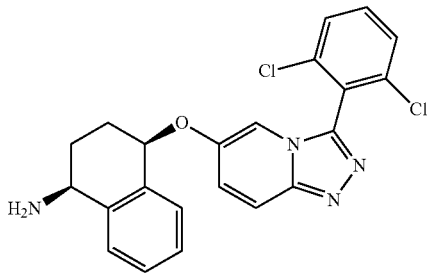 [SMILES: N[C@H]1CC[C@@H](Oc2ccc3nnc(-c4c(Cl)cccc4Cl)n3c2)c2ccccc21]

Intermediate 1d (404 mg, 2.48 mmol) was added to a stirred solution of sodium hydride (60% in mineral oil, 298 mg, 7.44 mmol) in anhydrous DMF (15 mL) at RT under an argon atmosphere. The reaction mixture was stirred at RT for 15 min, then Intermediate 26c (0.70 g, 2.48 mmol) was added, and stirring at 60° C. was continued for 1 h. After cooling, the reaction mixture was quenched by careful addition of a saturated aqueous solution of $NH_4Cl$ and water (1:1) and extracted with EtOAc (×3). The combined organic layers were washed with a saturated aqueous solution of $NaHCO_3$ followed by brine, dried and concentrated in vacuo. The resultant residue was purified by FCC, using 0-20% [2M $NH_3$ in MeOH] in DCM to afford the title compound (345 mg, 33%) as a brown residue. LCMS (Method 3): Rt 2.34 min, m/z 425, 427. [MH+].

e. 1-[5-tert-Butyl-2-(2-hydroxy-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea (Example 26)

A mixture of Intermediate 26a (100 mg, 0.279 mmol), Intermediate 26d (108 mg, 0.254 mmol), and DIPEA (73 µL, 0.419 mmol) in dioxane (2.5 mL) was stirred at 60° C. for 42 h and then left standing at RT for 72 h. The volatiles were concentrated in vacuo and the resultant residue was purified by FCC, using 0-10% MeOH in DCM followed by MDAP (Method 7) to afford the title compound (23 mg, 14%) as a white solid. LCMS (Method 5): Rt 4.19 min, m/z 634 [MH+]. $^1$H NMR (400 MHz, DMSO): 1.21 (9H, s), 1.79-2.16 (4H, m), 3.62-3.70 (2H, m), 3.94 (2H, t, J=6.0 Hz), 4.78-4.88 (1H, m), 4.99 (1H, br s), 5.55 (1H, t, J=4.2 Hz), 6.05 (1H, s), 7.07 (1H, d, J=8.6 Hz), 7.23-7.30 (1H, m), 7.31-7.38 (4H, m), 7.70-7.74 (1H, m), 7.74-7.80 (2H, m), 7.91 (1H, d, J=9.9 Hz), 7.98 (1H, d, J=2.1 Hz), 8.19 (1H, s).

Example 27

1-[5-tert-Butyl-2-(2-morpholin-4-yl-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea Formate Salt

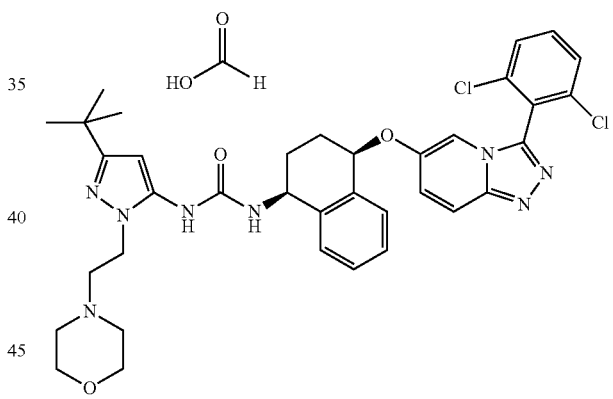

To a stirred solution of Example 26 (38 mg, 0.06 mmol) and methanesulfonyl chloride (7.0 µL, 0.09 mmol) in DCM (1 mL), was added DIPEA (31 µL, 0.18 mmol). The reaction mixture was stirred at RT 1 h, then diluted with DCM, washed with water followed by a saturated aqueous solution of $NaHCO_3$ and brine, dried and concentrated in vacuo. The resultant residue was dissolved in THF (2 mL) and treated with morpholine (26 µL, 0.30 mmol). The reaction mixture was heated at 60° C. for 18 h, then the volatiles were concentrated in vacuo. The resultant residue was partitioned between DCM and water. The organic layer was washed with brine, dried and concentrated in vacuo. The resultant residue was purified by MDAP (Method 7) to afford the title compound (13 mg, 30%) as an off white solid. LCMS (Method 5): Rt 3.56 min, m/z 703 [MH+]. $^1$H NMR (400 MHz, DMSO): 1.20 (9H, s), 2.15-1.82 (4H, m), 2.41-2.35 (4H, m), 2.61 (2H, t, J=7.1 Hz), 3.53 (4H, t, J=4.6 Hz), 3.98 (2H, t, J=7.1 Hz), 4.79-4.88 (1H, m), 5.55 (1H, t, J=4.2 Hz), 6.02 (1H, s), 6.95

(1H, d, J=8.6 Hz), 7.24-7.30 (1H, m), 7.31-7.39 (4H, m), 768-7.80 (3H, m), 7.91 (1H, d, J=9.9 Hz), 7.98 (1H, d, J=2.1 Hz), 8.24 (2H, s).

Example 28

1-[5-tert-Butyl-2-(2-dimethylamino-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea Formate Salt

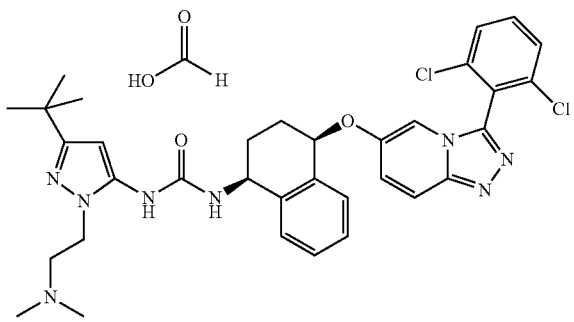 [SMILES: CN(C)CCn1nc(C(C)(C)C)cc1NC(=O)N[C@H]1CC[C@@H](Oc2ccc3nnc(-c4c(Cl)cccc4Cl)n3c2)c2ccccc21 ; O=CO]

a. Methanesulfonic acid 2-[3-tert-butyl-5-(3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-ureido)-pyrazol-1-yl]-ethyl ester (Intermediate 28a)

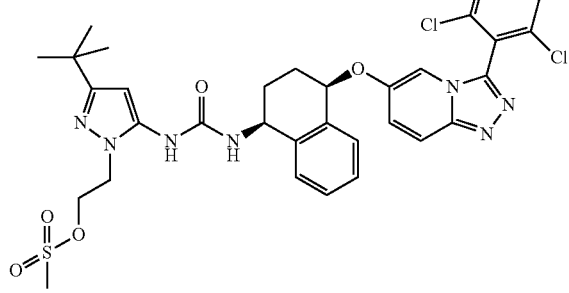

A mixture of Example 26 (350 mg, 0.55 mmol), methanesulfonyl chloride (55 µL, 0.72 mmol), and DIPEA (288 µL, 1.65 mmol) in DCM (4 mL) was stirred at RT for 45 min. Additional amount of methanesulfonyl chloride (15 µL) was added, and stirring was continued for 30 min. Additional amount of methanesulfonyl chloride (15 µL) was added and stirring was continued for 20 min. The reaction mixture was partitioned between DCM and water. The organic layer was washed with brine, dried through a phase separator and concentrated in vacuo to afford the title compound (0.33 g, 84%) as a pale yellow solid. LCMS (Method 3): Rt 3.77 min, m/z 712, 714. [MH$^+$].

b. 1-[5-tert-Butyl-2-(2-dimethylamino-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea (Example 28)

A mixture of Intermediate 28a (110 mg, 0.15 mmol) and dimethylamine (2.0M in THF, 1.54 mL, 3.09 mmol) in anhydrous THF (2 mL) was stirred at 60° C. for 18 h in a sealed vial. The volatiles were concentrated in vacuo and the resultant residue was purified by MDAP (Method 7) to afford the title compound (44 mg, 43%). LCMS (Method 5): Rt 3.50 min, m/z 661 [MH$^+$]. $^1$H NMR (400 MHz, DMSO): 1.19 (9H, s), 1.83-2.14 (4H, m), 2.18 (6H, s), 2.59 (2H, t, J=6.9 Hz), 3.96 (2H, t, J=6.9 Hz), 4.79-4.87 (1H, m), 5.53 (1H, t, J=4.0 Hz), 6.01 (1H, s), 6.92 (1H, d, J=8.7 Hz), 7.22-7.28 (1H, m), 7.30-7.38 (4H, m), 7.68-7.78 (3H, m), 7.90 (1H, dd, J=9.9, 0.8 Hz), 7.96 (1H, d, J=2.0 Hz), 8.15 (1H, s), 8.44 (1H, s).

Example 29

1-[5-tert-Butyl-2-(2-piperidin-1-yl-ethyl)-2H-pyrazol-3-yl]-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea Formate Salt

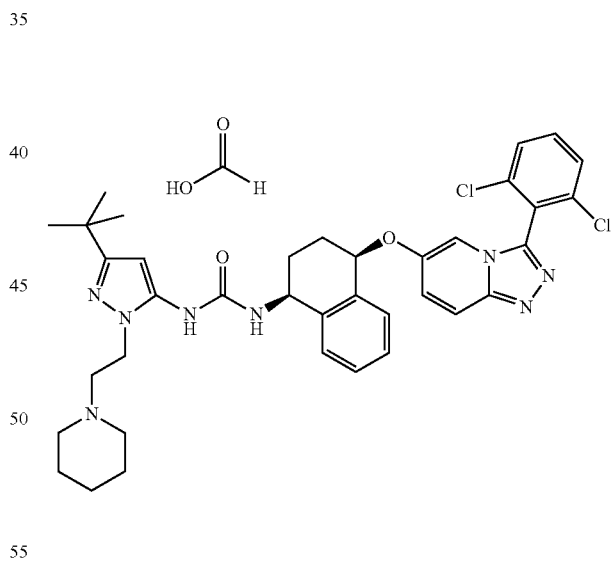

The title compound was prepared starting from Intermediate 28a and piperidine using analogous procedures to those described in Example 28. LCMS (Method 5): Rt 3.73 min, m/z 701 [MH$^+$]. $^1$H NMR (400 MHz, DMSO): 1.20 (9H, s), 1.30-1.39 (2H, m), 1.51-1.41 (4H, m), 1.81-2.16 (4H, m), 2.34-2.43 (4H, m), 2.60 (2H, t, J=7.1 Hz), 3.97 (2H, t, J=7.1 Hz), 4.79-4.88 (1H, m), 5.55 (1H, t, J=4.2 Hz), 6.02 (1H, s), 6.92 (1H, d, J=8.6 Hz), 7.20-7.31 (1H, m), 7.31-7.39 (4H, m), 7.69-7.79 (3H, m), 7.91 (1H, dd, J=9.9, 0.8 Hz), 7.97 (1H, d, J=2.0 Hz), 8.16 (1.5H, s), 8.28 (1H, s).

Example 30

1-{5-tert-Butyl-2-[2-(4-methyl-piperazin-1-yl)-ethyl]-2H-pyrazol-3-yl}-3-{(1S,4R)-4-[3-(2,6-dichloro-phenyl)-[1,2,4]triazolo[4,3-a]pyridin-6-yloxy]-1,2,3,4-tetrahydro-naphthalen-1-yl}-urea Formate Salt

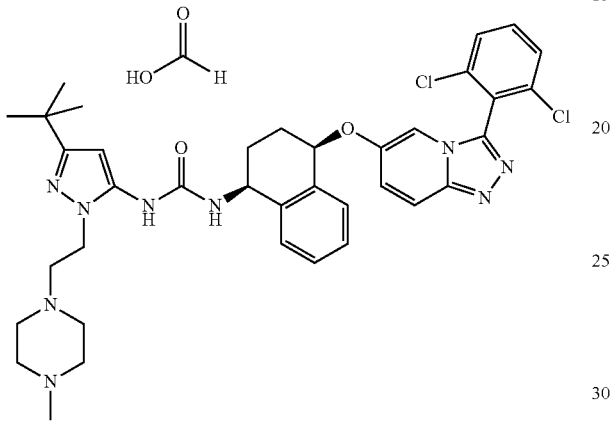

The title compound was prepared starting from Intermediate 28a and 1-methyl-piperazine using analogous procedures to those described in Example 28. LCMS (Method 5): Rt 3.41 min, m/z 716.5 [MH⁺]. ¹H NMR (400 MHz, DMSO): 1.20 (9H, s), 1.82-2.12 (4H, m), 2.14 (3H, s), 2.25-2.45 (8H, m), 2.60 (2H, t, J=7.15 Hz), 3.96 (2H, t, J=7.1 Hz), 4.79-4.88 (1H, m), 5.55 (1H, t, J=4.2 Hz), 6.02 (1H, s), 6.90 (1H, d, J=8.6 Hz), 7.24-7.30 (1H, m), 7.31-7.40 (4H, m), 7.68-7.79 (3H, m), 7.91 (1H, d, J=9.9 Hz), 7.98 (1H, d, J=2.0 Hz), 8.16 (1.5H, s), 8.22 (1H, s).

Example 31

1-[5-tert-Butyl-2-(2-hydroxy-ethyl)-2H-pyrazol-3-yl]-3-{(1S,4R)-4-[3-(2-chloro-phenyl)-[1,2,4]triazolo[4,3-a]pyridin-6-yloxy]-1,2,3,4-tetrahydro-naphthalen-1-yl}-urea

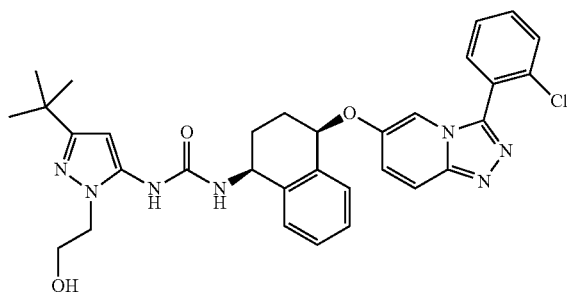 [SMILES: CC(C)(C)c1cc(NC(=O)N[C@H]2CC[C@@H](Oc3ccc4nnc(-c5ccccc5Cl)n4c3)c3ccccc32)n(CCO)n1]

a. 2-Chloro-benzoic acid N'-(5-fluoro-pyridin-2-yl)-hydrazide (Intermediate 31a)

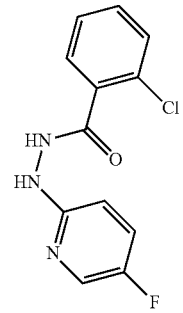 [SMILES: O=C(NNc1ccc(F)cn1)c1ccccc1Cl]

To a solution of (5-fluoro-pyridin-2-yl)-hydrazine (for reference procedure see WO 2010/022076, which is incorporated herein by reference; 1.0 g, 7.87 mmol) and 2-chloro-benzoyl chloride (1 mL, 7.87 mmol) in DCM (50 mL) was added dropwise DIPEA (2.74 mL, 15.75 mmol). The reaction mixture was stirred at RT for 1 h then washed with water. The organic layer was dried through a phase separator and then concentrated in vacuo to afford the title compound (1.95 g, 93%) as a brown solid. LCMS (Method 3): Rt 2.82 min, m/z 266 [MH⁺].

b. 3-(2-Chloro-phenyl)-6-fluoro-[1,2,4]triazolo[4,3-a]pyridine (Intermediate 31b)

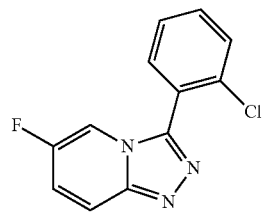 [SMILES: Fc1ccc2nnc(-c3ccccc3Cl)n2c1]

Hexachloroethane (3.47 g, 14.68 mmol) was added portionwise at RT to a stirred mixture of Intermediate 31a (1.95 g, 7.34 mmol), triphenylphosphine (3.85 g, 14.68 mmol), and triethylamine (4.12 mL, 29.36 mmol) in anhydrous THF (60 mL). The reaction mixture was stirred at RT for 3.5 h. The resulting suspension was filtered, washing the solid with Et₂O. The filtrate was concentrated in vacuo and the resultant residue purified by FCC using SCX-2 cartridge. The cartridge was washed with MeOH and the product was eluted with 2M NH₃ in MeOH to give the title compound (1.81 g, quantitative) as a fawn coloured solid. LCMS (Method 3): Rt 2.96 min, m/z 248 [MH⁺].

c. (1S,4R)-4-[3-(2-Chloro-phenyl)-[1,2,4]triazolo[4,3-a]pyridin-6-yloxy]-1,2,3,4-tetrahydro-naphthalen-1-ylamine (Intermediate 31c)

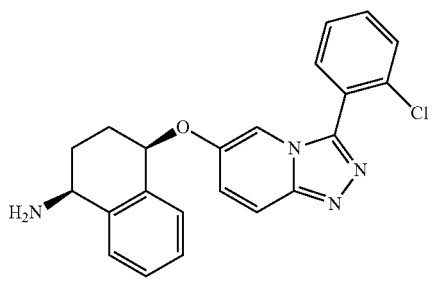 [SMILES: N[C@H]1CC[C@@H](Oc2ccc3nnc(-c4ccccc4Cl)n3c2)c2ccccc21]

Sodium hydride (60% in mineral oil, 840 mg, 21.9 mmol) was added portionwise to a stirred solution of Intermediate 1d (1.19 g, 7.31 mmol) in anhydrous DMF (30 mL) at RT under an argon atmosphere. Intermediate 31b (1.81 g, 7.31 mmol) was then added, and stirring at 60° C. was continued for 1.5 h. After cooling, the reaction mixture was quenched by careful addition of a saturated aqueous solution of NH₄Cl and extracted with EtOAc (×2). The combined organic layers were washed with brine, dried (MgSO₄) and concentrated in vacuo. The resultant residue was purified by FCC, using 0-10% MeOH in DCM to afford the title compound (1.48 g, 52%) as a brown foam. LCMS (Method 3): Rt 0.42 and 2.33 min, m/z 391. [MH⁺].

d. 1-[5-tert-Butyl-2-(2-hydroxy-ethyl)-2H-pyrazol-3-yl]-3-{(1S,4R)-4-[3-(2-chloro-phenyl)-[1,2,4]triazolo[4,3-a]pyridin-6-yloxy]-1,2,3,4-tetrahydro-naphthalen-1-yl}-urea (Example 31)

A mixture of Intermediate 26a (340 mg, 0.95 mmol), Intermediate 31c (372 mg, 0.95 mmol), and DIPEA (248 μL, 1.43 mmol) in dioxane (5 mL) was stirred at 70° C. for 18 h. After cooling to RT, the reaction mixture was partitioned between DCM and water. The organic layer was dried through a phase separator and then concentrated in vacuo. The resultant residue was purified by FCC, using 0-10% MeOH in DCM to afford the title compound (536 mg, 94%) as a brown solid. An aliquot of the compound thus obtained (100 mg) was further purified by MDAP (Method 7) to afford the title compound (45 mg). LCMS (Method 5): Rt 4.08 min, m/z 600 [MH⁺]. ¹H NMR (400 MHz, DMSO): 1.20 (9H, s), 1.81-2.19 (4H, m), 3.66 (2H, d, J=6.1 Hz), 3.93 (2H, t, J=6.0 Hz), 4.78-4.84 (1H, m), 4.98 (1H, br s), 5.51 (1H, t, J=4.3 Hz), 6.05 (1H, s), 7.06 (1H, d, J=8.6 Hz), 7.23-7.30 (1H, m), 7.32-7.38 (4H, m), 7.60 (1H, td, J=7.5, 1.3 Hz), 7.68 (1H, td, J=7.7, 1.9 Hz), 7.73 (2H, td, J=7.5, 1.3 Hz), 7.82-7.92 (2H, m), 8.17 (1H, s).

Example 32

1-[5-tert-Butyl-2-(2-morpholin-4-yl-ethyl)-2H-pyrazol-3-yl]-3-{(1S,4R)-4-[3-(2-chloro-phenyl)-[1,2,4]triazolo[4,3-a]pyridin-6-yloxy]-1,2,3,4-tetrahydro-naphthalen-1-yl}-urea Formate Salt

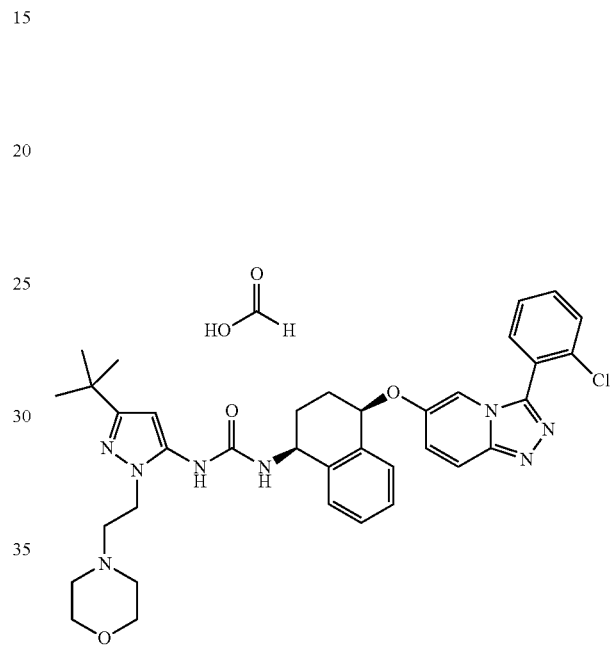

A mixture of Example 31 (100 mg, 0.17 mmol), methanesulfonyl chloride (38 μL, 0.33 mmol), and DIPEA (87 μL, 0.50 mmol) in DCM (1 mL) was stirred at RT 45 min. Additional amount of methanesulfonyl chloride (20 μL) was added, and stirring at RT was continued for 20 min. The reaction mixture was diluted with DCM, washed with water (×2) followed by brine, dried through a phase separator and concentrated in vacuo. The resultant residue was dissolved in THF (1 mL) and treated with morpholine (73 μL, 0.83 mmol). Additional amount of morpholine (73 μL, 0.83 mmol) and THF (1 mL) was added, and the reaction mixture was heated at 60° C. for 18 h. After cooling, the volatiles were concentrated in vacuo and the resultant residue was purified by MDAP (Method 7) to afford the title compound (46 mg, 41%) as an off white solid. LCMS (Method 5): Rt 3.50 min, m/z 669 [MH⁺]. ¹H NMR (400 MHz, DMSO): 1.20 (9H, s), 1.83-2.19 (4H, m), 2.35-2.41 (4H, m), 2.61 (2H, t, J=7.1 Hz), 3.54 (4H, t, J=4.6 Hz), 3.99 (2H, t, J=7.1 Hz), 4.79-4.88 (1H, m), 5.52 (1H, t, J=4.2 Hz), 6.03 (1H, s), 6.94 (1H, d, J=8.6 Hz), 7.24-7.31 (1H, m), 7.32-7.39 (4H, m), 7.69 (1H, td, J=7.7, 1.8

Hz), 7.68 (1H, td, J=7.7, 1.8 Hz), 7.72-7.78 (2H, m), 7.84-7.92 (2H, m), 8.18 (1H, s), 8.22 (1H, s).

Example 33

1-(5-tert-Butyl-2-methyl-2H-pyrazol-3-yl)-3-{(1S,4R)-4-[3-(2,6-dichlorophenyl)-[1,2,4]triazolo[4,3-a]pyridin-6-yloxy]-1,2,3,4-tetrahydronaphthalen-1-yl]-urea

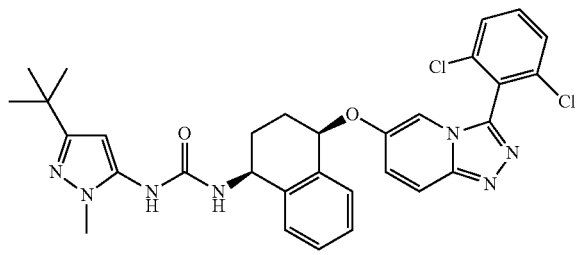 [SMILES: Cn1nc(C(C)(C)C)cc1NC(=O)N[C@H]1CC[C@@H](Oc2ccc3nnc(-c4c(Cl)cccc4Cl)n3c2)c2ccccc21]

a. (5-tert-Butyl-2-methyl-2H-pyrazol-3-yl)-carbamic acid 2,2,2-trichloro-ethyl ester (Intermediate 33a)

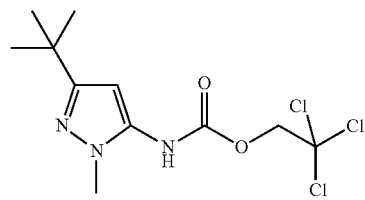 [SMILES: Cn1nc(C(C)(C)C)cc1NC(=O)OCC(Cl)(Cl)Cl]

A solution of 5-tert-butyl-2-methyl-2H-pyrazol-3-ylamine (0.5 g, 3.26 mmol) in EtOAc (10 mL) was treated with aqueous NaOH (1M, 5.87 mmol), followed by 2,2,2-trichloroethyl chloroformate (0.54 mL, 3.92 mmol), and the reaction mixture was stirred at RT for 1 h. The mixture was partitioned between EtOAc (10 mL) and water (2×10 mL). The organic layer was dried (MgSO$_4$), filtered and concentrated in vacuo. The residue was purified by FCC, using 0-100% EtOAc in cyclohexane to afford the title compound as a pale orange gum (0.915 g, 86%). LCMS (Method 3): Rt 3.88 min, m/z 328/330 [MH$^+$].

b. 1-(5-tert-Butyl-2-methyl-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl]-urea (Example 33)

A solution of intermediate 33a (70 mg, 0.21 mmol), intermediate 26d (90 mg, 0.21 mmol), and DIPEA (55 µL, 0.32 mmol) in dioxane (1 mL) was heated at 70° C. for 18 h. The mixture was concentrated in vacuo and the residue was purified by MDAP (Method 7) to afford the title compound as a glassy solid (38 mg, 29%). LCMS (Method 5): Rt 4.37 min, m/z 604.2 [MH$^+$]. $^1$H NMR (400 MHz, d$_6$-DMSO): 1.20 (9H, s), 1.83-2.15 (4H, m), 3.56 (3H, s), 4.79-4.88 (1H, m), 5.55 (1H, t, J=4.6 Hz), 6.01 (1H, s), 6.86 (1H, d, J=8.5 Hz), 7.23-7.29 (1H, m), 7.31-7.37 (4H, m), 7.69-7.79 (3H, m), 7.91 (1H, dd, J 9.7, 0.9 Hz), 7.98 (1H, d, J=2.2 Hz), 8.23 (1H, s).

Example 34

1-[5-tert-Butyl-2-(2-morpholin-4-yl-ethyl)-2H-pyrazol-3-yl]-3-[(1S,4R)-4-(3-cyclohexyl-[1,2,4]triazolo[4,3-a]pyridin-6-yloxy)-1,2,3,4-tetrahydro-naphthalen-1-yl]-urea Partial Formate Salt

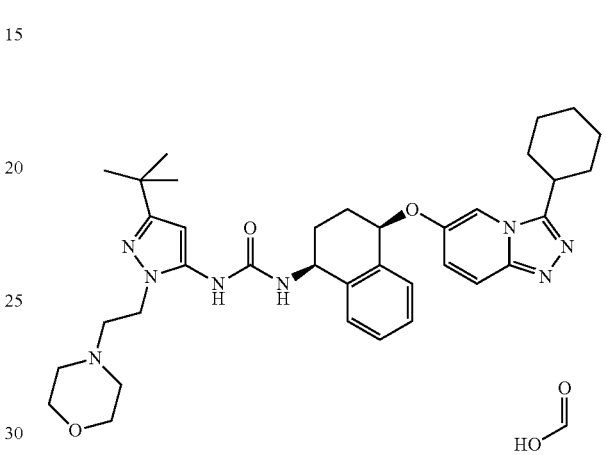

a. Cyclohexanecarboxylic acid N'-(5-fluoro-pyridin-2-yl)-hydrazide (Intermediate 34a)

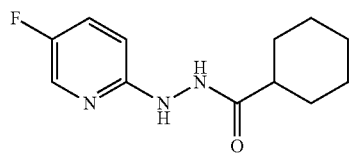 [SMILES: O=C(NNc1ccc(F)cn1)C1CCCCC1]

To a solution of 5-fluoro-2-hydrazinyl-pyridine (for reference procedure see WO 2010 022076, which is incorporated herein by reference in its entirety; 1.00 g, 7.87 mmol), cyclohexane carboxylic acid (1.21 g, 9.44 mmol), and HOBt.H$_2$O (166 mg, 0.787 mmol) at 0° C. under N$_2$ was added EDC (1.81 g, 9.44 mmol), then the mixture stirred at 0° C. for 15 min, and at RT for 17 h. Water was added, then the organics isolated, cooled to 0° C., then the resulting suspension filtered to leave the title compound as a white solid (1.16 g, 62%). $^1$H NMR (400 MHz, CDCl$_3$): 1.21-1.38 (3H, m), 1.45-1.55 (2H, m), 1.66-1.73 (1H, m), 1.80-1.96 (4H, m), 2.22 (1H, tt, J 11.6, 3.5

Hz), 6.62-6.66 (2H, m), 7.29 (1H, ddd, J 9.2, 7.9, 3.1 Hz), 7.55 (1H, d, J=4.2 Hz), 8.03 (1H, d, J=2.9 Hz).

b. 3-Cyclohexyl-6-fluoro-[1,2,4]triazolo[4,3-a]pyridine (Intermediate 34b)

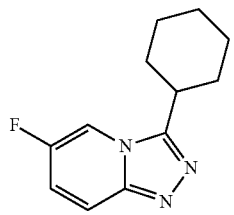 [SMILES: Fc1ccc2nnc(C3CCCCC3)n2c1]

To a solution of Intermediate 34a (1.15 g, 4.83 mmol), triphenylphosphine (2.54 g, 9.67 mmol), and triethylamine (2.68 mL, 19.3 mmol) in dry THF (17 mL) at 0° C. under $N_2$ was added hexachloroethane (2.28 g, 9.67 mmol), and the mixture stirred at 0° C. for 15 min, and at RT for 6 h. Water was added, then the organics washed with brine, dried ($MgSO_4$) and concentrated in vacuo. Flash chromatography (silica gel, 0-100% EtOAc in cyclohexane) gave the title compound as an off-white solid (330 mg, 31%). $^1$H NMR (400 MHz, $CDCl_3$): 1.36-1.55 (3H, m), 1.78-2.00 (5H, m), 2.05-2.14 (2H, m), 2.97 (1H, tt, J=11.5, 3.5 Hz), 7.16 (1H, ddd, J=10.0, 7.5, 2.3 Hz), 7.76 (1H, dd, J=10.0, 4.9, 0.9 Hz), 7.85 (1H, ddd, J=3.5, 2.2, 0.9 Hz).

c. (1S,4R)-4-(3-Cyclohexyl-[1,2,4]triazolo[4,3-a]pyridin-6-yloxy)-1,2,3,4-tetrahydro-naphthalen-1-ylamine (Intermediate 34c)

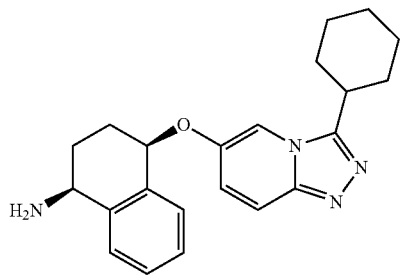 [SMILES: N[C@H]1CC[C@@H](Oc2ccc3nnc(C4CCCCC4)n3c2)c2ccccc21]

An opaque brown solution of Intermediate 1d (171 mg, 1.05 mmol) and sodium hydride (60% dispersion in oil, 120 mg, 3.00 mmol) in dry DMF (2 mL) was stirred at RT under Argon for 30 min. Intermediate 34b (219 mg, 1.00 mmol) was added, and the resulting dark solution stirred at 60° C. for 2 h. The cooled solution was concentrated in vacuo, redissolved in MeOH (2 mL), applied to an SCX-2 cartridge, and washed with MeOH. The product was eluted with 2M $NH_3$ in MeOH; concentration in vacuo left a brown oil. Flash chromatography (silica 25 g, 2-10% [2M $NH_3$ in MeOH] in DCM) gave a yellow oil. Freeze-drying from MeCN-water (1:2, 3 mL) left the title compound as a pale yellow solid (203 mg, 56%). LCMS (Method 3): Rt 2.29 min, m/z 363 [MH$^+$].

d. 1-[5-tert-Butyl-2-(2-hydroxy-ethyl)-2H-pyrazol-3-yl]-3-[(1S,4R)-4-(3-cyclohexyl-[1,2,4]triazolo[4,3-a]pyridin-6-yloxy)-1,2,3,4-tetrahydro-naphthalen-1-yl]-urea (Intermediate 34d)

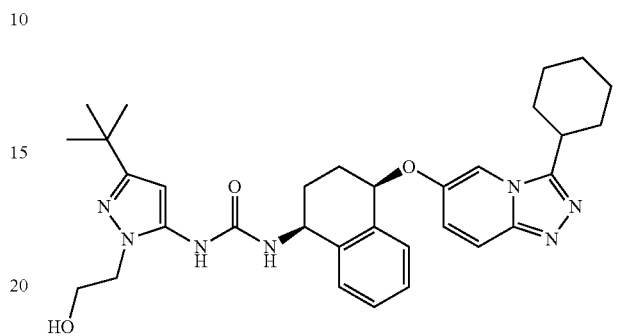

A brown solution of Intermediate 26a (94.2 mg, 0.263 mmol), Intermediate 34c (90.6 mg, 0.250 mmol), and DIPEA (0.054 mL, 0.31 mmol) in dry dioxane (3 mL) was stirred at 75° C. for 16 h. The cooled solution was concentrated in vacuo, suspended in water (3 mL) and extracted with DCM (2×3 mL). The combined organics were passed through a hydrophobic frit and concentrated in vacuo to leave a dark brown oil. Flash chromatography (silica gel, 3-9% MeOH in DCM) gave a pale yellow solid. MDAP (Method 7) gave an off-white solid (72 mg, 50%). LCMS (Method 5): Rt 3.98 min, m/z 572.4 [MH$^+$].

e. 1-[5-tert-Butyl-2-(2-morpholin-4-yl-ethyl)-2H-pyrazol-3-yl]-3-[(1S,4R)-4-(3-cyclohexyl-[1,2,4]triazolo[4,3-a]pyridin-6-yloxy)-1,2,3,4-tetrahydro-naphthalen-1-yl]-urea Partial Formate Salt (Example 34)

A solution of Intermediate 34d (71 mg, 0.12 mmol), mesyl chloride (29 mg, 0.25 mmol), and DIPEA (0.065 mL, 0.37 mmol) in DCM (2 mL) was stirred at 0° C. for 30 min. Water (2 mL) and sat. aq. $NaHCO_3$ solution (2 mL) were added. The aqueous was extracted with DCM (2 mL), then the combined organics passed through a hydrophobic frit and concentrated under vacuum to leave a pale yellow gum. The gum was dissolved in DMF (1 mL), and morpholine (0.054 mL, 0.62 mmol) was added, and then stirred at 75° C. for 16 h. The cooled solution was concentrated in vacuo, redissolved in MeOH (1 mL), applied to an SCX-2 cartridge (5 g) and washed with MeOH. The product was eluted with 2M $NH_3$ in MeOH; concentration in vacuo left a yellow gum. Prep HPLC (Gemini C18, 10-60% MeCN in water, 0.1% $HCO_2H$, 20 min) and freeze-drying of the desired fractions gave a white solid (14.9 mg, 19%). LCMS (Method 5): Rt 3.46 min, m/z 641.4 [MH$^+$]. $^1$H NMR (400 MHz, $d_6$-DMSO: 1.20 (9H, s), 1.27-1.38 (1H, m), 1.44-1.55 (2H, m), 1.58-1.77 (3H, m), 1.80-1.86 (2H, m), 1.92-2.21 (6H, m), 2.39 (4H, t, J=4.4 Hz), 2.62 (2H, t, J=7.1 Hz), 3.29 (1H, tt, J=11.3, 3.7 Hz), 3.54 (4H, t, J=4.5 Hz), 4.00 (2H, t, J=7.1 Hz), 4.88 (1H, td, J=8.4, 5.7 Hz), 5.59 (1H, t, J=4.3 Hz), 6.03 (1H, s), 7.03 (1H, d, J=8.6 Hz), 7.18 (1H, dd, J=9.8, 2.1 Hz), 7.31 (1H, td, J=7.1, 2.0 Hz), 7.35-7.43 (3H, m), 7.69 (1H, dd, J=9.8, 0.8 Hz), 8.23 (1H, d, J=2.0 Hz), 8.31 (1H, s), 8.33 (0.3H, s).

Example 35

1-(5-tert-Butyl-2-(3-hydroxy-propyl)-2H-pyrazol-3-yl)-3-{(1S,4R)-4-[3-(2,6-dichlorophenyl)-[1,2,4]triazolo[4,3-a]pyridin-6-yloxy]-1,2,3,4-tetrahydronaphthalen-1-yl]-urea

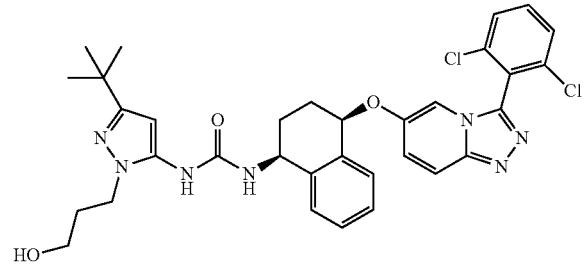 [SMILES: CC(C)(C)c1cc(NC(=O)N[C@H]2CC[C@@H](Oc3ccc4nnc(-c5c(Cl)cccc5Cl)n4c3)c3ccccc32)n(CCCO)n1]

a. 3-(5-Amino-3-tert-butyl-pyrazol-1-yl)-propan-1-ol (Intermediate 35a)

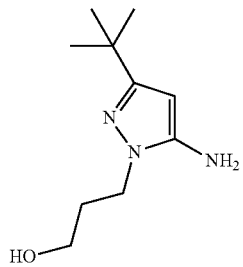

A solution of 4,4-dimethyl-3-oxo-pentanenitrile (0.7 g, 5.58 mmol) in ethanol (IMS grade, 5 mL) was treated with 3-hydrazino-propan-1-ol dihydrochloride (1 g, 6.13 mmol), followed by conc. HCl (0.05 mL), and the reaction mixture was heated at reflux for 18 h. The mixture was concentrated in vacuo and the residue was purified by FCC, using 0-10% [2M NH₃ in MeOH] in DCM to afford the title compound as a white gummy solid (0.94 g, 85%). LCMS (Method 3): Rt 0.42 min, m/z 198 [MH⁺].

b. [5-tert-Butyl-2-(3-hydroxy-propyl)-2H-pyrazol-3-yl]-carbamic acid 2,2,2-trichloroethyl ester (Intermediate 35b)

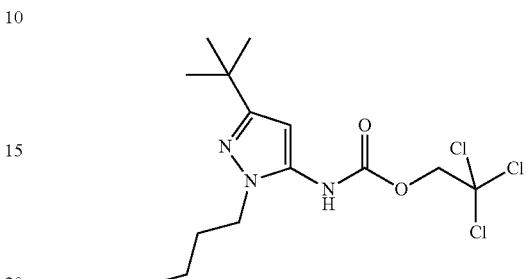

A solution of Intermediate 35a (0.94 g, 4.76 mmol) in EtOAc (15 mL) was treated with aqueous NaOH (1M, 8.58 mmol), followed by 2,2,2-trichloroethyl chloroformate (0.79 mL, 5.72 mmol) and stirred at RT for 1.5 h. The two layers were separated, and the organic layer was washed with water (2×10 mL), dried (MgSO₄), filtered and concentrated in vacuo to afford the title compound as a white solid (1.12 g, 63%). LCMS (Method 3): Rt 3.72 min, m/z 372/374 [MH⁺].

c. 1-(5-tert-Butyl-2-(3-hydroxy-propyl)-2H-pyrazol-3-yl)-3-{(1S,4R)-4-[3-(2,6-dichlorophenyl)-[1,2,4]triazolo[4,3-a]pyridin-6-yloxy]-1,2,3,4-tetrahydronaphthalen-1-yl]-urea (Example 35)

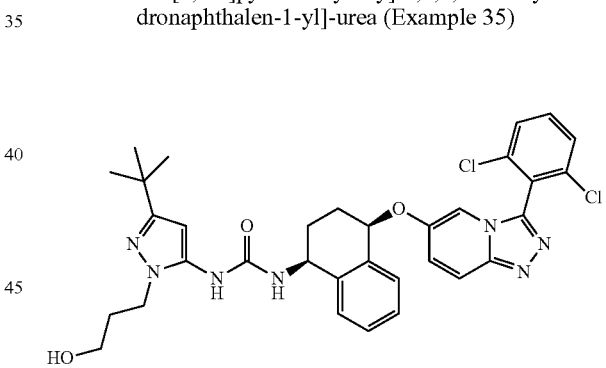

A mixture of Intermediate 35b (200 mg, 0.54 mmol), Intermediate 26d (228 mg, 0.54 mmol), and DIPEA (140 μL, 0.80 mmol) in dioxane (2 mL) was stirred at 70° C. for 18 h. The reaction mixture was cooled to RT, diluted with DCM (10 mL), and washed with water (2×10 mL). The aqueous layer was extracted with DCM, and the combined organics were passed through a phase separator and concentrated in vacuo and the resultant residue was purified by FCC, using 0-5% [2M NH₃ in MeOH] in DCM to afford the title compound (270 mg, 76%). A 50 mg sample of this was purified by MDAP (Method 7) to afford the title compound as a glassy solid (17 mg). LCMS (Method 5): Rt 4.24 min, m/z 648.4 [MH⁺]. ¹H NMR (400 MHz, d₆-DMSO): 1.20 (9H, s), 1.79-1.87 (2H, m), 1.88-2.14 (4H, m), 3.41 (2H, t, J=5.9 Hz), 3.91 (2H, t, J=7.2 Hz), 4.58 (1H, br s), 4.79-4.87 (1H, m), 5.55 (1H, t, J=4.2 Hz), 6.03 (1H, s), 6.93 (1H, d, J=8.8 Hz), 7.23-7.29 (1H, m), 7.32-7.38 (4H, m), 7.69-7.79 (3H, m), 7.91 (1H, dd, J=9.6 Hz, 0.9 Hz), 7.98 (1H, d, J=1.7 Hz), 8.17 (1H, s).

Biological Assays.

P38alpha Enzyme Inhibition Assay.

The inhibitory activity of compounds was determined using an Alphascreen® (Perkin Elmer) based kinase activity assay. Kinase reactions consisted of 25 mM HEPES pH 7.5, 10 mM $MgCl_2$, 100 M $Na_3VO_4$, 2 mM DTT, 0.05 mg/ml Tween 20, 100 pM p38alpha (Invitrogen, PV3304), 1% DMSO and 0.3 µg/ml ATF-2 fusion protein (New England Biolabs, 9224). Compounds were incubated under these conditions for 2 hours, at 25° C., prior to the initiation of the kinase activity by the addition of the 250 µM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83 ng/uL anti-phospho-ATF2 antibody (Abcam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. $IC_{50}$ values were determined from concentration-response curves. Results are shown in the following Table:

| Example | p38α inhibition |
| --- | --- |
| 1 | ++++ |
| 2 | ++++ |
| 3 | ++++ |
| 4 | ++++ |
| 5 | ++++ |
| 6 | ++ |
| 7 | ++++ |
| 8 | ++++ |
| 9 | ++++ |
| 11 | ++++ |
| 12 | ++++ |
| 14 | +++ |
| 15 | ++++ |
| 16 | ++++ |
| 17 | ++++ |
| 18 | ++++ |
| 19 | ++++ |
| 20 | ++ |
| 21 | ++++ |
| 22 | ++++ |
| 23 | ++++ |
| 24 | ++++ |
| 25 | ++++ |
| 26 | ++++ |
| 27 | ++++ |
| 28 | ++++ |
| 29 | ++++ |
| 30 | ++++ |
| 31 | ++++ |
| 32 | ++++ |
| 33 | ++++ |
| 34 | ++++ |

In the table above, p38α binding potencies ($IC_{50}$ values) are indicated as follows: 7000 to 500 nM, '+'; 500 to 100 nM, '++'; 100 to 10 nM '+++'; <10 nM, '++++'.

LPS-Stimulated PBMC TNFα Release Assay.

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3 h in a humidified incubator. After incubation, the medium was replaced (with medium containing 1% foetal bovine serum), and the plate incubated at 37° C., for 1 h, in the presence of test compound or the appropriate vehicle. LPS (10 ng/ml), or an appropriate vehicle control, was then added to the cells, and the plate returned to the incubator for 18 h. Cell-free supernatants were removed and assayed for TNFα levels using an ELISA kit from R&D Systems.

A dose response curve to each test compound was performed and the effect of compound in each experiment was expressed as a percentage inhibition of the control TNFα release. Dose response curves were plotted and compound potency ($IC_{50}$) was determined. Compounds were tested in at least three separate experiments. Results are shown in the following Table:

| Example numbers | p38α inhibition |
| --- | --- |
| 1, 2, 3, 4, 7, 8, 9, 11, 14, 15, 23, 26, 27, 28, 29, 30, 31, 32, 33, 34 | ++++ |
| 5, 10, 12, 18, 19, 22 | +++ |
| 13, 17 | ++ |

In the table above, p38α potencies ($IC_{50}$ values) are indicated as follows: >1000 nM, '+'; 1000 to 100 nM, '++'; 100 to 10 nM, '+++'; <10 nM, '++++'. All compounds tested exhibited $IC_{50}$ values <1000 nM.

Pre-Clinical Mouse Model of COPD—Tobacco Smoke Induced Pulmonary Inflammation.

Previous studies have established that the number of inflammatory cells recovered by bronchoalveolar lavage (BAL) is significantly elevated 24 h following the final of four consecutive daily tobacco smoke (TS) exposures. This timepoint may be used in the described model.

Protocols for the exposure of mice to TS, obtaining bronchoalveolar lavage fluid (BALF) and preparation of cytospin slides for differential cell counts are as outlined below.

Daily Exposure of Mice to TS for 4 Consecutive Days.

In this exposure protocol, mice are exposed in groups of 5 in individual clear polycarbonate chambers (27 cm×16 cm×12 cm). The TS from the cigarettes is allowed to enter the exposure chambers at a flow rate of 100 ml/min. In order to minimise any potential problems caused by repeated exposure to a high level of TS, the exposure of the mice to TS is increased gradually over the exposure period to a maximum of 6 cigarettes. The exposure schedule used over the four days is as follows:

| | |
| --- | --- |
| Day 1: 5 cigarettes | (approximately 25 min exposure) |
| Day 2: 7 cigarettes | (approximately 35 min exposure) |
| Day 3: 9 cigarettes | (approximately 45 min exposure) |
| Day 4: 9 cigarettes | (approximately 45 min exposure) |

A further group of mice are exposed to air on a daily basis for equivalent lengths of time as controls (no TS-exposure).

Bronchoalveolar Lavage (BAL) Analysis.

Bronchoalveolar lavage is performed as follows: the trachea is cannulated using a 10 mm long Luer-fitting stainless steel cannula. Phosphate buffered saline (PBS) is used as the lavage fluid. A volume of 0.4 ml is gently instilled and withdrawn 3 times, using a 1 ml syringe and then placed in an Eppendorf tube and kept on ice prior to subsequent determinations.

Cell Counts:

Lavage fluid is separated from cells by centrifugation and the supernatant decanted and frozen for subsequent analyses. The cell pellet is re-suspended in a known volume of PBS and total cell numbers calculated by counting a stained (Turks stain) aliquot under a microscope using a haemocytometer.

Differential Cell Counts are Performed as Follows:

The residual cell pellet is diluted to approximately $10^5$ cells per ml. A volume of 500 µl is placed in the funnel of a cytospin slide and centrifuged for 6 min at 800 rpm, RCF=72.26×g (Shandon Cytospin 3). The slide is air-dried and stained using Wrights/Giemsa stain as per the proprietary instructions. When dried and cover-slipped, differential cell counts are performed using light microscopy. Approximately four hundred cells are counted by an unbiased operator using light microscopy. Cells are differentiated using standard morphometric techniques.

Drug Treatment

Rodents such as mice and rats are obligate nose breathers, thus oral delivery of test materials (such as therapeutic agents) for inhalation will not produce good lung exposure. As a consequence, delivery of therapeutic agents to the lungs in rodents is generally achieved by intranasal, intratracheal or inhalation by either nose-only or whole body aerosol exposure.

Nose-only or whole body aerosol exposure methods utilize large amounts of test material and are generally reserved for inhalation toxicology studies rather than more routine pharmacological efficacy studies. Intratracheal administration is a very efficient delivery method as almost all of the test material is delivered to the lungs but is an invasive technique. For studies in the mouse particularly, it is also technically demanding as the diameter of the trachea is small. The intranasal route is less invasive than the intratracheal route and so is particularly suitable for repeat dosing studies such as the four day mouse model described. Following intranasal administration, ~50% of the dose administered is delivered to the lungs (see Eyles J E, Williamson E D and Alpar H O. 1999, Int J Pharm, 189(1):75-9), which is incorporated herein by reference in its entirety.

As a surrogate route for oral inhalation, mice are dosed intra-nasally with vehicle (0.2% tween 80 in saline) containing test compound. The control groups of mice receive vehicle 1 hr prior to being exposed to air or TS.

Data Management and Statistical Analysis.

All results are presented as individual data points for each animal, and the mean value is calculated for each group. Since tests for normality are positive, the data are subjected to a one-way analysis of variance test (ANOVA), followed by a Bonferroni correction for multiple comparisons in order to test for statistically significant differences between treatment groups. A "p" value of <0.05 is considered to be statistically significant. Percentage inhibitions are automatically calculated within Excel spreadsheets for the cell data using the formula below:

$$\% \text{ Inhibition} = \left(1 - \left(\frac{\text{Treatment group result} - \text{air group result}}{TS \text{ vehicle group result} - \text{air group result}}\right)\right) \times 100$$

Inhibition data for other parameters are calculated manually using the above formula.

Compounds of the invention may be tested in the reported tobacco induced pulmonary inflammation model to evaluate their anti-inflammatory effect in an animal model of COPD.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound represented by formula (I) or a pharmaceutically acceptable salt thereof:

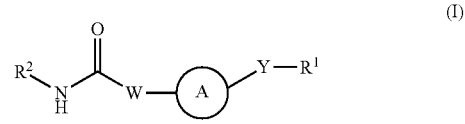

(I)

wherein;
W is N or O, wherein N is substituted with hydrogen, $C_1$-$C_6$ alkyl, or $C_3$-$C_5$-cycloalkyl;
Y is a group —S(O)$_p$— wherein p is 0, 1, or 2; a group —O(CR$^3$R$^4$)—; a group —(CR$^5$R$^6$)$_n$—; a group —NR$^7$—; a group —OC(O)—; a group —OC(O)NH—; or a group —OC(O)O—;
R$^3$, R$^4$, R$^5$, and R$^6$ are each independently hydrogen, fluorine, or $C_1$-$C_6$ alkyl; or, respectively, R$^3$ and R$^4$, or R$^5$ and R$^6$ may form, together with the carbon atom to which they are attached, a 3-6 membered saturated carbocyclic monocyclic ring optionally substituted with a $C_1$-$C_6$ alkyl group, hydroxyl group, or halogen;
n is 0, 1, 2, or 3;
R$^7$ is hydrogen, $C_1$-$C_6$ alkyl, or $C_3$-$C_7$ cycloalkyl, wherein such $C_1$-$C_6$ alkyl, or $C_3$-$C_7$ cycloalkyl are optionally substituted with a $C_1$-$C_3$ alkyl group, $C_3$-$C_6$ cycloalkyl group, hydroxyl group, cyano group, or halogen;
R$^1$ is a group of formula (IIa), (IIb), or (IIc);

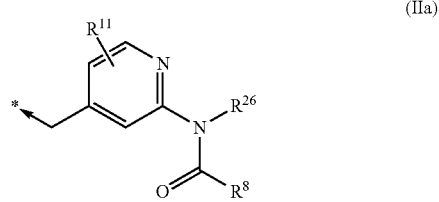

(IIa)

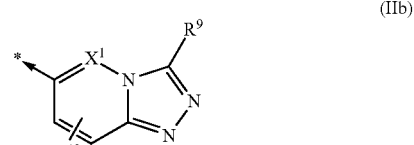

(IIb)

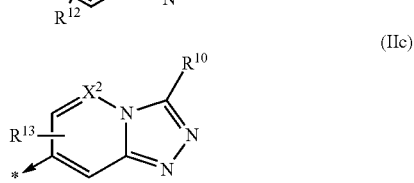

(IIc)

wherein

R$^8$ is —(C$_1$-C$_6$alkylene)-NR$^A$R$^B$, —(C$_3$-C$_7$cycloalkylene)-NR$^A$R$^B$, —NR$^A$R$^B$, —N(R$^C$)—(C$_2$-C$_6$alkylene)-NR$^A$R$^B$, —N(R$^C$)—(C$_3$-C$_7$cycloalkylene)-NR$^A$R$^B$, or —R$^C$;

R$^A$ and R$^B$ are at each occurrence independently hydrogen, C$_1$-C$_6$ alkyl, or C$_3$-C$_7$ cycloalkyl, said C$_1$-C$_6$ alkyl and C$_3$-C$_7$ cycloalkyl being optionally substituted by a C$_1$-C$_3$ alkyl group, C$_3$-C$_7$cycloalkyl group, —OR$^D$, —SR$^D$, —NR$^E$R$^F$, —CN, or halo; alternatively, R$^A$ and R$^B$ may form, together with the nitrogen atom to which they are attached, a 5-11 membered saturated monocyclic or bicyclic ring system in which said 5-11-membered saturated monocyclic or bicyclic ring is optionally substituted by one or more of —OR$^D$, —CN, halo, C$_1$-C$_6$ alkyl, or C$_3$-C$_7$ cycloalkyl, wherein said C$_1$-C$_6$ alkyl and C$_3$-C$_7$ cycloalkyl may be optionally substituted by a C$_1$-C$_3$ alkyl group, C$_3$-C$_7$cycloalkyl group, —OR$^D$, —CN or halo; and wherein, optionally, said 5-11-membered saturated monocyclic or bicyclic ring contains a further heteroatom which is oxygen or nitrogen, said nitrogen atom optionally substituted by C$_1$-C$_6$ alkyl or C$_3$-C$_6$ cycloalkyl wherein any of said C$_1$-C$_6$ alkyl or C$_3$-C$_6$ cycloalkyl may be optionally substituted by a C$_1$-C$_6$ alkyl group, C$_3$-C$_7$ cycloalkyl group, —OR$^D$, —CN, or halo;

R$^C$ is at each occurrence independently hydrogen, C$_1$-C$_6$ alkyl, or C$_3$-C$_6$ cycloalkyl, said C$_1$-C$_6$ alkyl and C$_3$-C$_6$ cycloalkyl being optionally substituted by a C$_1$-C$_3$ alkyl group, OR$^D$, CN, or halo;

R$^D$ is at each occurrence independently hydrogen, —CH$_3$, or —C$_2$H$_5$;

R$^E$ and R$^F$ are at each occurrence independently hydrogen, C$_1$-C$_6$ alkyl, or C$_3$-C$_7$ cycloalkyl, said C$_1$-C$_6$ alkyl and C$_3$-C$_7$ cycloalkyl being optionally substituted by a C$_1$-C$_3$ alkyl group, C$_3$-C$_7$cycloalkyl group, —OR$^D$, —SR$^D$, —CN or halo; or R$^E$ and R$^F$ may form, together with the nitrogen atom to which they are attached, a 5-7 membered saturated ring system in which said 5-7-membered saturated ring is optionally substituted by one or more of —OR$^D$, —CN, halo, C$_1$-C$_6$ alkyl, or C$_3$-C$_7$ cycloalkyl, said C$_1$-C$_6$ alkyl and C$_3$-C$_7$ cycloalkyl being optionally substituted by a C$_1$-C$_3$ alkyl group, C$_3$-C$_7$cycloalkyl group, —OR$^D$, —CN or halo; and wherein, optionally, said 5-7-membered saturated ring contains a further heteroatom which is oxygen or nitrogen, said nitrogen atom optionally substituted by C$_1$-C$_6$ alkyl or C$_3$-C$_6$ cycloalkyl wherein any of said C$_1$-C$_6$ alkyl or C$_3$-C$_6$ cycloalkyl may be optionally substituted by a C$_1$-C$_6$ alkyl group, C$_3$-C$_7$ cycloalkyl group, —OR$^D$, —CN, or halo;

R$^{26}$ is hydrogen, —CH$_3$, or —C$_2$H$_5$;

X$_1$ and X$_2$ are each independently a group —(CH)— or a nitrogen atom;

R$^9$ and R$^{10}$ are independently, C$_1$-C$_6$ alkyl, C$_3$-C$_6$ cycloalkyl, phenyl which is optionally substituted, 5- or 6-membered monocyclic heteroaryl which is optionally substituted, or a group of formula (IIIa) or (IIIb):

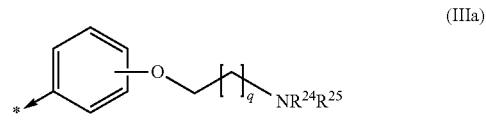

(IIIa)

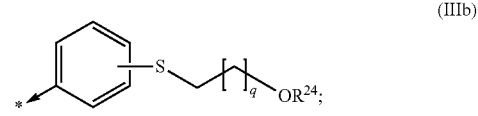

(IIIb)

wherein q is 1 or 2; and R$^{24}$ and R$^{25}$ are independently hydrogen or C$_1$-C$_6$ alkyl, or R$^{24}$ and R$^{25}$ taken together with the nitrogen to which they are attached form a 6-membered heterocyclic ring optionally containing a further heteroatom selected from N and O;

R$^{11}$, R$^{12}$, and R$^{13}$ are independently hydrogen, C$_1$-C$_6$ alkyl, or halogen;

A is a divalent cycloalkylene radical having 5, 6 or 7 ring atoms; said cycloalkylene ring being attached to W and Y, and fused to a phenyl ring or to a monocyclic heteroaryl ring having 5 or 6 ring atoms, such phenyl or heteroaryl ring being optionally substituted by one or two groups R$^{27}$;

R$^{27}$ is at each occurrence independently selected from the group consisting of C$_1$-C$_6$ alkyl, halogen, and cyano;

R$^2$ is a group of formula (IVa), (IVb) or (IVc):

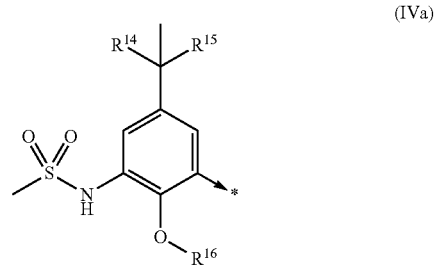

(IVa)

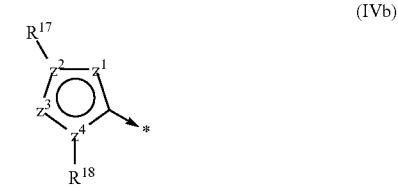

(IVb)

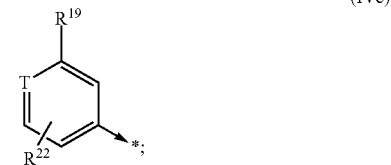

(IVc)

wherein

R$^{14}$ is —F, —CH$_2$OMe, or —CF$_2$CF$_3$;

R$^{15}$ and R$^{16}$ are independently —CH$_3$ or —C$_2$H$_5$;

R$^{17}$ is lone electron pair, hydrogen, —CF$_3$, —NR$^{E1}$R$^{F1}$, —(C$_3$-C$_7$cycloalkyl), —(C$_3$-C$_7$heterocycloalkyl), aryl, or heteroaryl wherein any of such —(C$_3$-C$_7$cycloalkyl), —(C$_3$-C$_7$heterocycloalkyl), aryl, or heteroaryl may be optionally substituted by a group C$_1$-C$_6$ alkyl, C$_3$-C$_7$ cycloalkyl, or halo; or

121

$R^{17}$ is a group of formula (V):

$$R^{20} \underset{*}{\overset{}{\diagdown}} R^{21}$$

wherein
$R^{20}$ is —F, —CH$_3$, —C$_2$H$_5$, —CH$_2$OH, —CH$_2$OMe, —CF$_2$CF$_3$, —CH$_2$SCH$_3$, —SCH$_3$ or —SC$_2$H$_5$;
$R^{21}$ is —CH$_3$ or —C$_2$H$_5$;
or
$R^{20}$ and $R^{21}$ may form, together with the carbon atom to which they are attached, a 3-7-membered monocyclic ring;
$R^{E1}$ and $R^{F1}$ are each independently C$_1$-C$_6$ alkyl optionally substituted by a C$_1$-C$_3$ alkyl group, —OR$^G$, —CN, or halo; alternatively, $R^{E1}$ and $R^{F1}$ may form, together with the nitrogen atom to which they are attached, a 5-11-membered saturated monocyclic or bicyclic ring system in which said 5-11-membered saturated monocyclic or bicyclic ring is optionally substituted by one or more of —OR$^G$, —CN, halo, C$_1$-C$_6$ alkyl, or C$_3$-C$_7$ cycloalkyl, said C$_1$-C$_6$ alkyl and C$_3$-C$_7$ cycloalkyl being optionally substituted by a C$_1$-C$_3$ alkyl group, C$_3$-C$_7$cycloalkyl group, —OR$^G$, —CN, or halo; and wherein, optionally, said 5-11-membered saturated monocyclic or bicyclic ring contains a further heteroatom which is oxygen or nitrogen, said nitrogen atom optionally substituted by C$_1$-C$_6$ alkyl or C$_3$-C$_6$ cycloalkyl;
$R^G$ is independently at each occurrence hydrogen, —CH$_3$, or —C$_2$H$_5$;
$R^{18}$ is lone electron pair, hydrogen, aryl, heteroaryl, —(C$_1$-C$_6$alkyl), —(C$_3$-C$_7$cycloalkyl), —(C$_3$-C$_7$heterocycloalkyl), (C$_5$-C$_7$heterocycloalkyl)-(C$_1$-C$_6$alkyl), or (C$_5$-C$_7$heterocycloalkyl)-(C$_3$-C$_6$ cycloalkyl); wherein any of such aryl, heteroaryl, —(C$_1$-C$_6$alkyl), —(C$_3$-C$_7$cycloalkyl), —(C$_3$-C$_7$heterocycloalkyl), (C$_5$-C$_7$heterocycloalkyl)-(C$_1$-C$_6$alkyl), or (C$_5$-C$_7$heterocycloalkyl)-(C$_3$-C$_6$ cycloalkyl) may be optionally substituted by a —CN, —OH, halo, —COOR$^M$, C$_1$-C$_6$alkyl, C$_3$-C$_6$cycloalkyl, —O—(C$_1$-C$_6$alkyl), —O—(C$_3$-C$_6$cycloalkyl), —S—(C$_1$-C$_6$alkyl), —S—(C$_3$-C$_6$cycloalkyl), —NR$^H$R$^J$, —N(R$^L$)(C$_2$-C$_6$alkylene)-NR$^H$R$^J$, —N(R$^L$)(C$_3$-C$_7$cycloalkylene)-NR$^H$R$^J$, —(C$_1$-C$_6$alkylene)-NR$^H$R$^J$, —(C$_3$-C$_7$cycloalkylene)-NR$^H$R$^J$, —O—(C$_2$-C$_6$alkylene)-NR$^H$R$^J$, —O—(C$_3$-C$_7$cycloalkylene)-NR$^H$R$^J$, —S—(C$_2$-C$_6$alkylene)-NR$^H$R$^J$, —S—(C$_3$-C$_7$cycloalkylene)-NR$^H$R$^J$, —N(R$^L$)C(O)—(C$_1$-C$_6$alkylene)-NR$^H$R$^J$, —N(R$^L$)C(O)—(C$_3$-C$_7$cycloalkylene)-NR$^H$R$^J$, —C(O)N(R$^L$)—(C$_2$-C$_6$alkylene)-NR$^H$R$^J$, —C(O)N(R$^L$)—(C$_3$-C$_7$cycloalkylene)-NR$^H$R$^J$, —C(O)N(R$^L$)—(C$_2$-C$_6$alkylene)-OR$^M$, —C(O)N(R$^L$)—(C$_3$-C$_7$cycloalkylene)-OR$^M$, —N(R$^L$)C(O)N(R$^H$R$^J$), —C(O)N(R$^H$R$^J$), —N(R$^L$)C(O)N(R$^L$)—(C$_2$-C$_6$alkylene)-NR$^H$R$^J$, —N(R$^L$)C(O)N(R$^L$)—(C$_3$-C$_7$cycloalkylene)-NR$^H$R$^J$, —O—(C$_2$-C$_6$alkylene)-OR$^M$, —O—(C$_3$-C$_7$cycloalkylene)-OR$^M$, —S—(C$_2$-C$_6$alkylene)-OR$^M$, —S—(C$_3$-C$_7$cycloalkylene)-OR$^M$, —N(R$^L$)S(O)$_2$—(C$_1$-C$_6$alkylene)-NR$^H$R$^J$, —N(R$^L$)S(O)$_2$—(C$_3$-C$_7$cycloalkylene)-NR$^H$R$^J$, —S(O)$_2$N(R$^L$)—(C$_2$-C$_6$alkylene)-NR$^H$R$^J$, —S(O)$_2$N(R$^L$)—(C$_3$-C$_7$cycloalkylene)-NR$^H$R$^J$, —S(O)$_2$N(R$^L$)—(C$_2$-C$_6$alkylene)-OR$^M$, —S(O)$_2$N(R$^L$)—(C$_3$-C$_7$cycloalkylene)-OR$^M$, —N(R$^L$)S(O)$_2$—(C$_2$-C$_6$alkylene)-OR$^M$, —N(R$^L$)S(O)$_2$—(C$_3$-C$_7$cycloalkylene)-OR$^M$, —S(O)$_2$N(R$^H$R$^J$), —N(R$^L$)S(O)$_2$R$^L$, —N(R$^L$)C(O)R$^L$, OR$^L$, SR$^L$, —(C$_3$-C$_7$heterocycloalkyl), (C$_5$-C$_7$heterocycloalkyl)-(C$_1$-C$_6$ alkyl), and (C$_5$-C$_7$ heterocycloalkyl)-(C$_3$-C$_6$ cycloalkyl);
wherein any of said C$_1$-C$_6$alkyl, C$_3$-C$_6$cycloalkyl, —(C$_2$-C$_6$alkylene)-, —(C$_3$-C$_7$cycloalkylene)-, —(C$_3$-C$_7$heterocycloalkyl), (C$_5$-C$_7$heterocycloalkyl)-(C$_1$-C$_6$ alkyl), (C$_5$-C$_7$ heterocycloalkyl)-(C$_3$-C$_6$ cycloalkyl) and (C$_5$-C$_7$heterocycloalkyl)carbonyl portion in the above listed groups may be optionally substituted by a C$_1$-C$_6$ alkyl group, C$_3$-C$_7$ cycloalkyl group, —OR$^M$ or halo;
$R^H$ and $R^J$ are at each occurrence independently hydrogen, C$_1$-C$_6$ alkyl, or C$_3$-C$_6$ cycloalkyl, said C$_1$-C$_6$ alkyl or C$_3$-C$_6$ cycloalkyl being optionally substituted by a C$_1$-C$_3$ alkyl group, —OR$^M$, —CN, or halo; alternatively, $R^H$ and $R^J$ may form, together with the nitrogen atom to which they are attached, a 5-11 membered saturated monocyclic or bicyclic ring system in which said 5-11-membered saturated monocyclic or bicyclic ring is optionally substituted by one or more of —OR$^M$, —CN, halo, C$_1$-C$_6$ alkyl, or C$_3$-C$_7$ cycloalkyl, said C$_1$-C$_6$ alkyl and C$_3$-C$_7$ cycloalkyl being optionally substituted by a C$_1$-C$_3$ alkyl group, C$_3$-C$_7$cycloalkyl group, —OR$^M$, —CN, or halo; and wherein, optionally, said 5-11-membered saturated monocyclic or bicyclic ring contains a further heteroatom which is oxygen or nitrogen, said nitrogen atom optionally substituted by C$_1$-C$_6$ alkyl or C$_3$-C$_6$ cycloalkyl, wherein any of said C$_1$-C$_6$ alkyl or C$_3$-C$_6$ cycloalkyl may be optionally substituted by a C$_1$-C$_6$ alkyl group, C$_3$-C$_7$ cycloalkyl group, —OR$^M$, —CN, or halo; and/or $R^H$ and $R^J$ may be linked to one carbon atom of the —(C$_2$-C$_6$alkylene)- or —(C$_3$-C$_7$cycloalkylene)-portion of the group linked to the nitrogen to which they are connected to form a saturated cycle of up to 6 ring atoms;
$R^L$ is at each occurrence independently hydrogen, C$_1$-C$_6$ alkyl, or C$_3$-C$_6$ cycloalkyl, said C$_1$-C$_6$ alkyl or C$_3$-C$_6$ cycloalkyl being optionally substituted by a C$_1$-C$_3$ alkyl group, —OR$^M$, —CN, or halo;
$R^M$ is at each occurrence independently hydrogen, C$_1$-C$_4$ alkyl, or C$_3$-C$_6$ cycloalkyl, said C$_1$-C$_4$ alkyl or C$_3$-C$_6$ cycloalkyl being optionally substituted by hydroxyl, —CN, or halo;
$R^{19}$ is hydrogen, —CF$_3$, —NR$^E$R$^F$, —(C$_3$-C$_7$cycloalkyl), —(C$_3$-C$_7$heterocycloalkyl), aryl, or heteroaryl wherein any of such —(C$_3$-C$_7$cycloalkyl), —(C$_3$-C$_7$heterocycloalkyl), aryl, or heteroaryl may be optionally substituted by a C$_1$-C$_6$ alkyl group, C$_3$-C$_7$ cycloalkyl group, or halo; or
$R^{19}$ is a group of formula (V):

$$R^{20} \underset{\downarrow *}{\overset{}{\diagdown}} R^{21}$$

wherein $R^{20}$, $R^{21}$, $R^E$ and $R^F$ are as above defined;
$z^1$, $z^2$, $z^3$, and $z^4$ are independently selected from the group consisting of C, N, S, O, —CH—, and —NH—, in such a combination that the resulting ring formed is an aromatic system;

T is —N= or —$CR^{28}$=;

$R^{28}$ is H, halo, —$CH_3$, or —CN;

$R^{22}$ is H, halo, —$CH_3$, or —CN;

with the provisos that:

(1) when $z^1$=—CH—, $z^2$=—C—, $z^3$=—O—, $z^4$=—N—, $R^{18}$ is an electron lone pair, $R^{17}$ is a group of formula (V), and $R^{21}$ is —$CH_3$ or —$C_2H_5$;

then $R^{20}$ is —F, —$CH_2OMe$, or —$CF_2CF_3$;

(2) when $z^1$=—CH—, $z^2$=—C—, $z^3$=—N—, $z^4$=—N—, $R^{17}$ is a group of formula (V), $R^{21}$ is —$CH_3$ or —$C_2H_5$ and $R^{20}$ is —$CH_3$, —$C_2H_5$; —$CH_2OH$, —$CH_2SCH_3$, —$SCH_3$, or —$SC_2H_5$, and $R_{18}$ is a phenyl ring;

then:

(a) said phenyl ring is substituted by a group which is selected from the group consisting of —CN, —CO-$OR^M$, $C_3$-$C_6$cycloalkyl, —O—($C_1$-$C_6$alkyl), —O—($C_3$-$C_6$cycloalkyl), —S—($C_1$-$C_6$alkyl), —S—($C_3$-$C_6$cycloalkyl), —$NR^HR^J$, —$N(R^L)(C_2$-$C_6$alkylene)-$NR^HR^J$, —$N(R^L)(C_3$-$C_7$cycloalkylene)-$NR^HR^J$, —($C_3$-$C_7$cycloalkylene)-$NR^HR^J$, —O—($C_3$-$C_7$cycloalkylene)-$NR^HR^J$, —S—($C_2$-$C_6$alkylene)-$NR^HR^J$, —S—($C_3$-$C_7$cycloalkylene)-$NR^HR^J$, —$N(R^L)C(O)$—($C_1$-$C_6$alkylene)-$NR^HR^J$, —$N(R^L)C(O)$—($C_3$-$C_7$cycloalkylene)-$NR^HR^J$, —$C(O)N(R^L)$—($C_2$-$C_6$alkylene)-$NR^HR^J$, —$C(O)N(R^L)$—($C_3$-$C_7$cycloalkylene)-$NR^HR^J$, —$C(O)N(R^L)$—($C_2$-$C_6$alkylene)-$OR^M$, —$C(O)N(R^L)$—($C_3$-$C_7$cycloalkylene)-$OR^M$, —$N(R^L)C(O)NR^HR^J$, —$C(O)NR^HR^J$, —$N(R^L)C(O)N(R^L)$—($C_2$-$C_6$alkylene)-$NR^HR^J$—$N(R^L)C(O)N(R^L)$—($C_3$-$C_7$cycloalkylene)-$NR^HR^J$, —O—($C_2$-$C_6$alkylene)-$OR^M$, —O—($C_3$-$C_7$cycloalkylene)-$OR^M$, —S—($C_2$-$C_6$alkylene)-$OR^M$, —S—($C_3$-$C_7$cycloalkylene)-$OR^M$, —$N(R^L)S(O)_2$—($C_1$-$C_6$alkylene)-$NR^HR^J$, —$N(R^L)S(O)_2$—($C_3$-$C_7$cycloalkylene)-$NR^HR^J$, —$S(O)_2N(R^L)$—($C_2$-$C_6$alkylene)-$NR^HR^J$, —$S(O)_2N(R^L)$—($C_3$-$C_7$cycloalkylene)-$NR^HR^J$, —$S(O)_2N(R^L)$—($C_2$-$C_6$alkylene)-$OR^M$, —$S(O)_2N(R^L)$—($C_3$-$C_7$cycloalkylene)-$OR^M$, —$N(R^L)S(O)_2$—($C_2$-$C_6$alkylene)-$OR^M$, —$N(R^L)S(O)_2$—($C_3$-$C_7$cycloalkylene)-$OR^M$, —$S(O)_2N(R^HR^J)$, —$N(R^L)S(O)_2R^L$, —$N(R^L)C(O)R^L$, $SR^L$, —$C_3$-$C_7$heterocycloalkyl), ($C_5$-$C_7$heterocycloalkyl)-($C_1$-$C_6$ alkyl), and ($C_5$-$C_7$ heterocycloalkyl)-($C_3$-$C_6$ cycloalkyl);

wherein any of such $C_1$-$C_6$alkyl, $C_3$-$C_6$cycloalkyl, —($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl), and ($C_5$-$C_7$heterocycloalkyl)carbonyl portion in the above listed groups may be optionally substituted by a $C_1$-$C_6$ alkyl group, $C_3$-$C_7$ cycloalkyl group, —$OR^M$, or halo; or (b) said phenyl ring is substituted by a group which is —($C_1$-$C_6$alkylene)-$NR^HR^J$ or —O—($C_2$-$C_6$alkylene)-$NR^HR^J$ wherein $R^H$ and $R^J$, which are not both hydrogen, are at each occurrence independently hydrogen, $C_1$-$C_6$ alkyl, or $C_3$-$C_6$ cycloalkyl, said $C_1$-$C_6$ alkyl or $C_3$-$C_6$ cycloalkyl being substituted by —$OR^M$, —CN or halo; alternatively, $R^H$ and $R^J$ may form, together with the nitrogen atom to which they are attached, a 5-11 membered saturated monocyclic or bicyclic ring system in which said 5-11-membered saturated monocyclic or bicyclic ring is substituted by one or more of —$OR^M$, —CN, halo, $C_1$-$C_6$ alkyl, or $C_3$-$C_7$ cycloalkyl, said $C_1$-$C_6$ alkyl and $C_3$-$C_7$ cycloalkyl being optionally substituted by a $C_1$-$C_3$ alkyl group, $C_3$-$C_7$cycloalkyl group, —$OR^M$, —CN, or halo; and wherein, optionally, said 5-11-membered saturated monocyclic or bicyclic ring contains a further heteroatom which is oxygen or nitrogen, said nitrogen atom optionally substituted by $C_1$-$C_6$ alkyl or $C_3$-$C_6$ cycloalkyl, wherein any of said $C_1$-$C_6$ alkyl or $C_3$-$C_6$ cycloalkyl may be optionally substituted by a $C_1$-$C_6$ alkyl group, $C_3$-$C_7$ cycloalkyl group, —$OR^M$, —CN, or halo; or (c) said phenyl ring is substituted by a group $C_5$-$C_7$heterocycloalkyl)-($C_1$-$C_6$ alkyl), which is substituted by a $C_1$-$C_6$ alkyl group, $C_3$-$C_7$ cycloalkyl group, —$OR^M$, or halo; or (d) said phenyl ring is substituted by a group —$OR^L$ wherein $R^L$ is $C_1$-$C_6$ alkyl or $C_3$-$C_6$ cycloalkyl, said $C_1$-$C_6$ alkyl or $C_3$-$C_6$ cycloalkyl being optionally substituted by a $C_1$-$C_3$ alkyl group, —$OR^M$, —CN, or halo; or (e) said phenyl ring is substituted by a group $C_1$-$C_6$ alkyl which is substituted by a $C_3$-$C_7$ cycloalkyl group, $OR^M$, or halo;

and (3) when $R^{19}$ is a morpholine ring and T is —$CR^{28}$= or —N=;

then $R^{22}$, if present at position ortho to group T of the aromatic ring, is —$CH_3$ or —CN.

2. A compound or pharmaceutically acceptable salt thereof according to claim 1, which is a compound of formula (Ia) in which the carbon stereogenic center on the cycloalkylene portion of ring A which is linked to group W and identified with number (1) herebelow, possesses the absolute configuration herebelow represented:

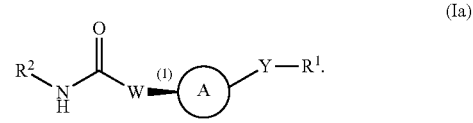

(Ia)

3. A compound or pharmaceutically acceptable salt thereof according to claim 1, which is a compound of formula (Ib) in which the carbon stereogenic centers on the cycloalkylene portion of ring A which are linked to group W and Y and identified, respectively, with numbers (1) and (2) herebelow, possess the absolute configuration herebelow represented:

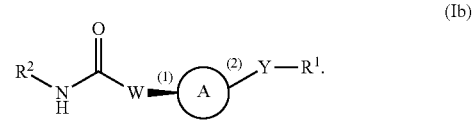

(Ib)

4. A compound or pharmaceutically acceptable salt thereof according to claim 1, wherein A is group represented by one of the following formulae:

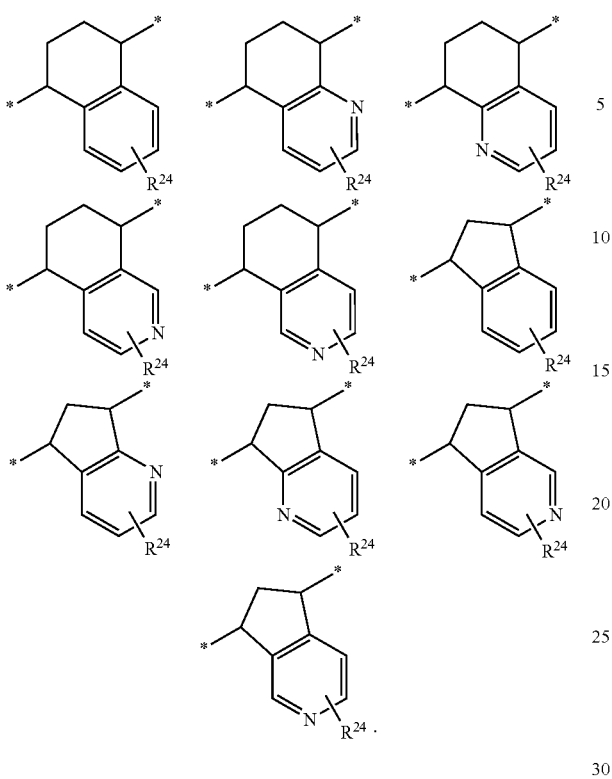

5. A compound or pharmaceutically acceptable salt thereof according to claim 1, wherein W is NH or O.

6. A compound or pharmaceutically acceptable salt thereof according to claim 1, wherein Y is $-S(O)_p-$, $-O(CR^3R^4)_n-$, $-(CR^5R^6)_n-$, or $-NR^7-$; p is zero, and n is 0, 1, or 2.

7. A compound or pharmaceutically acceptable salt thereof according to claim 1, wherein $R^2$ is a group of formula (IVb):

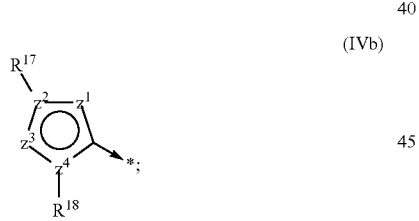

(IVb)

wherein $z^1=-CH-$, $z^2=C$, $z^3$ and $z^4$ are N, and $R^{17}$ is a group of formula (V):

(V)

wherein $R^{20}$ is $-CH_3$ or $-CH_2OH$, $R^{21}$ is $-CH_3$, and wherein
$R^{18}$ is phenyl, which is substituted by a group which is $-(C_1-C_6\text{alkylene})-NR^HR^J$ or $-O-(C_2-C_6\text{alkylene})-NR^HR^J$ wherein $R^H$ and $R^J$, which are not both hydrogen, are at each occurrence independently hydrogen, $C_1-C_6$ alkyl, or $C_3-C_6$ cycloalkyl, wherein said $C_1-C_6$ alkyl or $C_3-C_6$ cycloalkyl is substituted by $OR^M$, CN, or halo; alternatively, $R^H$ and $R^J$ may form, together with the nitrogen atom to which they are, attached a 5-11 membered saturated monocyclic or bicyclic ring system in which said 5-11-membered saturated monocyclic or bicyclic ring is substituted by one or more of $OR^M$, CN, halo, $C_1$-$C_6$ alkyl, or $C_3$-$C_7$ cycloalkyl, said $C_1$-$C_6$ alkyl and $C_3$-$C_7$ cycloalkyl being optionally substituted by a $C_1$-$C_3$ alkyl group, $C_3$-$C_7$ cycloalkyl group, $OR^M$, CN, or halo; and wherein optionally, said 5-11-membered saturated monocyclic or bicyclic ring contains a further heteroatom which is oxygen or nitrogen, said nitrogen atom optionally substituted by $C_1$-$C_6$ alkyl or $C_3$-$C_6$ cycloalkyl, wherein any of said alkyl or cycloalkyl may be optionally substituted by a $C_1$-$C_6$ alkyl group, $C_3$-$C_7$ cycloalkyl group, $OR^M$, CN, or halo;

or wherein $R^{18}$ is phenyl, which is substituted by a group $(C_5$-$C_7\text{heterocycloalkyl})$-$(C_1$-$C_6$ alkyl), which is substituted by a $C_1$-$C_6$ alkyl group, $C_3$-$C_7$ cycloalkyl group, $OR^M$, or halo;

or wherein $R^{18}$ is phenyl, which is substituted by a $C_1$-$C_6$ alkyl group which is substituted by a $C_3$-$C_7$ cycloalkyl group, $-OR^M$, or halo;

or wherein $R^{18}$ is phenyl, which is substituted by $-CN$, $-O-(C_1$-$C_6\text{alkyl})$, $-NR^HR^J$, $-O-(C_2$-$C_6\text{alkylene})$-$OR^M$, $-S-(C_2$-$C_6\text{alkylene})$-$OR^M$, $-(C_3$-$C_7\text{heterocycloalkyl})$, wherein any of said $C_1$-$C_6\text{alkyl}$, $-(C_2$-$C_6\text{alkylene})$-, $-(C_3$-$C_7\text{heterocycloalkyl})$, portion in the above listed groups may be optionally substituted by a $C_1$-$C_6$ alkyl group, $C_3$-$C_7$ cycloalkyl group, $OR^M$, or halo.

8. A compound or pharmaceutically acceptable salt thereof according to claim 1, wherein $R^2$ is a group of formula (IVb):

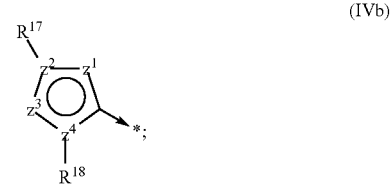

(IVb)

wherein $z^1=-CH-$, $z^2=C$, $z^3$ and $z^4$ are N, and $R^{17}$ is a group of formula (V):

(V)

wherein $R^{20}$ is $-CH_3$ or $-CH_2OH$, and $R^{21}$ is $-CH_3$, and $R^{18}$ is heteroaryl ring which is optionally substituted by a group $(C_5$-$C_7\text{heterocycloalkyl})$-$(C_1$-$C_6$ alkyl), which is optionally substituted by a $C_1$-$C_6$ alkyl group, $C_3$-$C_7$ cycloalkyl group, $OR^M$, or halo; or $R^{18}$ is heteroaryl ring which is optionally substituted by a group $-(C_1$-$C_6\text{alkylene})$-$NR^HR^J$ or $-O-(C_2$-$C_6\text{alkylene})$-$NR^HR^J$.

9. A compound or pharmaceutically acceptable salt thereof according to claim 1, wherein $R^2$ is a group of formula (IVb):

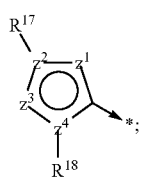
(IVb)

wherein $z^1$=—CH—, $z^2$=C, $z^3$ and $z^4$ are N, and $R^{17}$ is a group of formula (V):

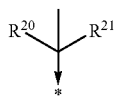
(V)

wherein $R^{20}$ is —$CH_3$ or —$CH_2OH$, and $R^{21}$ is —$CH_3$, and $R^{18}$ is a —($C_1$-$C_6$alkyl) group, optionally substituted by —OH, halo, or —$NR^HR^J$; or a ($C_5$-$C_7$heterocycloalkyl) group or ($C_5$-$C_7$heterocycloalkyl)-($C_1$-$C_6$alkyl) group which may be optionally substituted by a $C_1$-$C_6$ alkyl group, halo, or —OH.

10. A pharmaceutical composition, comprising a compound or pharmaceutically acceptable salt thereof according to claim 1, together with one or more pharmaceutically acceptable carriers.

11. A method for the treatment of a disease or condition which benefits from inhibition of p38 MAP kinase activity, comprising administering an effective amount of a compound or pharmaceutically acceptable salt thereof according to claim 1 to a subject in need thereof.

12. A method according to claim 11, wherein said disease or condition is chronic eosinophilic pneumonia, asthma, COPD, adult respiratory distress syndrome, exacerbation of airways hyper-reactivity consequent to other drug therapy or airways disease that is associated with pulmonary hypertension.

* * * * *

UNITED STATES PATENT AND TRADEMARK OFFICE
CERTIFICATE OF CORRECTION

PATENT NO.        : 8,835,431 B2                           Page 1 of 1
APPLICATION NO.   : 13/708191
DATED             : September 16, 2014
INVENTOR(S)       : Monique Bodil Van Niel et al.

It is certified that error appears in the above-identified patent and that said Letters Patent is hereby corrected as shown below:

In the Claims

In column 118, line 28, claim 1:

"-O($CR^3R^4$)-; a group -($CR^5R^6$)$_n$; a group"

should read as:

-- -O($CR^3R^4$)$_n$-; a group -($CR^5R^6$)$_n$; a group--

Signed and Sealed this
Seventeenth Day of March, 2015

Michelle K. Lee
*Director of the United States Patent and Trademark Office*